(12) United States Patent
Miller et al.

(10) Patent No.: US 10,314,547 B2
(45) Date of Patent: Jun. 11, 2019

(54) CALIBRATION OF A WEARABLE MEDICAL DEVICE

(71) Applicant: Halo Wearables LLC, Plymouth, MI (US)

(72) Inventors: Devin Warner Miller, Morgan, UT (US); David Rich Miller, Morgan, UT (US); Jeffrey Michael Lee, Morgan, UT (US)

(73) Assignee: Halo Wearables LLC, Morgan, UT (US)

( * ) Notice: Subject to any disclaimer, the term of this patent is extended or adjusted under 35 U.S.C. 154(b) by 1314 days.

(21) Appl. No.: 14/248,334

(22) Filed: Apr. 9, 2014

(65) Prior Publication Data
US 2015/0289820 A1 Oct. 15, 2015

(51) Int. Cl.
A61B 5/00 (2006.01)
A61B 5/024 (2006.01)
A61B 5/1495 (2006.01)
A61B 5/145 (2006.01)
A61B 5/02 (2006.01)
A61B 5/0295 (2006.01)
A61B 5/053 (2006.01)
A61B 5/117 (2016.01)

(52) U.S. Cl.
CPC .......... A61B 5/7221 (2013.01); A61B 5/0002 (2013.01); A61B 5/02438 (2013.01); A61B 5/1495 (2013.01); A61B 5/4875 (2013.01); A61B 5/681 (2013.01); A61B 5/7207 (2013.01); A61B 5/02007 (2013.01); A61B 5/0295 (2013.01); A61B 5/0535 (2013.01); A61B 5/0536 (2013.01); A61B 5/0537 (2013.01); A61B 5/117 (2013.01); A61B 5/14517 (2013.01); A61B 5/14532 (2013.01); A61B 5/14535 (2013.01); A61B 5/14542 (2013.01); A61B 5/684 (2013.01); A61B 5/6807 (2013.01); A61B 5/6814 (2013.01); A61B 5/6823 (2013.01); A61B 5/6824 (2013.01); A61B 5/6829 (2013.01); A61B 5/7246 (2013.01); A61B 5/7267 (2013.01); A61B 5/7275 (2013.01); A61B 5/7296 (2013.01); A61B 2560/0238 (2013.01); A61B 2560/0252 (2013.01)

(58) Field of Classification Search
CPC .................................................... A61B 5/7221
See application file for complete search history.

(56) References Cited

U.S. PATENT DOCUMENTS

2012/0084053 A1* 4/2012 Yuen .................... A61B 5/0002
702/160

* cited by examiner

Primary Examiner — Manuel A Rivera Vargas
(74) Attorney, Agent, or Firm — Miller IP Law, LLC

(57) ABSTRACT

A technology for a wearable medical device for monitoring medical parameters. Medical measurement data can be received at the wearable medical device from a medical measurement sensor attached to the wearable medical device or a medical measurement sensor in communication with the wearable medical device. A calibration coefficient can be determined for calibrating the wearable medical device based on the medical measurement data. The wearable medical device can be calibrated based on the calibration coefficient.

19 Claims, 75 Drawing Sheets

CALIBRATION OF A WEARABLE MEDICAL DEVICE

BACKGROUND OF THE INVENTION

While providing medical care and treatment, doctors often screen, monitor, and diagnose certain physiological events of their patients. Accordingly, a wide variety of physiological screen, monitor, and diagnosis devices have been developed to improve patient care. The physiological medical devices provide healthcare personnel and patients with physiological information to more accurately screen, monitor, and diagnose medical conditions. As a result, physiological medical devices have become an indispensable part of modern medicine.

One example of a physiological medical devices used by doctors is a pulse oximeter. Pulse oximetry may be used to measure various blood characteristics, such as the arterial blood oxygen saturation of hemoglobin (SP02) or the rate of blood pulsations corresponding to each heartbeat of an individual. Continuously monitor a patient's physiological condition, such as pneumonia, can require monitoring a patient's heart rate, breathing rate, temperature, and oxygen levels. Continuously monitoring a patient's physiological condition usually requires hospitalization of the patient, which can be both costly and time consuming, especially where long term monitoring can be required. In addition to often requiring hospitalization, continuously monitor a patient can often require the patient be bed ridden or significantly reducing a patient's mobility, i.e. a non-ambulatory patient. Recently, wearable medical devices have begun to be developed and used to allow a patient to leave a medical facility while still being monitored. Accurate medical monitoring using wearable medical devices can be difficult as a patient's physiology and the environment that the patient is monitored in can change over time.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein.

Figure 1:
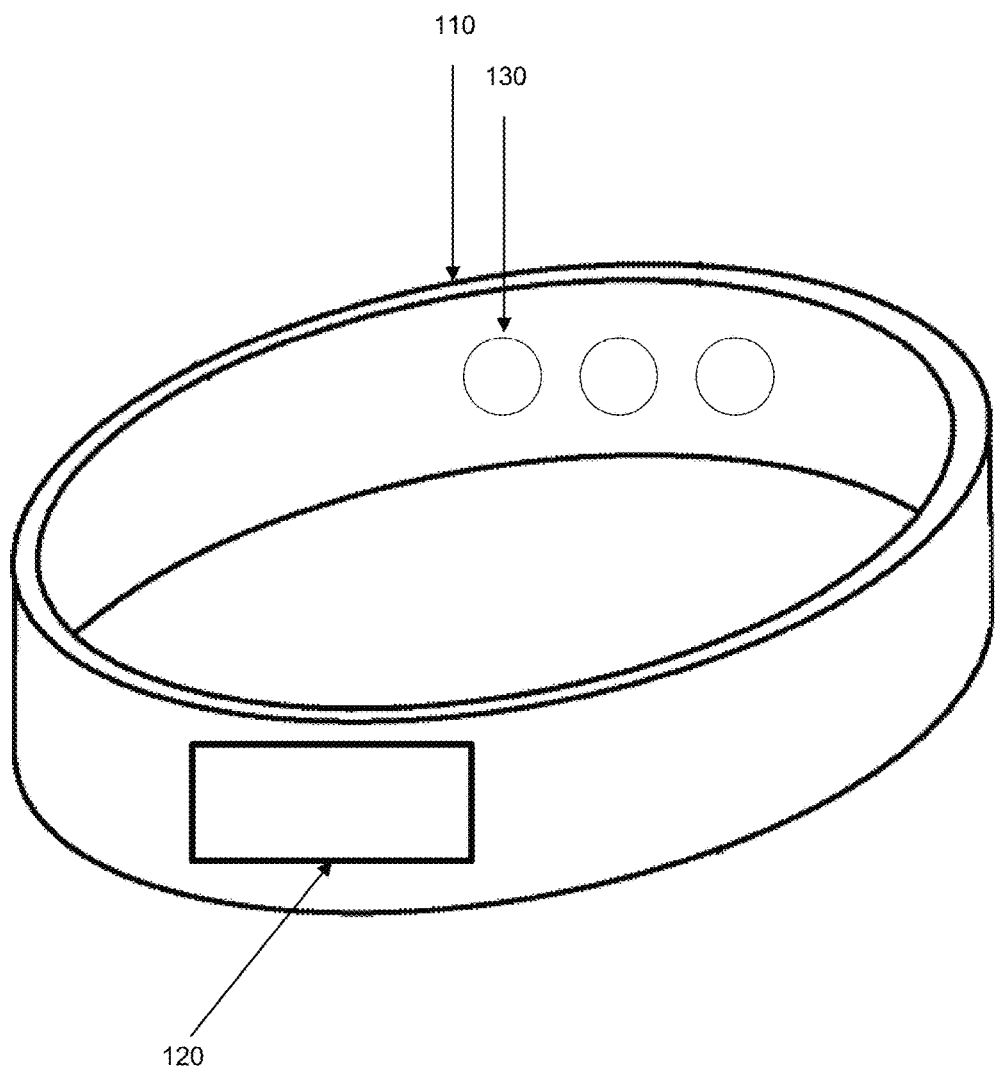
FIG. 1 depicts a wearable medical device in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Chronic medical conditions are a major health concern worldwide. Chronic infirmities and diseases consume the majority of healthcare expenditures as treatment for chronic infirmities and diseases can be for an open-ended or indefinite duration of time. For example, congestive heart failure (CHF) is a progressive disease with varying symptoms such as fatigue, shortness of breath, fluid retention, swelling in the abdomen or legs, lung congestion, and cardiac arrhythmias. CHF can be treated, and its symptoms mitigated, by lifestyle modifications and constant monitoring of a patient. However, monitoring CHF can be time intensive and difficult.

Accordingly, CHF continues to reduce the quality of life and life expectancy of CHF patients.

Many chronic medical conditions are traditionally monitored on a periodic or sporadic basis, i.e. not monitored on a continuous or semi-continuous basis. For example, blood pressure measurements, body temperature measurements, hydration, and other measurements are only measured and collected at prescribed intervals.

Wearable medical devices can be used to enable constant, continuous, semi-continuous, or periodic monitoring of medical conditions, such as CHF, and decrease the difficulty of a patient or medical personnel, such as a caregiver, in monitoring a medical condition. Wearable medical devices can enable patient monitoring that can be constant, non-invasive, transparent, and/or non-intrusive into the patient's life. For example, wrist-worn devices have been developed to record a patient's physiological data, such as a patient's heart rate, level of activity, etc.

Medical patients can often be mobile, i.e. moving around, while wearing a medical device. Additionally, a patient or user can move, shift, or remove a wearable medical device for certain occasions, such as showering, or during normal use of the medical device. Traditionally, movement of a wearable medical device and taking the wearable medical device on and off can reduce or limit the accuracy of physiological information from wearable medical devices. Accurate medical monitoring can also be difficult where a patient's physiology can change over time, the environment that the wearable medical device can be used in may change or vary, the wearable medical device can lose calibration, and so forth.

As the environment that the wearable medical device can be used in changes and as variations occur in a patient's physiology, providing accurate readings for a desired physiological condition or monitor selected medical measurements over a selected period of time, such as hours, days, or weeks can become increasingly difficult. In one embodiment, the wearable medical device can measure selected physiological measurements while filtering out other physiological measurements that can interfere with the selected physiological measurements. For example, the wearable medical device can measure a heart rate, a hydration level, and a blood oxygen level of an individual while filtering out physiological effects due to medication, dietary changes, and so forth. In another embodiment, movement artifacts, environmental interference, and so forth, can adversely affect the calibration and reliability of the data generated by the wearable medical device when not properly accounted for and/or calibrated for.

FIG. 1 shows one exemplary embodiment of the wearable medical device. FIG. 1 illustrates that the wearable medical device 110 can be a wearable band, such as a wristband, headband, armband, chest band, leg band, or band attached to an individual at a selected location. The wearable medical device 110 can include a display 120 to show information to a user or a third party. The wearable medical device 110 can also include one or more integrated or attached sensors 130, as discussed in the proceeding paragraphs.

The sensors or measurement data of the wearable medical device can be adjusted, calibrated, and recalibrated to increase the accuracy and reliability of wearable medical device. For example, physiological measurements and medical measurements taken by sensors attached to or integrated into the wearable medical device can be adjusted, calibrated, and recalibrated. Additionally, the medical measurements taken by the wearable medical device can be analyzed, filtered, adjusted, and so forth, to increase the accuracy and reliability of the physiological measurements and medical measurements of the wearable medical device. There are several techniques for calibrating wearable medical devices and analyzing the medical measurement data. In one embodiment, the calibration techniques discussed in the proceeding paragraphs can be applied to calibrating one or more sensors of the wearable medical device or separate device and/or measurement data taken by the one or more sensors of the wearable medical device or separate device. In another embodiment, the calibration techniques discussed in the proceeding paragraphs can be applied before one or more measurements are taken by the one or more sensors (e.g. apriori), real time (e.g. while the one or more sensors are taking one or more measurements), or after the measurement are taken by the one or more sensors (e.g. post measurement activity calibration).

Figure 2:
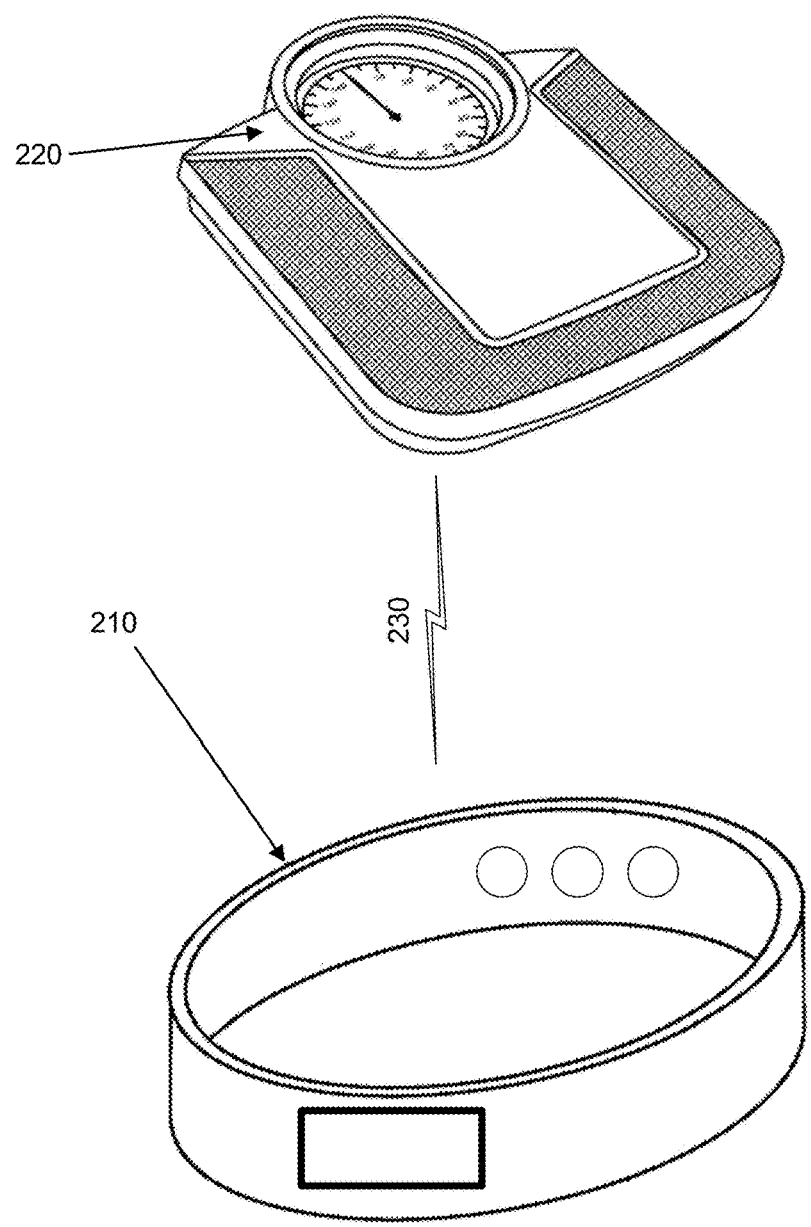
FIG. 2 depicts a wearable medical device and a separate device in accordance with an example.

One technique for calibrating the wearable medical device can be to use a device separate or independent for the wearable medical device to take physiological measurements. FIG. 2 shows a wearable medical device 210 and a separate device 220. FIG. 2 further illustrates that the wearable medical device 210 can be in communication with the separate device 220, using a communication network 230 In another embodiment, the communications network can be a cellular network that may be a 3GPP LTE Rel. 8, 9, 10, 11, or 12 or IEEE 802.16p, 802.16n, 802.16m-2011, 802.16h-2010, 802.16j-2009, 802.16-2009. In another embodiment, communications network can be a wireless network (such as a wireless fidelity network (Wi-Fi) that may follow a standard such as the Institute of Electronics and Electrical Engineers (IEEE) 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a Zigbee connection such as IEEE 802.15.4-2003 (Zigbee 2003), IEEE 802.15.4-2006 (Zigbee 2006), IEEE 802.15.4-2007 (Zigbee Pro). In one embodiment, the separate device 220 can be another wearable medical device separate from the wearable medical device 210. In another embodiment, the separate device 220 can be a device unattached to the user.

The physiological measurements taken by the separate device 220 can be used to set a baseline or basis for comparison for the physiological measurements of the wearable medical device 210. The baseline physiological measurements taken by the separate device 220 can be used to calibrated and/or recalibrate the wearable medical device 210. In one embodiment, the user can take a baseline measurement for a selected physiological measurement of the user using the separate device 220. In another embodiment, the separate device 220 can automatically take a baseline measurement for a selected physiological measurement of the user. The separate device 220 can communicate the baseline physiological measurement to the wearable medical device 210 and the wearable medical device 210 can use the baseline physiological measurement as a basis for calibrating the wearable medical device 210. In one embodiment, the wearable medical device 210 can use the baseline physiological measurement as a basis for calibrating the wearable medical device 210 for the selected physiological measurement. Physiological measurements can include, measurements of characteristic of the health of an individual, measurements of bodily functions of an individual, chemical balances of an individual, psychological functions of an individual, medical measurements, and so forth.

In one embodiment, the separate device 220 can be used to uniquely calibrate the wearable medical device 210 to each unique user of the wearable medical device 210. For example, the wearable medical device 210 can monitor the hydration status or change in the hydration level of the unique user. As each unique user of the wearable medical device 210 has a different physiology, measuring the baseline physiological measurement from which to measure the user's hydration level is different for each unique user. The separate device 220 can be used to characterize a user signature, e.g. a unique identifier of the user, and calibrate one or more sensors 240 of the wearable medical device for each unique user based on the baseline measurements of the separate device 220. In one embodiment, the separate device 220 can be a urinalysis device, a spectrometer, a pulse oximeter, a heart rate monitor, a body weight measurer, a body mass measurer, a blood pressure monitor, a pedometer, an implantable device, an electrocardiogram (EKG) device, and so forth.

For example, the physiology of a teenage girl can be different from the physiology of an elderly man. These physiological differences can include general health, weight, percent body fat, metabolic rates, age, sex, general health, average level of activity, race, genetic predispositions, and so forth. Accordingly, to more accurately monitor the hydration level of the teenage girl or the elderly man, the wearable medical device can be calibrated to each individual. In one embodiment, a baseline calibration from which relative physiological measurements can be made can be set or established for each user, such as the hydration level of the individual. For example, a body mass measuring device can measure the body mass of the individual and the body mass can be used to calibrate the wearable medical device for monitoring the hydration level of the individual wearing the wearable medical device. In one embodiment, the body mass measurer can be a body weight scale or a bathroom scale that measures the weight of the individual. The height of the individual can be measured or input and the body mass measurer can convert the weight and height of the individual into a body mass index. In one embodiment, the body mass of an individual can be monitored over a selected period of time, such as 3 or 4 days. When the body mass of the individual remains approximately constant over the selected period of time, then the body mass measurement can be used to set a base line for calibrating the wearable medical device.

Figure 3:
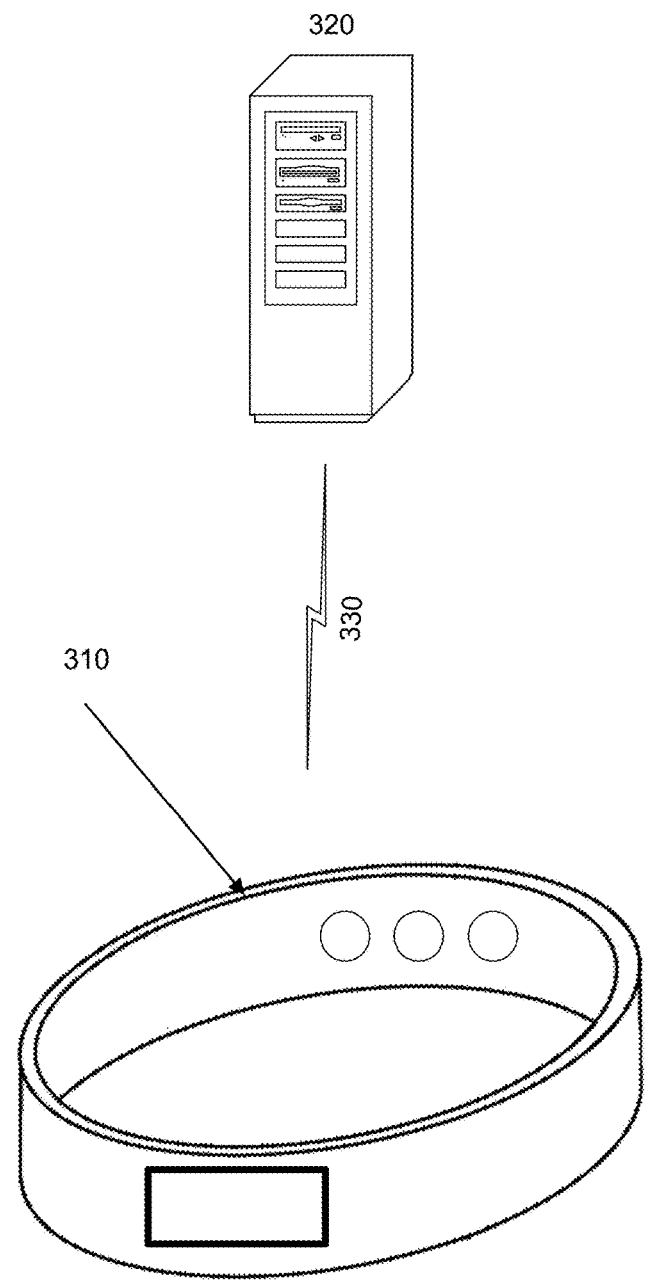
FIG. 3 depicts wearable medical device in direct communications with a computing device in accordance with an example.

FIG. 3 illustrates that the wearable medical device 310 can be in direct communications 330 with an other computing device 320. In one embodiment, the direct communication 330 can be a Bluetooth, Zigbee, radio signal, or other direct communication systems. In one embodiment, the other computing device 320 can be a server that stores information such as previously physiological measurements taken by the wearable medical device 310 or physiological measurements taken from a selected group of individuals, as discussed in the proceeding paragraphs. In another embodiment, the other computing device 320 can be a mobile computer device, such as a laptop computer, tablet, or a smartphone. The wearable medical device 310 can communicate data, such as physiological measurements, to the other computing device 320. In one example, the other computing device 320 can be used to process and/or analyze the data communicated from the wearable medical device 310. In another example, the computing device 320 can communicate the processed data, analyzed data, measurement results, or other information to the wearable medical device 310. In another example, the computing device 320 can communicate calibration information to the wearable medical device 310.

Figure 4:
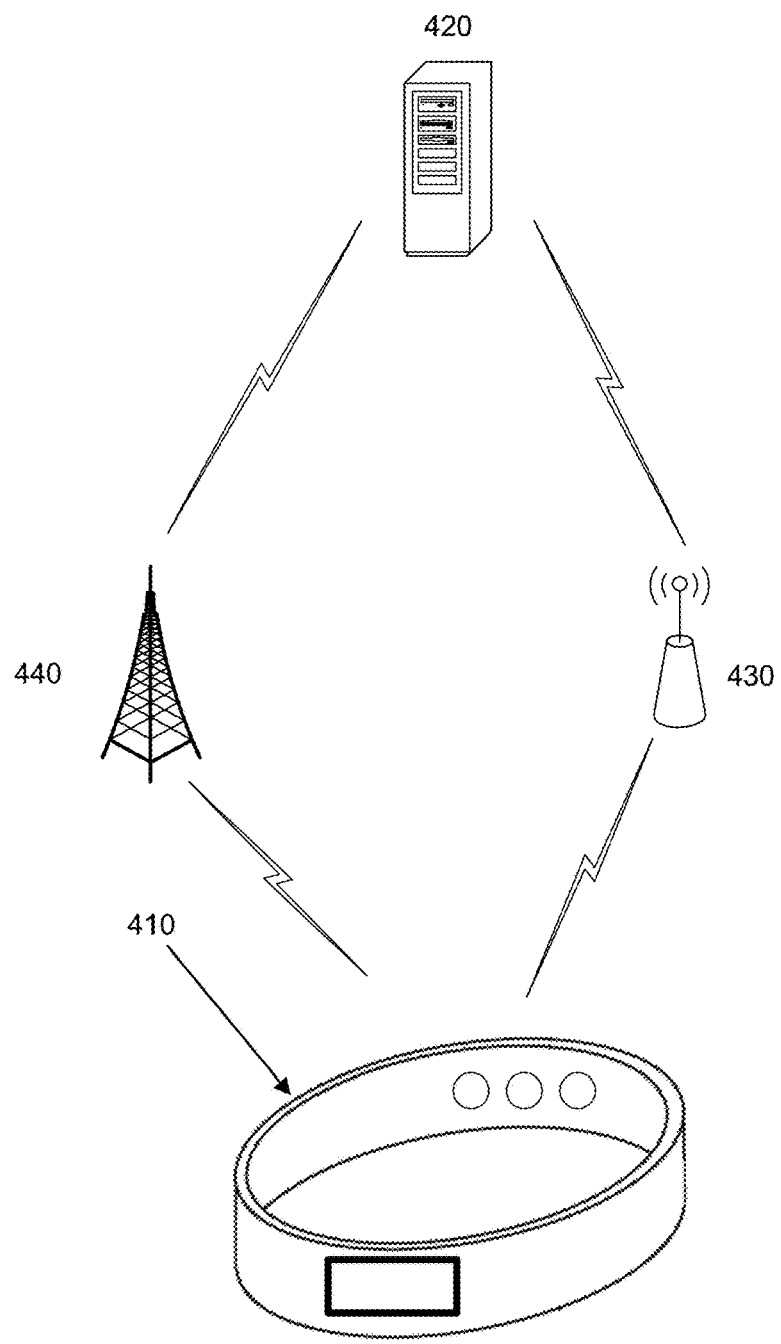
FIG. 4 depicts a wearable medical device and a computing device in indirect communication using a communications network in accordance with an example.

FIG. 4 illustrates that a wearable medical device 410 and a computing device 420 can be in indirect communication using a communications network such as wireless communication network 430, such as a Wi-Fi network, and/or using a cellular communication network 440, such as a 3GPP network, to communicate data or information. In one embodiment, the wearable medical device 410 can take physiological or medical measurements using one or more sensors 450 and communicate the physiological or medical measurement data to the computing device 420 via the wireless communication network 430 and/or the cellular communication network 440. In another example, the computing device 420 can receive physiological or medical measurement data from the wearable medical device 410 via the wireless communication network 430 and/or the cellular communication network 440 and process the data and/or analyze the data. When the computing device 420 has analyzed process the data and/or analyze the data, the computing device can communicate the processed data, analyzed data, measurement results, or other information to the wearable medical device 410 via the wireless communication network 430 and/or the cellular communication network 440.

Figure 5:
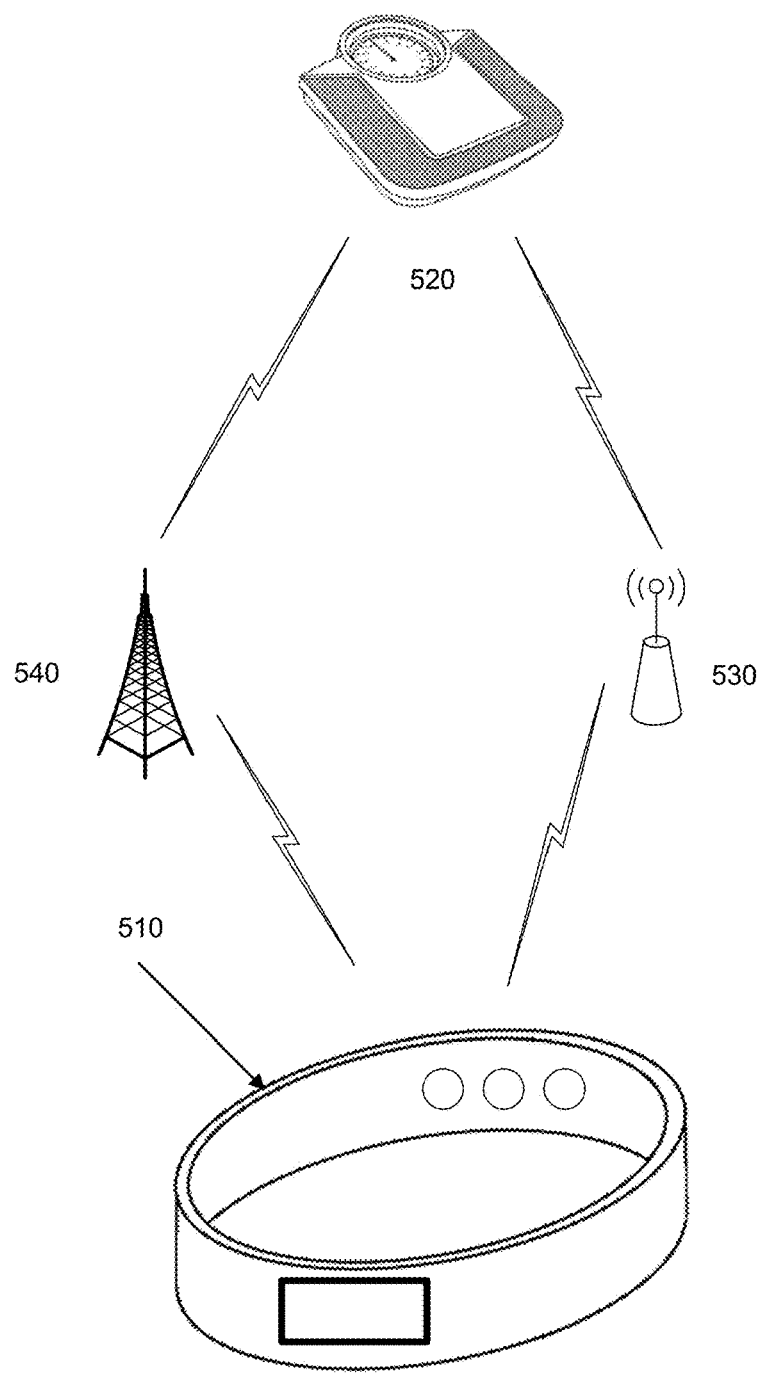
FIG. 5 depicts a wearable medical device and a separate device can be in indirect communication using a communications network in accordance with an example.

FIG. 5 illustrates that a wearable medical device 510 and a separate device 520 can be in indirect communication using a communications network such as wireless communication network 530, such as a Wi-Fi network, and/or using a cellular communication network 540, such as a 3GPP network, to communicate data or information. In one embodiment, the wearable medical device 510 and/or the separate device 520 can take physiological or medical measurements. In one example, the wearable medical device 510 can communicate the physiological or medical measurements to the separate device 520 using the communication network. In one example, the separate device 520 can communicate the physiological or medical measurements to the wearable medical device 510 using the communication network. In one embodiment, the wearable medical device 510 and/or the separate device 520 can use the received physiological or medical measurements to calibrate one or more sensors or measurement data of the wearable medical device 510 or the separate device 520, respectively.

Figure 6:
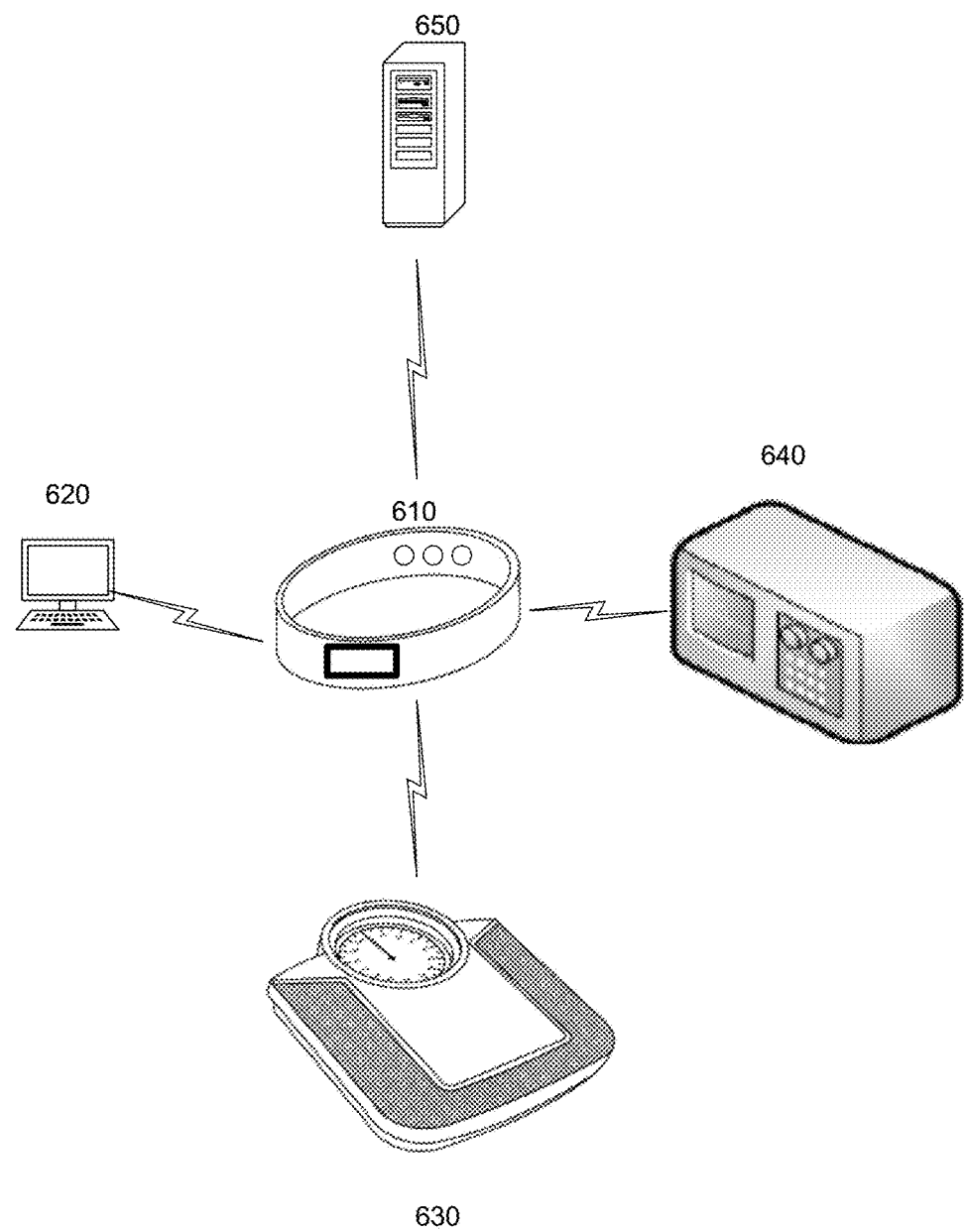
FIG. 6 depicts a wearable medical device in communication with one or more other devices in accordance with an example.

FIG. 6 illustrates that the wearable medical device 610 can be in communication with one or more other devices, such as a computing device 620, a weight scale 630, an electrocardiography (ECG) device 640, and/or a server 650. In one embodiment, the wearable medical device 610 can receive medical or physiological data, user information, and/or measurement information from the one or more other devices 620-650. In one embodiment, the wearable medical device 610 can uses the medical or physiological data, user information, and/or measurement information to calibrate the wearable medical device 610, one or more sensors of the wearable medical device 660, or measurement data of the one or more sensors of the wearable medical device 660. In another embodiment, the wearable medical device 610 can communicate medical or physiological data, user information, and/or measurement information to the one or more other devices 620-650.

Figure 7:
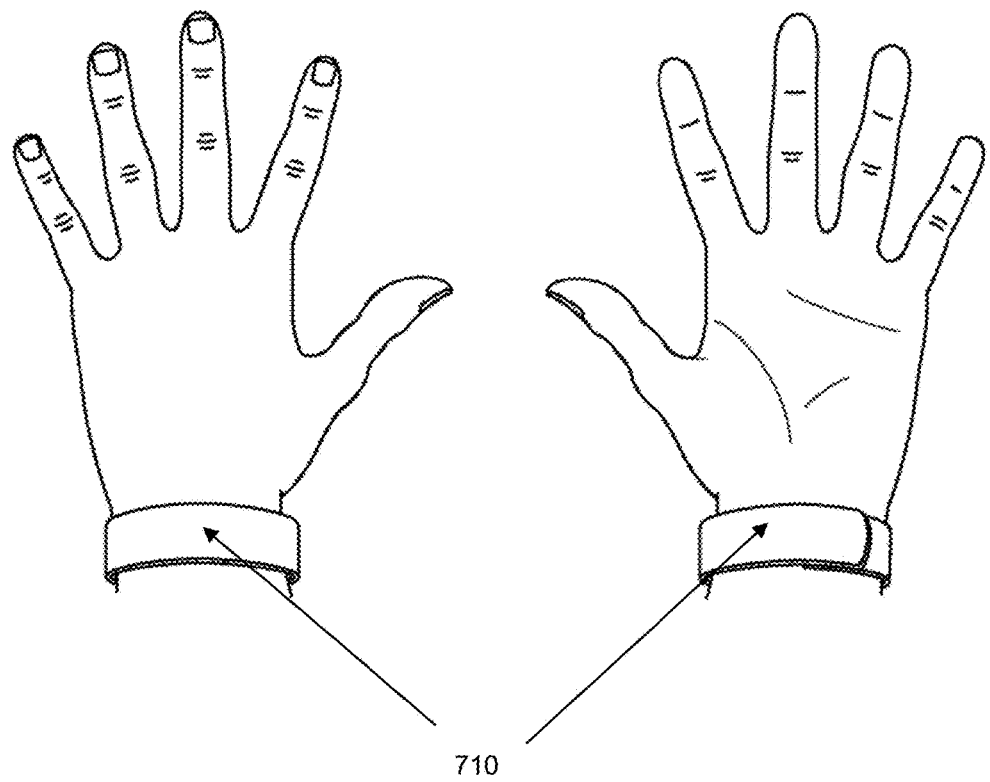
FIG. 7 depicts a wristband wearable medical device attached to the wrist of an individual in accordance with an example.
Figure 8:
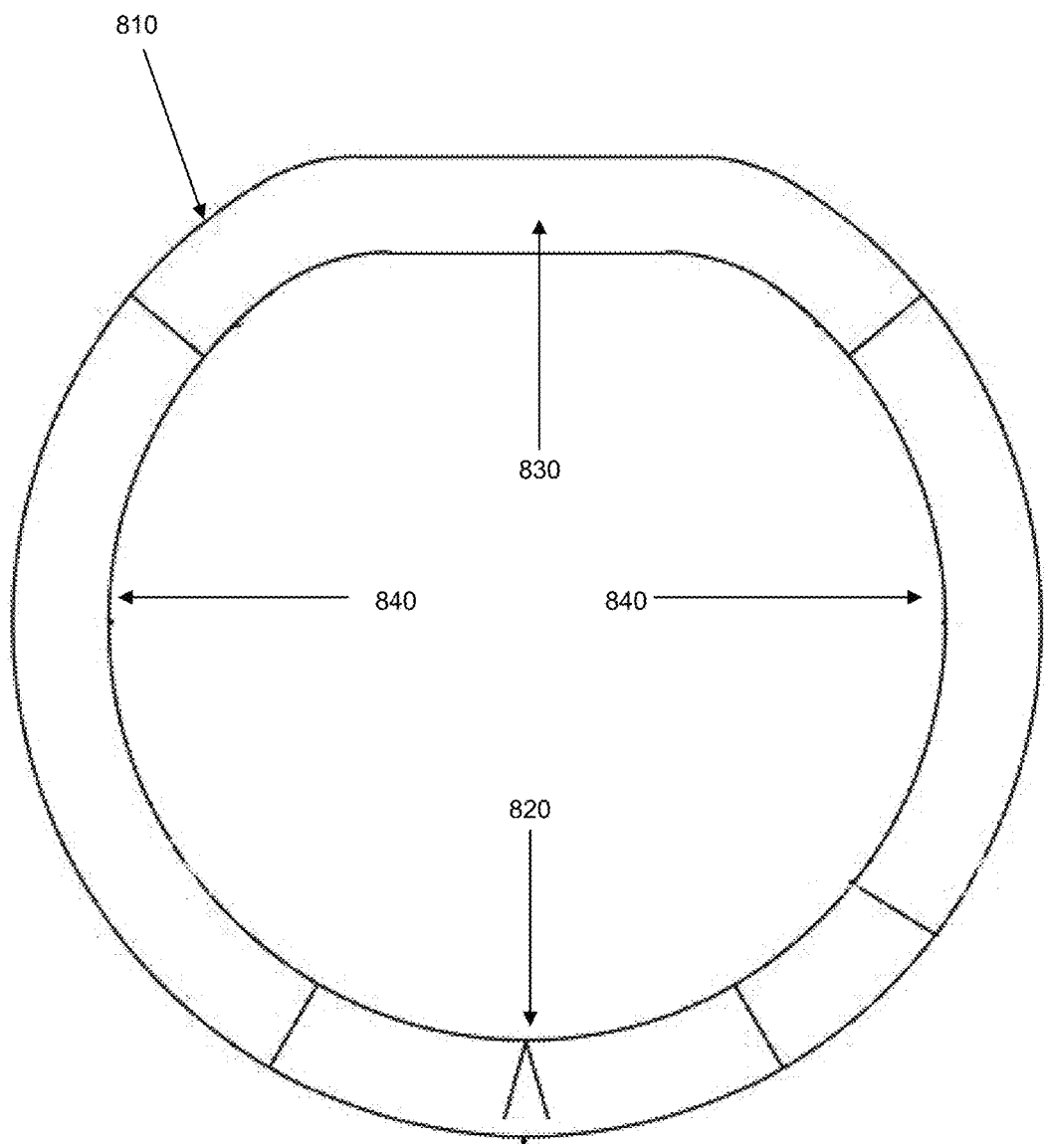
FIG. 8 depicts a side view of a wristband wearable medical device in accordance with an example.

FIG. 7 shows one exemplary embodiment of a wristband wearable medical device 710. The wristband wearable medical device 710 can attach to the wrist of an individual and take one or more medical measurements at the wrist location. In one embodiment, wristband wearable medical device 710 can cover or wrap around the circumference of the wrist of an individual. FIG. 8 shows a side view of a wristband wearable medical device 810, as discussed in FIG. 7. The wristband wearable medical device 810 can have one or more integrated sensors 820. The wristband wearable medical device 810 can have a flat top portion 830 and a circular remaining portion 840 to fit to the contour or shape of a wrist on an individual.

Figure 9A:
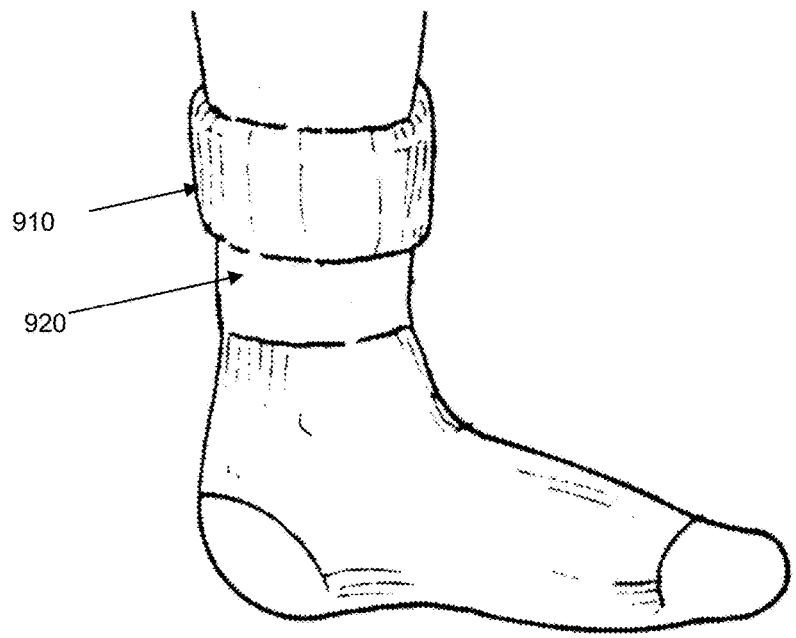
FIG. 9*a* depicts a wearable medical device at the ankle of an individual in accordance with an example.
Figure 9B:
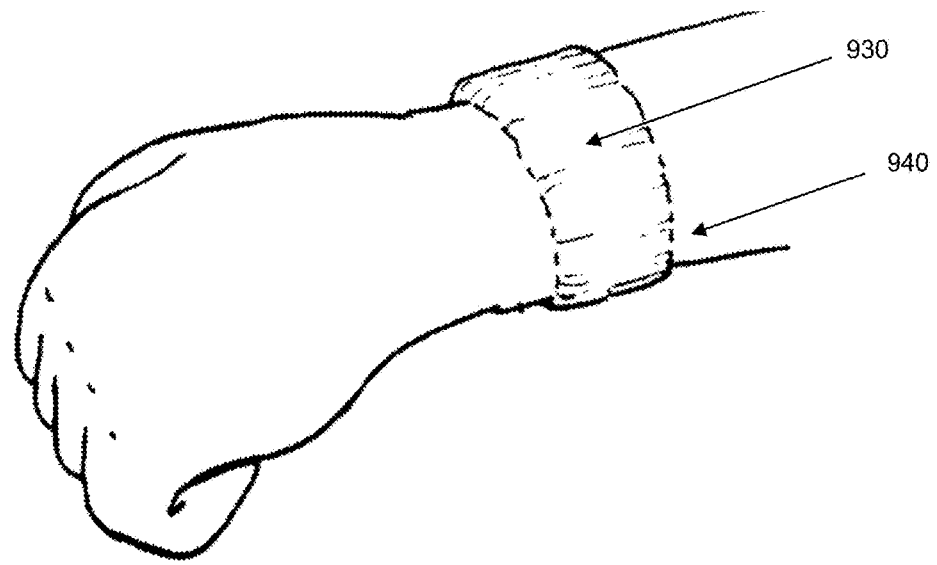
FIG. 9*b* depicts a wearable medical device at the wrist of an individual in accordance with an example.
Figure 10:
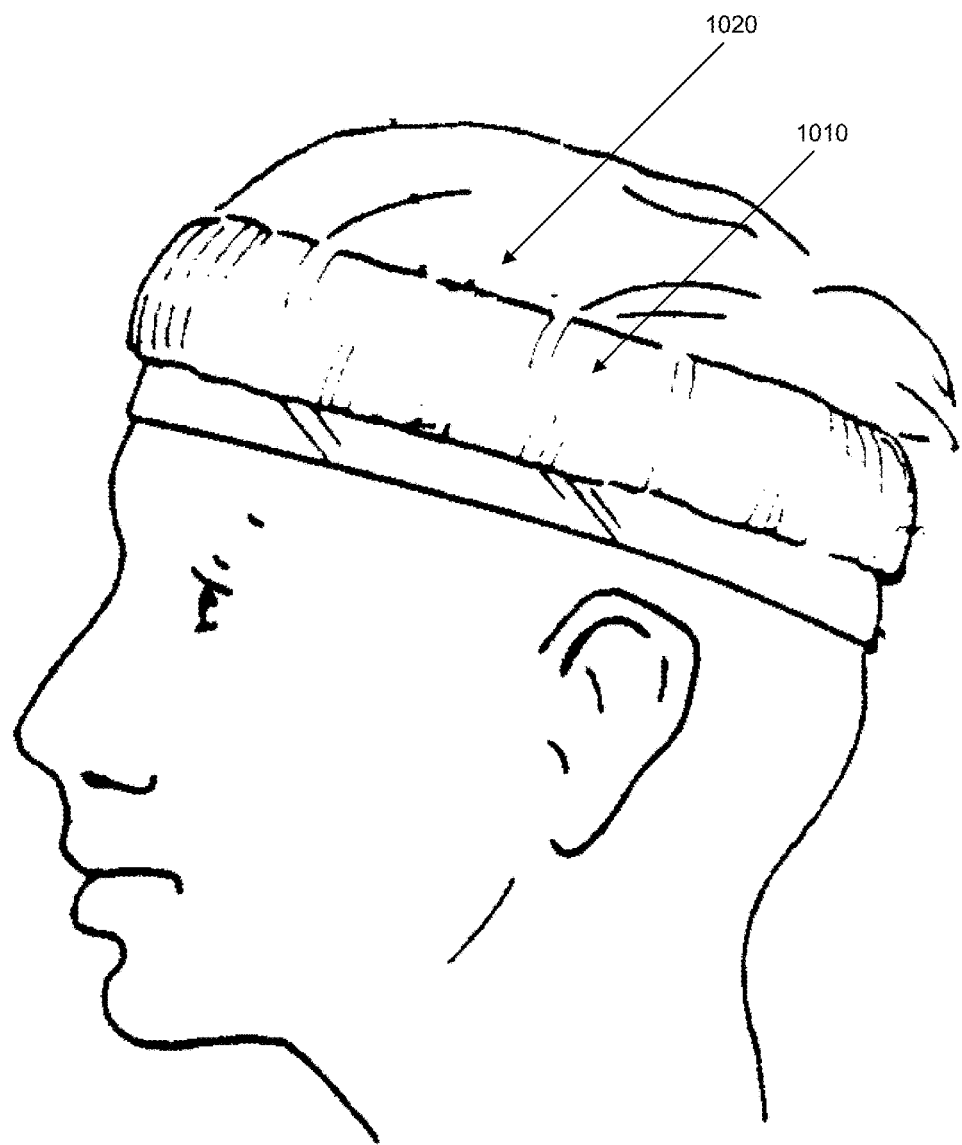
FIG. 10 depicts a wearable medical device located at the forehead of an individual in accordance with an example.

FIGS. 9a and 9b illustrate a wearable medical device 910 located at selected locations on an individual. FIG. 9a illustrates a wearable medical device 910 located at or near the ankle of an individual. FIG. 9b illustrates a wearable medical device 910 located at or near wrist of an individual. FIG. 10 illustrates a wearable medical device 1010 located at a selected location on an individual. FIG. 10 illustrates a wearable medical device 1010 located at or near head or forehead of an individual.

The separate device can be used to recalibrate or check the accuracy of the wearable medical device. For example, the separate device can take continuous or periodic physiological measurements over a selected time period. The physiological measurements taken by the separate device can be compared to measurements taken by the wearable medical device. For example, the body mass measure can monitor the body mass of the user over a defined period of time to determine a consistent body mass of the individual over time or changes in the body mass of the individual of time. The body mass measurements can be correlated with the measurements taken from the individual using the wearable medical device. In one embodiment, the body mass measurements of the individual can signal a physiological change and the wearable medical device can be recalibrated to correlate with the body mass measurements.

In one embodiment, when changes in the physiological measurements are detected in the data taken by the independent medical device, such as changes in the body mass of the individual, the physiological measurement changes can be compared to measurements taken by the wearable medical device. When changes in physiological measurements taken by the independent medical device correlate with the wearable medical device, the wearable medical device can determine that the wearable medical device is taking accurate or correct measurements. In another embodiment, when changes in physiological measurements taken by the separate device do not correlate or are outside a selected correlation range with the measurements taken by the wearable medical device, the wearable medical device can determine that the measurement taken by the wearable medical device are inaccurate or incorrect measurements and the wearable medical device can be recalibrated. In one embodiment, the correlations or cross correlations can provide additional measurement information or calibration information. In one embodiment, the correlations or cross correlations can be used to increase the accuracy of a physiological measurement. For example, the physiological measurement taken by the independent medical device can provide different or separate data points that correlate with other data points take by the wearable medical device. When the data points are correlated between the two devices, the accuracy of the measurement data can be increased because of a larger or more detailed correlated data set.

For example, a sudden increase in the body mass or weight of an individual may signal the retention of water and other bodily fluids. There are several techniques for monitoring an increase or retention of bodily fluid. In one embodiment, an increase or retention of bodily fluid can be monitored by observing a weight lose and/or gain of an individual for a defined or selected period of time. For example, the weight lose and/or gain of the individual can be measured by weighing the individual multiple times for a select period of time, such as the individual weighing himself on a bathroom scale at selected points in time.

In another embodiment, pressure plates can be placed under the legs of a bed or mattress to monitor changes in weight or body mass of the user of the wearable medical device. For example, assuming factors other than the weight of the individual are held constant or filtered out, then the difference between measurements of the empty weight of the bed and measurements of the weight bed with the individual can be monitored to measure the change in the weight or body mass of the user of the wearable medical device. One advantage of using pressure plates to weigh an individual, such as ones placed under the legs of a bed, can be to enable automatic and nonintrusive monitoring of the individual's weight or body mass. Automatic and nonintrusive monitoring of the individual's weight or body mass can eliminate the need for the individual to remember to weigh himself in order to calibrate a wearable medical device. Additionally, using pressure plates to weigh an individual can enable measuring the weight of the individual at approximately the same time each day to reduce the influence of external factors such as weight change before or after the intake of food that can create false positives.

When the wearable medical device does not show a corresponding change in physiological measurement data of the individual, such as the hydration level of an individual, the wearable medical device can be recalibrated to more accurately reflect the change in the body mass of the individual.

In one embodiment, the body mass of an individual can be measured using urine analysis, skin tension, hematocrit (HCT), and so forth. Physiological measurements, such as body mass, can be correlated with other physiological events of the body of an individual, such as water retention, and used to calibrate the wearable medical device for one or more physiological measurements. In one embodiment, a plurality of physiological measurements taken using one or more separate devices and/or sensors of the wearable medical device can be analyzed using multivariant analysis of the plurality of physiological measures to maintain calibration and accuracy of the wearable medical device.

The wearable medical device can monitor the hydration level of an individual using impedance spectroscopy. For example, the wearable medical device can monitor trending of the impedance of an individual's skin or subdermal body location with impedance spectroscopy. One advantage of using non-invasive monitor, such as impedance spectroscopy, in a wearable medical device can be to enable non-invasive monitor of an individual over an extended period of time. Another advantage of using non-invasive monitor, such as impedance spectroscopy, in a wearable medical device can be to enable automatic and nonintrusive taking of physiological measurement from the individual.

In another embodiment, the wearable medical device and/or the separate device can take non-invasive, automatic, continuous, and/or non-intrusive physiological measurements. One advantage of taking non-invasive, automatic, continuous, and/or non-intrusive physiological measurements can be that the user of the wearable medical device and/or the separate device can be unaware or oblivious to the wearable medical device and/or the separate device taking the physiological measurements. For example, the individual can be unaware or oblivious to the wearable medical device and/or the separate device taking the physiological measurements until the wearable medical device alerts the user when selected or defined physiological event occurs.

For example, the wearable medical device can use impedance spectroscopy to take hydration level measurements and monitor the hydration level of the user, receive body mass measurement of the user from a separate device, and recalibrate the wearable medical device based on the hydration level measurements and body mass measurements. Another advantage of non-intrusive and/or automatic medical measurements can be for long term monitoring and/or treatment of patients, where transparent and seamless patient engagement with the wearable medical device can enable the long term care patient to live a life without a constant interruption of inputting information into a device, e.g. the long term care patient can live normally during the treatment period.

In one embodiment, the wearable medical device can continuously monitor the user and alert the user of a medical or physiological condition when it occurs. One advantage of continuously monitoring the user using the wearable medical device can be that the user can receive alerts earlier than a medical device that periodically takes medical measurements, such as an independent or separate device. For patients that require close medical monitoring, such as CHF patients, continuous monitoring and early detection can enable the patient to avoid more serious medical conditions.

The wearable medical device taking continuously or semi-continuously physiological measurements can enable a more detailed trend analysis of the physiological measurements. In one embodiment, trend analysis of physiological measurements can provide different information than a single or distinct physiological measurement. For example, monitoring weight gain or loss trend of an individual can show a sudden or unexpected change in the body weight of the individual. The sudden or unexpected change in the body weight can indicate physiological changes, whereas an absolute or distinct body weight measurement of the individual may not show the sudden or unexpected change in weight. One advantage of using the wearable medical device to monitor trending information can be to collect physiological or medical information and/or measurements that a device that takes absolute or distinct physiological or medical information and/or measurements may not capture.

The measurements taken by the separate device can be aggregated or combined with the measurements taken by the wearable medical device. In one embodiment, the measurements taken by the separate device can be uncorrelated, unrelated, or orthogonal to the measurements taken by the wearable medical device. The unrelated measurements taken by the separate device can be aggregated with the measurements taken by the wearable medical device to provide additional detail of the user's physiological condition. For example, the oxygen level of an individual can be measured by using a separate device and the oxygen level can be unrelated to a hydration level measurement taken by the wearable medical device. In one embodiment, the distinct and unrelated oxygen level measurement and hydration level measurement can be correlated to increase the accuracy of the physiological data provided to the user, patient, or caregiver.

In another embodiment, the unrelated measurements taken by the separate device and the wearable medical device can be associated to the same physiologic or medical condition, such as the hydration level of a patient. The measurement taken by the separate device and the measurement taken by the wearable medical device for the same physiologic condition can then be aggregated or correlated to provide additional detail and accuracy regarding the physiologic condition of the user. For example, the separate device can measure the oxygen level of the user and the wearable medical device can measure the bioimpedance of the user. In this example, while the oxygen level of the user may not affect the bioimpedance of the user, both measurements may be associated with the hydration level of the user and each measurement can be aggregated together to provide a more accurate and detailed data set regarding the user's hydration state. One advantage of aggregating the measurements of the wearable medical device with the measurements of the separate device can be to increase the accuracy of the information and/or calibrate the measurements taken by the separate device and/or the wearable medical device. In another embodiment, multiple measurements, such as measurements taken by the wearable medical device and measurements taken by the separate device, can be analyzed in aggregation to enable additional or differential diagnosis, monitoring, and screen of medical and/or physiological conditions of the user. For example, monitoring a patient's hydration level or state in conjunction with the patient's absolute weight or weight changes can enable a caregiver to differentiate when a weight gain can be caused by water retention or caused by some other issue.

Another technique in calibrating the wearable medical device can be to set or define a threshold value that when exceeded can trigger the calibration of the wearable medical device. In one embodiment, the threshold value can be for a measurement taken by the separate or independent device. In another embodiment, the separate device can be a spectrometer or a specific gravity device used to measure target parameters of the individual, such as specific substances, cells, or properties. In one embodiment, the target parameters can be urine color, specific gravity of the urine, saline content, and so forth. In one embodiment, when a target parameter exceeds a defined threshold the wearable medical device can be calibrated.

In one embodiment, threshold values can be set on the maximum plausible or probable change of a selected physiological parameter within a defined or selected period of time. For example, a rate that cells (i.e. as red blood cells), nerves, tissue, and so forth of an individual's body can regenerate can have specific maximum values. Physiological indicators such as an individual's oxygen saturation level, pulse rate, blood pressure, and so forth can each have specific maximum values. In one embodiment, the distribution of data point collected by the wearable medical device and/or the separate device can be analyzed to determine when a data point or set of data points exceeds or is outside a selected or desired data set distribution.

A selected data point collected by the wearable medical device and/or the separate device can be compared with a continuous or ongoing collection of data points or data sets collected by the wearable medical device and/or the separate device and analyzed to determine when the selected data point exceeds or falls outside a selected threshold or standard deviation, such as 3 standard deviations. In another embodiment, selected data points or data sets can be analyzed to determine when one or more discontinuities in the selected data points or data sets occur or take place. In another embodiment, selected data points or data sets can be analyzed to determine when sudden and/or unexpected reversals or turnarounds in the selected data points or data sets occur or take place.

One or more target parameters for a medical measurement can be compared with data taken by the wearable medical device for the same medical measurement to determine an error rate of the medical measurement taken by the wearable medical device. For example, if a specific gravity device is used on an individual's urine sample to determine that the individual is dehydrated to a defined degree, the same hydration measurement can be taken for the individual using the wearable medical device. In another embodiment, a hydration measurement can be taken by measuring: isotope dilution; bioelectrical impedance; plasma markers, such as osmolality, sodium, total protein, hematocrit, or hemoglobin; hormone concentrations; urine color; changes in body mass; salivary flow or gross, or other physical signs and symptoms of clinical dehydration for the individual.

The difference between the results from a specific gravity device and the wearable medical device can be used by the wearable medical device to determine the error rate or level of the measurements taken by the wearable medical device. In one embodiment, when the error rate of the wearable medical device exceeds a selected or defined threshold, the wearable medical device can be calibrated. In another embodiment, the threshold value can be for a measurement taken by the wearable medical device. When a medical measurement taken by the wearable medical device exceeds a selected threshold value, the wearable medical device can be calibrated. In another embodiment, when the medical measurement taken by the wearable medical device exceeds a selected threshold value, an error can be indicated to the user and/or a third party signaling that the wearable medical device may not be functioning properly and/or the wearable medical device should be checked to verify the wearable medical device functioning properly.

Another technique for calibrating the wearable medical device can be to use a selected or defined sensor integrated into the wearable medical device or internal to the wearable medical device, e.g. a sensor built into the wearable medical device. The integrated or internal sensor can be used to set a baseline from which to calibrate and/or recalibrate the wearable medical device and/or other selected sensors of the wearable medical device.

In one embodiment, the internal sensor can be a plethysmograph. A plethysmograph can be an instrument for measuring changes in volume within an organ. The plethysmograph can attach to an arm, leg or other extremity of the individual and be used to determine circulatory capacity. The wearable medical device can attach around the circumference of a body part of the individual, such as a wristband around the wrist of an individual. In one embodiment, the internal sensor can be an air plethysmograph, wherein the air plethysmograph can be an air-filled cuff used to measure the change in circumference of the organ of an individual. The air plethysmograph can measure and/or monitor a complete circumference or partial circumference of the body part of the individual where the air plethysmograph is located.

A change in the circumference can indicate a change in a physiological state of the individual. For example, when the circumference of the body part of the individual increases, the increase in circumference can indicate an increase in the fluid level or swelling of an organ of the individual and/or an increase in the fluid level or swelling of the individual overall. When the circumference of the individual's body part decreases, the decrease may indicate a decrease in the fluid level of an organ of the individual and/or an decrease in the fluid level of the individual overall. Sudden increases and decreases in the circumferential measurements can be seen in the circumference measurements of dialysis patients.

In another embodiment, the internal sensor can be a non-invasive impedance plethysmograph (IPG). The non-invasive IPG can detect venous thrombosis for a selected area of the body of an individual. The IPG can measure small changes in electrical resistance of selected areas of the body, such as the chest, calf, or wrist. In one example, the electrical resistance measurements can reflect blood volume changes and can indicate the presence or absence of venous thrombosis.

In another embodiment, a hematocrit of an individual can be taken using an internal sensor of the wearable medical device and can be used to calibrate the wearable medical device or a selected sensor of the wearable medical device. The hematocrit can be a volume percentage of red blood cells in the blood of the individual. In one embodiment, an ultrasonic sensor can measure the hematocrit of the individual by monitoring changes in an ultrasound wave velocity propagation in plasma as a function of the red blood cell concentration. In another embodiment, a Doppler ultrasound measurement can be used to measure the hematocrit of the individual. In another embodiment, an interferometer can be used to measure the hematocrit of the individual. In another embodiment, a spectrometer can be used to measure the hematocrit of the individual.

In one embodiment, the wearable medical monitoring device can use measurements from the internal sensor of the wearable medical device to calibrate the wearable medical device or selected sensors of the wearable medical device. In another embodiment, the wearable medical device can aggregate a measurement from the internal sensor with other measurements taken by the wearable medical device to provide additional detail and accuracy for medical measurement information.

Another technique to calibrate the wearable medical device can be to use measurement information from a plurality of sensors, such as a sensor array. The sensor array can include an oxygen saturation sensor, a temperature sensor, an accelerometer, a gyroscope, a plethysmograph sensor, an internal calibration sensor, and so forth. In one embodiment, the wearable medical monitoring device can collect measurement information from the plurality of sensors in the sensor array and perform a multivariate analysis (MVA) to calibrate the wearable device. MVA can be used to analyze more than one variable at a time and can be performed across multiple dimensions while taking into account the effects of more than one variable of interest. In another embodiment, a Monte Carlo simulation can be used to analyze measurements from the plurality of sensors or sensor array and calibrate the wearable medical device.

MVA can be performed on measurements taken by one or more sensors of the wearable medical device or sensor array and one or more sensors of a separate device. In one embodiment, the MVA can be performed sequentially on the measurements taken by the wearable medical device and the measurements taken by the separate device. In another embodiment, MVA can be simultaneously performed on the measurements taken by the wearable medical device and the measurements taken by the separate device.

A regression analysis, such as a partial least square (PLS) analysis, can be used to calibrate the wearable medical device. The regression analysis can predict a continuous dependent variable from a plurality of independent variables. In one embodiment, the dependent variable can be a dichotomous and a logistic regression can be used to calibrate the wearable medical device. The plurality of independent variables used in the regression can be either continuous or dichotomous. In another embodiment, linear regression can be used to calibrate the wearable medical device. In another embodiment, non-linear regression can be used to calibrate the wearable medical device.

The wearable medical device can filter the measurement data or information collected from one or more of the sensors, such as sensors in the sensor array, of the wearable medical device. For example, a spectral sensor can be used to collect data or information. The spectral sensor can emit multiple wavelengths or frequencies of light and the wearable medical device can filter out undesirable or selected frequencies or wavelengths so that only desirable or selected frequencies or wavelength remain to be analyzed. In one embodiment, an outlying or erroneous measurement, such as an extreme value or a value that significantly deviates from a data set, can be filtered out or excluded from the measurement information used to calibrate the wearable medical device. When measurement data from a sensor of the wearable medical device or a separate device exceeds a defined threshold value for the measurement data, the measurement data can be excluded from data used to calibrate the wearable medical device.

In another embodiment, when the measurement from the sensor of the wearable medical device or the separate device exceeds a defined threshold value for the measurement data, the measurement data from the sensor of the wearable medical device or the separate device can be excluded from the measurement data used to determine physiological measurements. In another embodiment, when the measurement from the sensor of the wearable medical device or the separate device exceeds a defined range for the measurement data, the measurement data from the sensor of the wearable medical device or the separate device can be excluded from data used to calibrate the wearable medical device and from the measurement data used to determine physiological measurements.

Another calibration technique can be to use a learning algorithm or smart algorithm to calibrate the wearable medical device. In one embodiment, the learning algorithm or smart algorithm can use data from a plurality of individuals to calibrate the wearable medical device. For example, measurement data can be collected from a plurality of individuals (group data), where the plurality of individuals can have similar selected criteria or characteristics such as age, weight, fitness level, gender, ethnicity, and so forth. The group data can be analyzed to determine a calibration coefficient to calibrate the wearable medical device for the individual using the wearable medical.

A histogram based on the group data for the user of the wearable medical device can be used to determine the appropriate calibration coefficient. For example, an individual can input defined user information, such as the age, weight, fitness level, and gender of the user and the wearable medical device can select the appropriate group data based on the inputted user information to calibrate the wearable medical device. In one embodiment, the wearable medical device can recursively or iteratively analyzed the data until the data reaches a stable state. In one embodiment, a stable state for the data can be when the accuracy range or error rate reaches a selected threshold or threshold range. For example, the wearable medical device can iteratively calibrate and recalibrate a sensor of the wearable medical device and/or the data from a sensor of the wearable medical device until the sensor provides measurements within a selected threshold range and/or the data from a sensor is within a selected threshold range. In another embodiment, the wearable medical device can iteratively calibrate and recalibrate a sensor of the wearable medical device and/or the data from a sensor of the wearable medical device for a selected period of time and/or for a selected number of cycles. In one embodiment, the wearable medical device can use recursively or iteratively, such as a smart algorithm or learning algorithm, to analyze a physiological or medical measurement or data set until reaching a stable state. In one embodiment, recursion can be a process whereby a solution of a calculation determined through an algorithm, such as a solution determined by the wearable medical device using the smart algorithm or learning algorithm, is fed back into the algorithm and recalculated, wherein the recursive analysis can repeated until the algorithm reaches a stable state. In one embodiment, a stable state can be based on an optimal or efficient solution for the calibration of the wearable medical device.

Another technique for calibrating the wearable medical device can be to account for or compensate for the movement of the wearable medical device. In one embodiment, when the wearable medical device determines there has been a sudden movement of the wearable medical device or discontinuity of measurement data, the wearable medical device may recalibrate the wearable medical device. In another embodiment, when the wearable medical device determines there has been a sudden movement of the wearable medical device, the wearable medical device can set a new baseline that one or more sensors of the wearable medical device measure from. In another embodiment, when the wearable medical device determines there has been a sudden movement of the wearable medical device, the wearable medical device can set a new baseline that the wearable medical can use to analyze measurement data from one or more sensors of the wearable medical device. A sudden movement of the wearable medical device can be indicated in the data by a discontinuity, break, or gap in a continuous data set or semi-continuous data set taken using one or more sensors of the wearable medical device. In one embodiment, the baseline value is readjusted to remove a discontinuity, such as a discontinuity in measurement data, a discontinuity in sensor measurements, a discontinuity in sensor location, and so forth.

In one embodiment, the wearable medical device can detect a sudden movement of the wearable medical device and indicate to the user that the wearable medical device needs to be relocated back to the defined location in order to continue monitoring the individual. In another embodiment, the wearable medical device can determine a defined or selected value to offset a data set from one or more of the sensors of the wearable medical device based on a new or different location of the wearable medical device on the individual, such as a new location of the wearable medical device cause by the movement of the wearable medical device.

Figure 11:
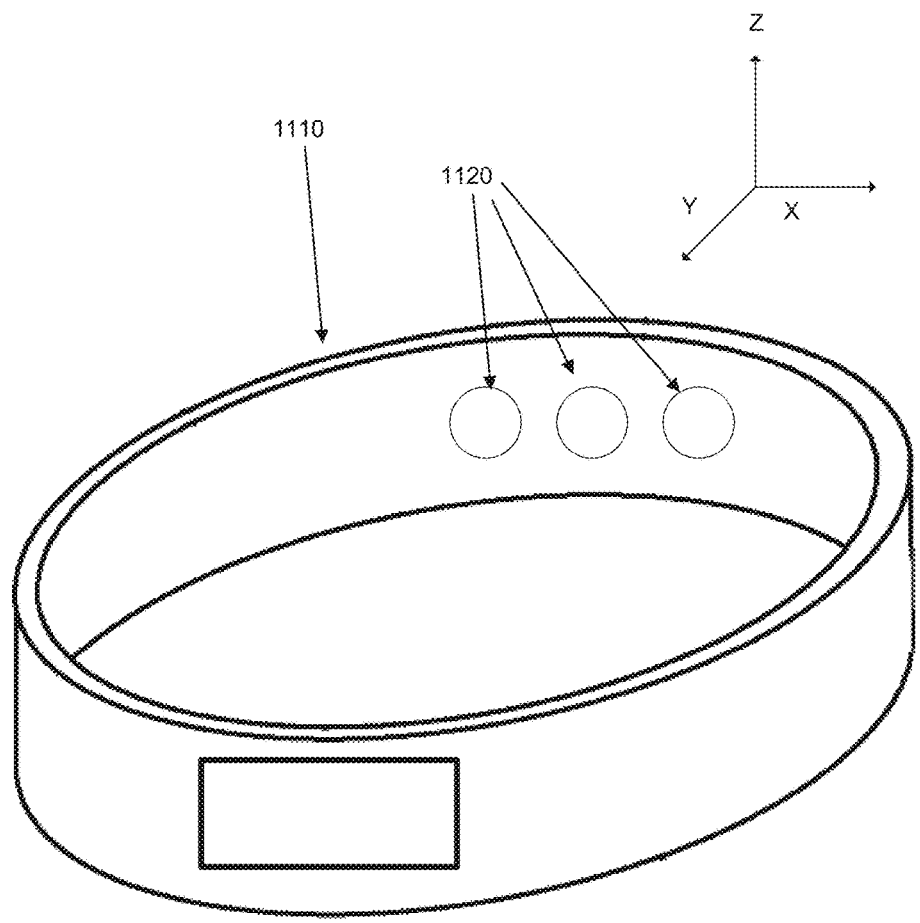
FIG. 11 depicts a wearable medical device with sensors in accordance with an example.

FIG. 11 illustrates a wearable medical device 1110 with one or more sensors 1120, such as a accelerometer, 3d accelerometer, or gyroscope, to determine if there has been an abrupt or sudden acceleration or deceleration, and/or a sudden or abrupt movement of the wearable medical device that may have caused the wearable medical device to move locations on the user. The one or more sensor 1120 can detect movement of the wearable medical device 1110 in the x-axis direction, y-axis direction, and/or the z-axis direction. In one embodiment, a sudden or abrupt movement of the wearable medical device 1110 detected by the one or more sensors 1120 can be a shift, gap, or jump in movement data. For example if one of the sensors 1120 previously measured a zero or substantially minimal movement in the x-axis direction and then measures a substantial increase in movement in the x-axis direction, the substantial increase of movement in the x-axis direction can indicate a move of locations of the wearable medical device 1110 on the user.

In another embodiment, the wearable medical device can include a light sensor or optical sensor to determine if the wearable medical device has moved locations on the user. For example, the optical sensor of the wearable medical device can shine a light onto the skin of the user and the wearable medical device can have a light receiver to detect reflected light from the skin of the user. When the light receiver detects a sudden change in the reflected light from the skin of the user, the sudden change in the reflected light can indicate that the wearable medical device has moved or shifted. In another embodiment, the wearable medical device can include one or more sensors to monitor external environmental conditions and/or changes in external environmental conditions, such as temperature, humidity, light, and so forth. The wearable medical device can determine the effects of the external environmental conditions and/or changes in external environmental conditions and adjust or correct shifts in measurements by one or more sensors of the wearable medical device.

The wearable medical device can use historical trending data or information from one or more sensors of the wearable medical device and/or a separate device to calibrate the wearable medical device. In one embodiment, the wearable medical device can record and/or store previous measurement data of the individual taken by one or more sensors of the wearable medical device and/or the separate device. The wearable medical device can analyze the historical data to determine when the current measurement data is likely correct or probable for the user. In one embodiment, the current measurement data can be likely correct or probable for the user when the current measurement data is in a selected range. The selected range can be a range of the historical data, such as a minimum and maximum data range values of the historical data for a selected sensor of the wearable medical device or a selected physiological measurement.

In one embodiment, historical trending data can be weighted based on the period of time between when a measurement was taken to get the data and the present time. In one embodiment, the earlier or older a data point or data set is from the present time, the less weight or effect is has on the historical trending data. In another embodiment, the newer or fresher a data point or data set is to the present time, the higher weight or effect is has on the historical trending data. For example, as a wearable medical device takes physiological measurements for a selected period of time the wearable medical device stores the different physiological measurements. When the wearable medical device analyzes the physiological measurement data, the wearable medical device can place a higher weight value for current measurements and measurement data that was recently taken, and less weight on measurement data that was taken less recently. One advantage or weight the measurement data according to how recently the measurement data was taken can be to accommodate for a change in data measurements over time. For example as an individual use the wearable medical device for a period of time, the environment that the individual is in when the measurements are taken can change over time and/or physiological conditions of the individual can change over time. More recent data can be weight to accommodate for the change in environment and/or for physiological changes of the individual. In one embodiment, the historical trending data can be averaged or compared to other historical trending data or current measurement data and each data set can be given weighting values. In another embodiment, current measurement data can be adjusted or updated base on historical trending data, wherein weighting values can be assigned to different data sets or data points in the historical trending data.

For example, the data range values of the historical data over a selected period of time for the oxygen level of the blood of a user can be a minimum of 90% oxygenation and a maximum of 100% oxygenation. When current measurement data from one or more sensors of the wearable medical device and/or a separate device is within the data range values of the historical data, the wearable medical device can be optimally calibrated. When current measurement data from one or more sensors of the wearable medical device and/or a separate device is not within the data range values of the historical data, the wearable medical device may need to be recalibrated.

When the wearable device is moved or removed from a location on the user and replaced, the wearable medical device can take a measurement using the sensor array and compare the measurement against stored previous measurements or historical data to determine when to calibrate the wearable medical device and/or what calibrations can be made to one or more sensors of the wearable medical device or measurement data from one or more of the sensors of the wearable medical device. For example, when current measurement data is substantially similar to previous measurements or historical data the wearable device may be located in substantially the same location as previously located. In another example, when current measurement data is not substantially similar to previous measurements or historical data the wearable device may be located in a different location than the previous location of the wearable device.

Figure 12:
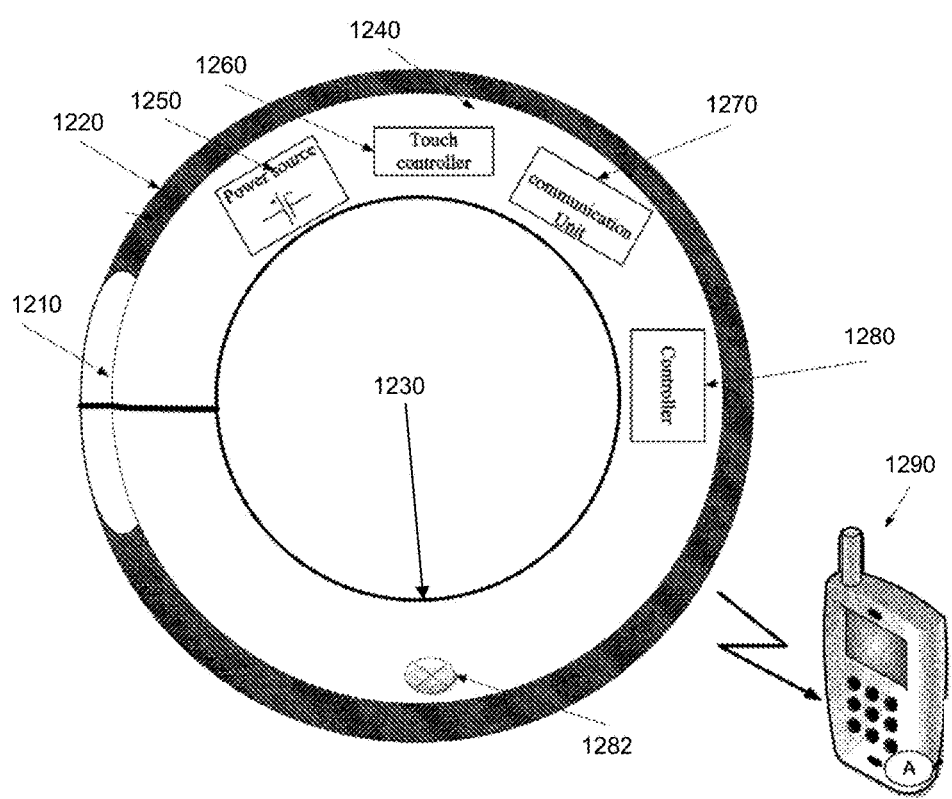
FIG. 12 depicts a wearable medical device in accordance with an example.

FIG. 12 illustrates one exemplary embodiment of a wearable medical device 1210. The wearable medical device 1210 can be a substantially circular band with an outer surface 1220 and an inner surface 1230. In one embodiment, the outer surface 1220 and an inner surface 1230 can be made of flexible or non-rigid material, such as rubber, polyurethane, and so forth. In another embodiment, the outer circumference 1220 and an inner circumference 1230 can be made of semi-rigid or rigid material, such as plastic, metal, and so forth. In one embodiment, a cavity 1240 can be between the outer surface 1220 and an inner surface 1230. The cavity 1240 can include modules, units, systems, subsystems, or devices of the wearable medical device 1210. For example, a power source 1250, a touch controller 1260, a communication unit 1270, a controller 1280, a medical measurement sensor or physiological sensor 1282, and/or other units located in the cavity 1240 of wearable medical device 1210. In one embodiment, the communication unit 1270 can wirelessly communicate with an external computing device 1290. In another embodiment, the power source 1250 can provide power to other units or modules of the wearable medical device 1210.

In another embodiment, the power source 1250 can be a battery, such as a rechargeable battery. The power source 1250 can receive power from another power source such as via a cord plugged into a power source or using wireless power such as inductive wireless charging or resonant wireless charging. In one embodiment, the touch controller 1260 can receive user input from a user of the wearable medical device 1210. In one embodiment, a power source 1250, a touch controller 1260, a communication unit 1270, a controller 1280, a medical measurement sensor or physiological measurement sensor 1282 can be in direct or indirect communication with each other. For example, the touch controller 1260 receive user input information and communicate the user input information to the controller 1280 and the controller 1280 can have a computer processor to analyze or process the user input information. In another example, the physiological measurement sensor 1282 can take a physiological measurement and communicate physiological measurement to the external computing device 1290 via the communication unit 1270.

Figure 13:
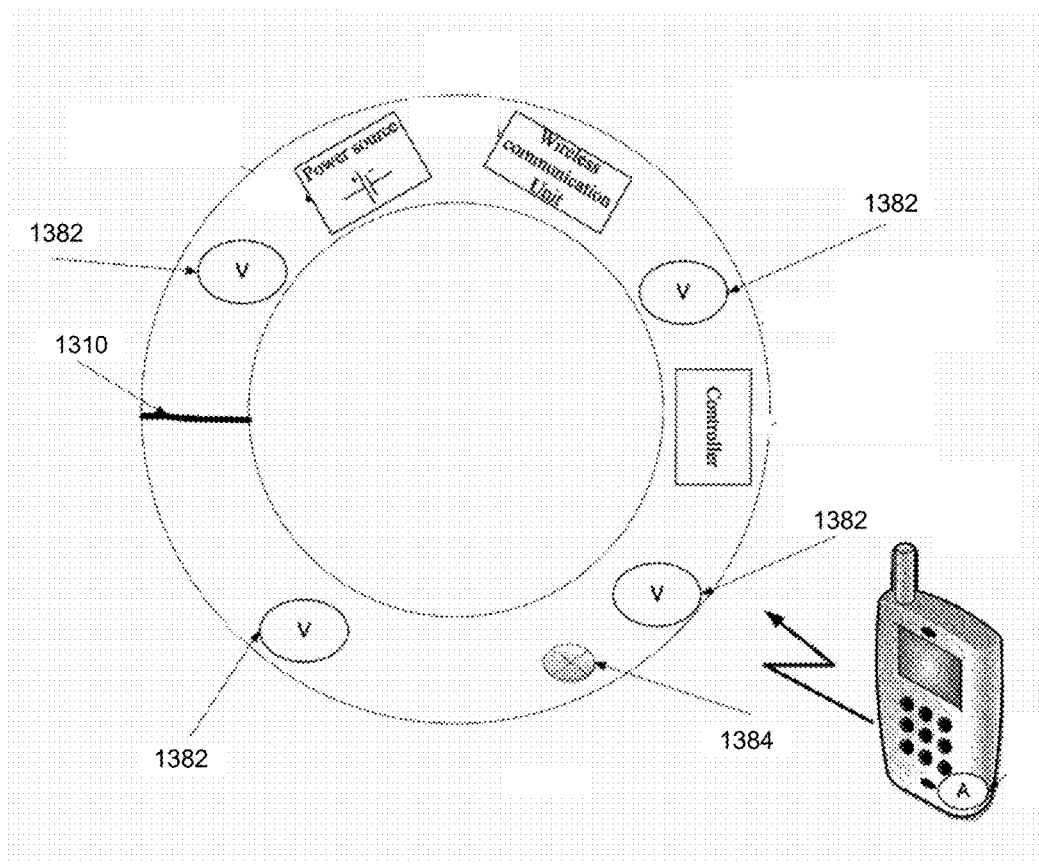
FIG. 13 depicts a wearable medical device with a plurality of medical measurement sensor or physiological measurement sensor in accordance with an example.

FIG. 13 illustrates that a wearable medical device 1310 can have a plurality of medical measurement sensor or physiological measurement sensor 1382 and 1384. In one embodiment, the plurality of medical measurement sensor or physiological measurement sensor 1382 and 1384 can be different types of sensors. The wearable medical device 1310 is substantially similar to the wearable medical device discussed in the preceding paragraphs for FIG. 12.

Figure 14:
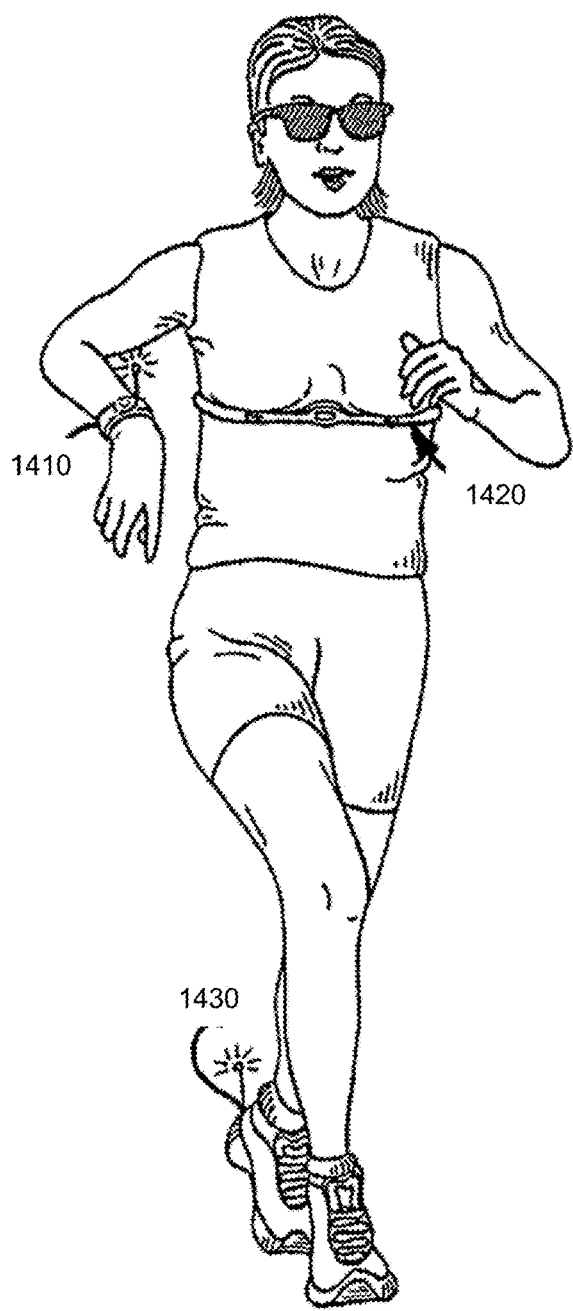
FIG. 14 depicts a wearable medical device that can be in communication with separate device in accordance with an example.

FIG. 14 illustrates a wearable medical device 1410 in communication with separate device 1420. In one embodiment, the separate device 1420 can also be a wearable device. In one example, the separate device 1420 can be a heart rate monitor worn around a chest of an individual. In one embodiment, the wearable medical device 1410 and the separate device 1420 can each take medical measurements and communicate the medical measurement from the wearable medical device 1410 and the separate device 1420 or vise versa. In one example, the separate device 1420 can monitor a heart rate of an individual and communicate the heart rate information to the wearable medical device 1410. In another embodiment, the wearable medical device 1410 can be in communication with a plurality of devices, such as separate devices 1420 and 1430. In one embodiment, separate device 1430 can be a movement sensor, such as an accelerometer that is attached to or built into a shoe.

Figure 15:
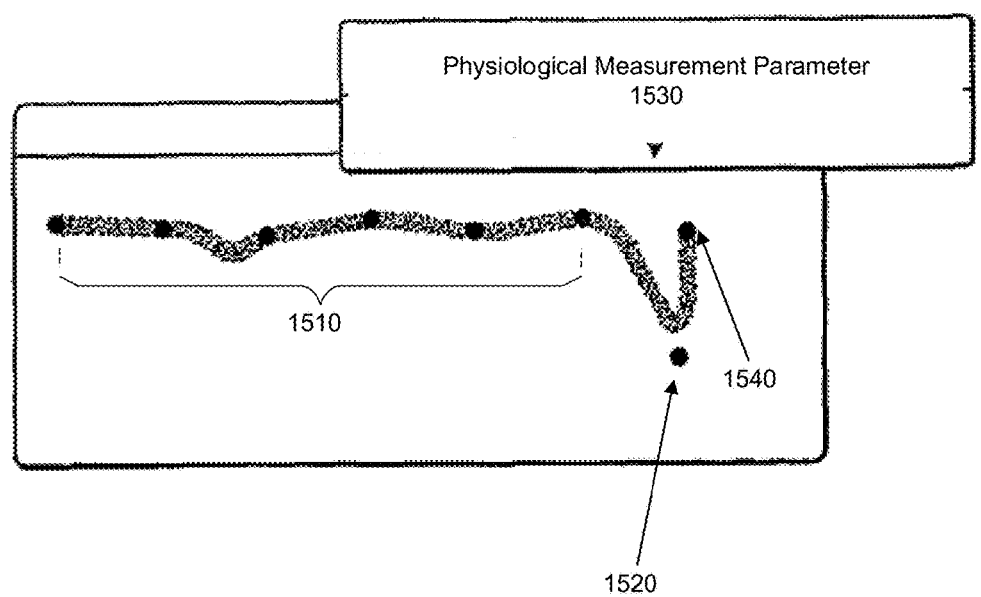
FIG. 15 depicts a wearable medical device forecasting the future of selected physiological data in accordance with an example.

FIG. 15 illustrates that a wearable medical device can perform future forecasting of selected physiological data 1530 based on a selected historical trending of measurement data 1510 and/or current trending of measurement data 1520 taken using one or more sensors of the wearable medical device and/or a separate device. In one embodiment, selected historical trending of measurement data 1510 is a previous measurement data set for a selected period of time, for a selected activity, or a selected environment, or for other criteria. FIG. 15 illustrates on exemplary embodiment of the wearable medical device forecasting a spike in a heart rate of an individual based on the historical trending of measurement data 1510 and/or current trending of measurement data 1520. For example, the historical trending of measurement data 1510 shows a substantially constant heart rate trend and the current trending of measurement data 1520 shows a dip in the heart rate of the individual. In this example, the wearable medical device can compare the a selected historical trending of measurement data 1510 and/or current trending of measurement data 1520 with other data sets or data groups stored on the wearable medical device or the separate device and determine that future trending of measurement data 1540 may follow a similar trend to the stored data sets or data groups.

In another embodiment, the wearable medical device can project or forecast selected future medical or physiological measurements of the user by analyzing collected current measurement data and/or historical measurement data from the wearable medical device and/or the separate device. In another embodiment, the wearable medical device can project selected future medical or physiological events or conditions of the user by analyzing collected present and/or historical measurement data from the wearable medical device and/or the separate device. For example, the wearable medical device can collect and store hydration level measurements taken by a sensor of the wearable medical device. The wearable medical device can analyze the stored hydration level measurements and the current hydration level measurements and based on the analyzed stored hydration level measurements and the current hydration level measurements, the wearable medical device can forecast the probable hydration level of the user in the future.

Selected physiological responses of the user in data measured by one or more sensors of the wearable medical device can be filtered out and/or calibrated. Selected physiological responses in data can include: resting heart rate, sweating, increased glucose levels after eating, changes in skin temperature as the ambient temperature changes, and other physiological responses. Selected physiological responses can cause a false positive in sensor measurements or sensor data. The wearable medical device can filter out undesirable or detrimental physiological responses in the data to enable the wearable medical device to efficiently or accurately monitor or measure other physiological responses and/or take other medical measurements.

In one embodiment, the wearable medical device can measure a hydration level or change in the hydration level of a user. In one embodiment, the wearable medical device can filter out the effect of rehydration of a user, such as when the user takes a drink or otherwise intakes fluids while wearing the wearable medical device. In another example, when a user consumes or intakes more fluids and fuel than the body of the user can absorb, the wearable medical device can be calibrated to determine the peak or maximum rehydration level or rate of the body of the user can absorb fluids or fuel. In another embodiment, the wearable medical device can be calibrated to measure a hydration level of a user of the wearable medical device based on the fluid absorption rate of the user.

In one embodiment, the wearable medical device can use a predefined average or maximum rate of a physiological response of the body to calibrate one or more sensors of the wearable medical device. In one embodiment, the wearable medical device can use a predefined average or maximum rate of a physiological response of the body to filter out data or measurements taken by one or more sensors of the wearable medical device. For example, the wearable medical device can determine an average or maximum rate the body of the user can absorb fluid and filter out and data points in measurement data that exceeds the average or maximum rate the body of the user can absorb fluid. In one embodiment, the predefined average or maximum rate of a physiological response of the body can be based on the body of the individual wearing the wearable medical device. In another embodiment, the predefined average or maximum rate of a physiological response of the body can be based on the body of a group of individuals or another individual.

In one embodiment, the wearable medical device can determine the average or maximum rate the body of the user can absorb by analyzing the historical medical measurement data or predetermined medical measurement data. In another embodiment, the wearable medical device can use the average or maximum rate of plurality of individuals by analyzing the historical medical measurement data or predetermined medical measurement data for the plurality of individuals. For example, on average a healthy kidney of an individual at rest can excrete 800 to 1,000 milliliters of fluid per hour and a person can absorb fluid at a rate of 800 to 1,000 milliliters per hour without experiencing a net gain in fluid retained or absorbed by the body of individual. In another example, when the individual is running a marathon, the stress of the marathon can increase vasopressin levels, reducing the excretion capacity of the kidneys of the individual, such as low to excreting 100 milliliters per hour.

When the individual running the marathon drinks 800 to 1,000 milliliters of fluid per hour, there can be a net gain in fluid retained or absorbed by the body of the individual.

The wearable medical device can monitor the intake and excretion of fluids for an individual or plurality of individuals, store the measurement information, and analyze the historical medical measurement data to determine a maximum rate the user can absorb fluid. In another embodiment, the wearable medical device can store predetermined medical measurement data, such as public health statistic, and compare and fit or match the predetermined medical measurement data with the medical measurements of the wearable medical device to calibrate data from one or more sensors of the wearable medical device based on the predetermined medical measurement data.

In one embodiment, the wearable medical device can use the average sweat rate of an individual or the average sweat rate for a group of individuals with the same or similar physical characteristic to calibrate measurement data from one or more sensors of the wearable medical device and/or a separate medical device. For example, the average person sweats between 0.8 to 1.4 liters per hour during exercise. In one embodiment, the wearable medical device can account for the fluid loss from the sweating of the individual by using an independent medical device to measure the fluid loss of the individual due to sweating. For example, an individual can measure his naked weigh using a bathroom scale at a selected time of day, such as an hour before exercising. After the individual has completed an hour of exercise, the individual can again measure the naked weigh himself using the bathroom scale. In one embodiment, to attain a more accurate sweat rate measurement for the individual, the individual may not use the toilet or consume any fluids during the period between the first weighing and the second weighing. In one embodiment, for each kilogram of weight lost between the first weighing and the second weighing, the individual may have lost one liter of fluid. In another embodiment, the individual can drink fluids or excrete fluids, such as by using the rest room, between the first weighing and the second weighing and the estimated weights of the fluid drunk or excreted can be used to adjust the calibration and/or medical measurements.

Figure 16A:
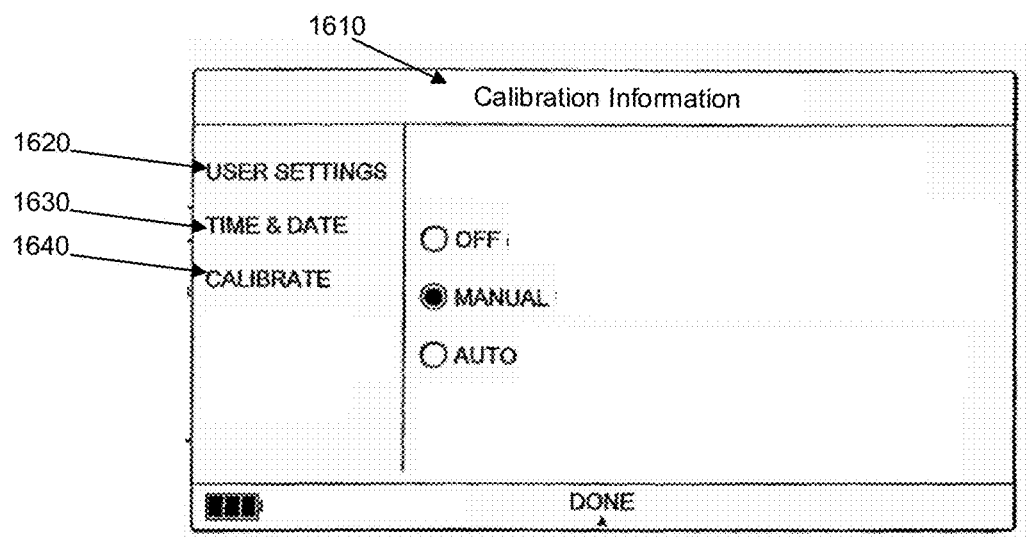
FIG. 16*a* depicts a wearable medical device that can receive selected calibration information in accordance with an example.

FIG. 16a shows that a wearable medical device can receive selected calibration information. In one embodiment, the selected calibration information 1610 can include: user settings 1620, such as calibration sensitivity 1640; user habit information 1630, such as habitual periods of time when the user may be inactive or less active (such as while sleeping or at work). In another embodiment, the selected calibration information 1610 can include: selected time intervals for recalibration, such as how often the wearable medical device recalibrates; and other calibration information.

Figure 16B:
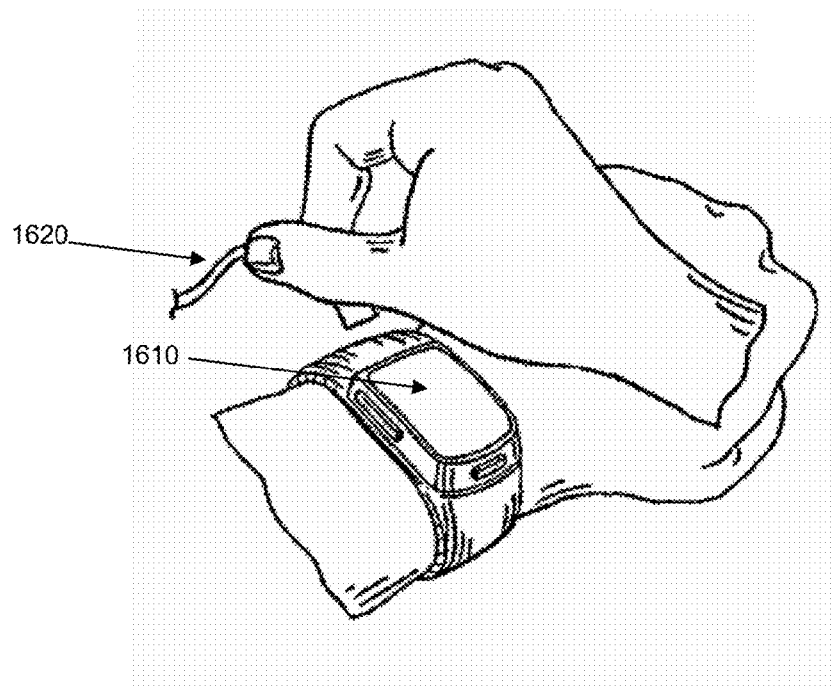
FIG. 16*b* depicts a wearable medical device that can receive data or information from an external device in accordance with an example.

FIG. 16b illustrates that the wearable medical device 1610 can receive data or information, such as user input, from an external device. FIG. 16b illustrates that the wearable medical device can receive data or information wiredly, such as via a cable 1620, that can connect and transfer information to and/or from the wearable medical device 1610. In another embodiment, the wearable medical device 1610 can receive data or information wirelessly, such as via a Bluetooth connection, Zigbee connection, Wi-Fi network, or cellular network.

Figure 17:
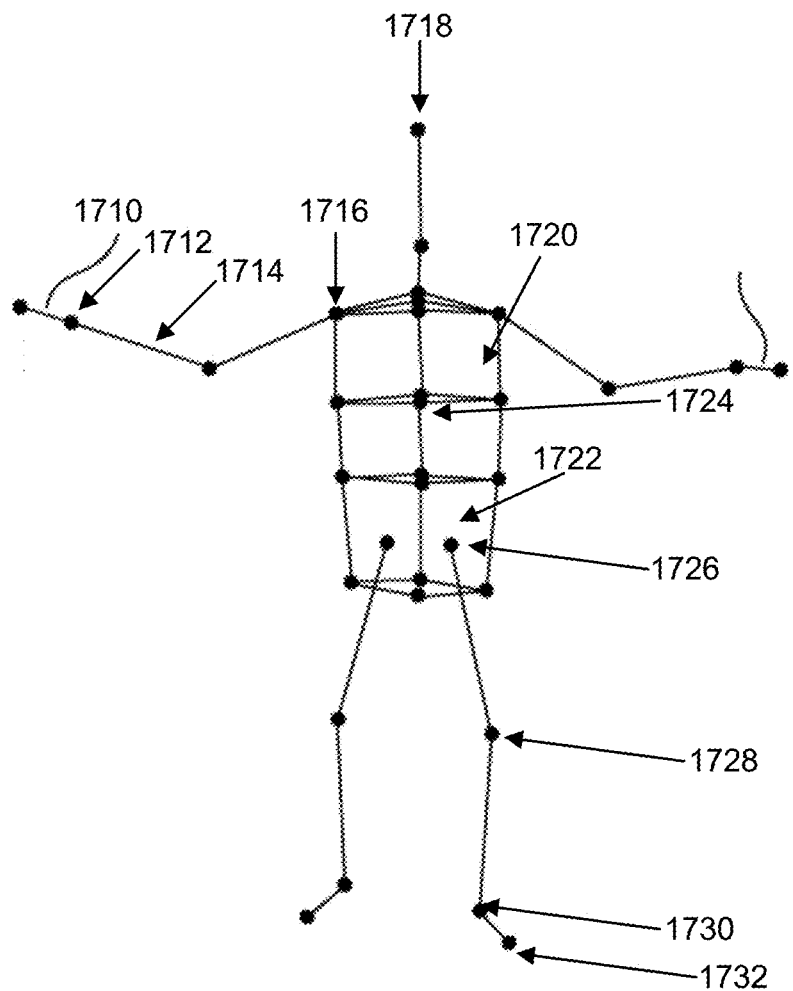
FIG. 17 depicts illustrates selected locations where a wearable medical device can be attached to the body of an individual in accordance with an example.

FIG. 17 illustrates selected locations where a wearable medical device can be attached to the body of an individual. In one embodiment, the selected locations on the individual can include: a hand 1710, a wrist 1712, an arm 1714, a shoulder 1716, a head 1718, a chest 1720, a stomach 1722, a back 1724, a hip 1726, a knee 1728, a ankle or leg 1730, a foot 1732, or any other location on the individual. In one embodiment, a plurality of wearable medical devices can be located at different selected locations on the individual. In one embodiment, the plurality of wearable medical devices can communicate data or information between the wearable medical devices.

In another embodiment, the wearable medical device can be calibrated to account for the affect of environmental factors, such as for an ambient temperature and/or the environmental humidity, in measurement data. For example, when the ambient temperature approximate an individual increases, the sweat rate of the individual may increase. The wearable medical device can filter out the measurement data and/or calibrate the sensors of the wearable medical device to account for a sudden decrease of fluids due to an increase in the ambient temperature rather than a CHF event.

Another technique used to calibrate the wearable medical device can be to use an algorithm to determine when to calibrate the wearable medical device or to reset the baseline for measurement data of the wearable medical device. For example, when measurement data from one or more sensors of the wearable medical device is atypical or abnormal, the wearable medical device can analyze the measurement data to determine a probable cause of the abnormality in the measurement data and use an internal sensor to calibrate one or more sensors of the wearable medical device. In another example, when measurement data from one or more sensors of the wearable medical device is atypical or abnormal, the wearable medical device can analyze the measurement data to determine a probable cause of the abnormality in the measurement data and use a separate device to calibrate one or more sensors of the wearable medical device or measurement data of the wearable medical device. In another embodiment, the algorithm can be used to recalibrate the measurement data and/or sensors of the wearable medical device. In another embodiment, a verification standard can be used to calibrate the wearable medical device. In one embodiment the verification standard can be a standard set by a medical standards board, such as the American Board of Medicine. In another embodiment, the standard separate device can be selected to take measurements to compare with the wearable medical device. For example, the standard separate device can be a standard pulse oximeter device that the American Board of Medicine has selected as the standard device to use to determine a selected physiological measurement.

The wearable medical device can be calibrated using a data or information set collected from a selected group of individuals (crowdsourced data). In one embodiment, the crowdsourced data can be categorized and/or filtered to determine similarities in the data for the selected group of individuals as an aggregate. For example, the crowdsourced data can be filtered to determine the range of measurements for the group of individuals for a medical measurement such as hydration using bioimpedance.

The crowdsourced data can be categorized and/or filtered to determine similar characteristics in the data for each individual in the group. In one embodiment, the data for each individual can be analyzed to determine trends in the measurement data of each individual, such as when the individual is at a rest or exercising. The crowdsourced data can be categorized based on selected criteria such as age, gender, weight, ethnicity, race, fitness level, geographical information, or other demographic criteria. In one embodiment, the wearable medical device can be calibrated based on the crowdsourced data by determining the average baseline measurement for the aggregated crowdsourced data and setting the baseline of the wearable medical device at the average baseline calibration for the aggregated crowdsourced data.

In one embodiment, a selected characteristic of the user of the wearable medical device can be mapped to individuals in the selected group with similar characteristics. The baseline calibration of the individuals in the selected group can be used as the baseline calibration for the user of the wearable medical device. For example, the user can enter his demographic information into the wearable medical device and the wearable medical device can map the user's entered demographic information to individuals with similar demographic information to determine expected ranges for selected medical measurements or physiological measurements taken by the wearable medical device. In one embodiment, when the medical or physiological measurements or data are outside a selected range, the wearable medical device can indicate to the user to calibrate the wearable medical device. In another embodiment, when the medical or physiological measurements or data are outside a selected range, the wearable medical device can automatically calibrate the wearable medical device.

In one embodiment, the wearable medical device can calibrate the wearable medical device by adjusting one or more sensors of the wearable medical device, such as adjusting the power level provided to the sensor. In another embodiment, the wearable medical device can calibrate the wearable medical device by filtering out interference or noise from one or more sensors of the wearable medical device and/or external interference or noise. In another embodiment, the wearable medical device can calibrate the wearable medical device by resetting the baseline from which the measurement data of one or more sensors of the wearable medical device measures. In another embodiment, the wearable medical device can calibrate the wearable medical device by adjusting or filtering the physiological measurement data or medical measurement data from one or more sensors of the wearable medical device and/or a separate device. In one embodiment, adjusting or filtering the physiological measurement data or medical measurement data from one or more sensors of the wearable medical device and/or a separate device can be done using weighted values or weighted scalars as discussed in the preceding paragraphs.

In another embodiment, the wearable medical device can calibrate the wearable medical device based on personal information entered by the user, such as the physiology of the user. For example, the wearable medical device can calibrate the wearable medical device and/or analyze the medical measurements from the wearable medical device differently based on if the user is a male or a female. For example, in comparing the rate at which men and women of similar physical fitness levels perspire during physical activity, men sweat more than women and therefore can lose more bodily fluid for the same amount of exertion over the same period of time. In this example, the wearable medical device can be calibrated to adjust for the rate of perspiration of the user based on their gender.

In another example, an individual that is physically fit typically begins sweating at a lower core body temperature than an individual that is not physically fit. The wearable medical device can be calibrated based on the physical fitness level of the user to compensate for when the user may begin sweating. In another example, females that are not exerting themselves can have a lower sweat rate than males not exerting themselves and the wearable medical device can be calibrated to compensate for the sweat rate based on the gender and exertion level of the individual.

The wearable medical device can be calibrated based on the user's physiology. In one embodiment, the wearable medical device can calibrate measurement data based on the fitness level of user of the wearable medical device. In another embodiment, the wearable medical device can calibrate measurement data based on the exertion level of the individual. For example, sweat output per sweat gland during an intense exercise period can be higher for individuals that are relatively physically fit than for individuals that are relatively out of shape. The sweat output per sweat gland for women that are relatively out of shape may take longer to reach a maximum sweat output per sweat gland than for women that are relatively physically fit. The wearable medical device can calibrate or adjust the measurement data, such as sweat output per sweat gland based on the relative fitness level and gender of the user.

In another embodiment, the health condition of the user can be used to calibrate one or more sensors of the wearable medical device. For example, when an individual is sick or unhealthy, the fluid level of the individual can be lower and cause the skin of the individual to tighten. The wearable medical device can calibrate one or more sensors based on the tightened skin of the individual. In another embodiment, the health condition of the user can be used to calibrate measurement data from one or more sensors of the wearable medical device. For example, if the individual is sick and vomiting, the fluid level of the individual may change at a relatively quicker level than a healthy individual that is not vomiting fluid or otherwise losing fluid and the wearable medical device can adjust the measurement data based on the health level of the individual.

In one embodiment, the calibration and/or recalibration of the wearable medical device can be done automatically, e.g. without any input from the patient or user. For example, when the wearable medical device determines that the wearable medical device should be recalibrated, the wearable medical device can use the internal sensor of the wearable medical device to take recalibration measurements and recalibrate the wearable medical device based on the recalibration measurements. In another example, when the wearable medical device determines that the wearable medical device should be recalibrated, the wearable medical device can wait to receive recalibration measurements from a separate device. When the wearable medical device receives the recalibrate measurements from the separate device, the wearable medical device can recalibrate the wearable medical device based on the recalibrate measurements from the separate device.

In one embodiment, when the wearable medical device determines that the wearable medical device should be recalibrated, the wearable medical device can send out a beacon or signal to a separate device to communicate to the independent medical device to take calibration measurements the next time the user of the wearable medical device uses the independent medical device. In one embodiment, the independent medical device can receive a beacon or signal from the wearable medical device verifying that the user is the individual using the independent medical device to enable the separate device to take a measurement and communicate the measurement to the wearable medical device.

The wearable medical device can wirelessly communicate with other devices using an optical connection such as an infrared connection, or via a radio frequency connection, such as a wireless fidelity (Wi-Fi) network, Wi-Fi direct, a Bluetooth connection, a cellular communications system such as a third generation partnership project (3GPP) long term evolution (LTE) connection, device to device (D2D) communication, a machine type communication, or via another type of proprietary wireless connection. The cellular communications system can comprise one or more cellular network nodes and one or more Institute of Electrical and Electronics Engineers (IEEE) 802.11-2012 configured access points. In one embodiment, the one or more cellular networks may be 3rd generation partnership project (3GPP) long term evolution (LTE) Rel. 8, 9, 10, or 11 networks and/or IEEE 802.16p, 802.16n, 802.16m-2011, 802.16h-2010, 802.16j-2009, 802.16-2009 networks.

The wearable medical device can indicate to the user the accuracy level or calibration level of the wearable medical device, the sensor array of the wearable medical device, or a selected sensor of the wearable medical device. In one embodiment, the wearable medical device can determine the accuracy level or calibration level of the wearable medical device and indicate the accuracy level or calibration level based for selected ranges of accuracy or calibration. For example, when the wearable medical device is within a range of 85% to 100% accuracy level, the wearable medical device can indicate that the wearable medical device is fully calibrated. When the accuracy level of the wearable medical device is within a range of 75% to 84% accuracy, the wearable medical device can indicate that the wearable medical device is marginally calibrated. When the accuracy level of the wearable medical device is below 75% accuracy, the wearable medical device can indicate that the wearable medical device may need to be recalibrated. The wearable medical device can indicate the accuracy or calibration level using a sensory indication, such as different color lights or sounds for different accuracy levels.

In one embodiment, the wearable medical device can be recalibrated manually, e.g. the user can manually take a calibration measurement. For example, the wearable medical device can indicate to the user that the wearable medical device should be recalibrated. The user can then use the internal sensor of the wearable medical device or a separate device to take a recalibration measurement and input recalibration measurement information into the wearable medical device.

In another embodiment, the wearable medical device can be recalibrated on a periodical basis. In one embodiment, the wearable medical device can automatically recalibrate on a periodic basis. For example, the wearable medical device can use the internal sensors or the independent medical device at a selected time, such as Monday of each week, and recalibrate the wearable medical device based on the calibration measurements. In one embodiment, the wearable medical device can be manually recalibrated on a periodic basis. For example, the user can take a measurement using the internal sensors or the independent medical device at a selected time, such as Monday of each week, and input the calibration measurements into the wearable medical device. The wearable medical device can use the calibration measurement to recalibrate the wearable medical device. In one embodiment, the wearable medical device can use a sensory indicator, such as a light, sound, or vibration to indicate to the user that the periodic recalibration period has arrived.

When the wearable medical device has come out of alignment or there is interference with the sensors of the wearable medical device, the wearable medical device can signal the user of the wearable medical device or a 3rd party to calibrate the wearable medical device. In one embodiment, the wearable medical device can indicate to the user to calibrate the wearable medical device or that an error has occurred in taking medical measurement by using a sensory indication such as a sound, vibration, displaying a message and so forth. For example if the wearable medical device determines that there is interference between the sensors and the location the sensors are taking measurements on the user, the wearable medical device can display an error message on a display screen. In another embodiment, the wearable medical device can alert a third party, such as a medical care giver, that the wearable medical device is not taking accurate medical measurements and/or indicate to the third party to adjustment or calibration the wearable medical device.

In one embodiment, the wearable medical device can determine if there has been a movement of the wearable medical device that has caused it to become unaligned. In one embodiment, the wearable medical device can use a movement sensor, such as an accelerometer, to determine when the wearable medical device has come out of alignment. For example, when the movement sensor detects a relatively abrupt movement of the wearable medical device, the wearable medical device can determine that the wearable medical device has moved out of alignment. In one embodiment, when the wearable medical device has moved out of alignment the wearable medical device can be moved back into place or realigned. In another embodiment, the wearable medical device can be recalibrated or set a new baseline from which medical measurements or physiological measurements are measured for the new location of the wearable medical device on the user's body.

In another embodiment, the movement sensor can be used to continuous recalibrate, filter, or compensate for movement of the wearable medical device and/or of the user. For example if the wearable medical device is used during an active period of the user, such as when the user is jogging or exercising, the movement sensor can determine that there is a consistent or constant movement of the wearable medical device and can compensate, adjust, and/or filter the medical measurement data or physiological measurement data to remove interference caused by movement of the wearable medical device.

The wearable medical device can be adjusted or calibrated to take different medical measurements when a physiological event, such as a cardiac arrhythmia or an episode of patient discomfort, has been detected. For example, during a normal physiological period the wearable medical device can use a predetermined or defined set of calibration parameters in taking medical measurement. In this example, when the user of the wearable medical device undergoes a physiological event, such as a heart attack, low blood pressure, high blood pressure, low blood sugar, low hydration level, and so forth, the wearable medical device can then change the calibration of the sensors of the wearable medical device and/or modify the algorithms used to analyze the measurement information.

In one embodiment, the wearable medical device can initiate capturing the physiological data of a user during a physiological event. In another embodiment, the wearable medical device can use an event recorder to record and/or store information during a physiological event. In another embodiment, when a physiological event is detected by the wearable medical device, a third party, such as a caregiver, can be alerted of the physiological event.

The wearable medical device can detect repetitive patterns in the medical measurements and can calibrate the wearable medical device to filter out the repetitive patterns. In one embodiment, the wearable medical device can alert the user and/or a third party of repetitive patterns in the medical measurement data. For example, if the user of the wearable medical device has a cardiac episode each time the user has a high blood pressure measurement or has a high hematocrit measurement, the wearable medical device can determine when the cardiac episode is likely to occur and alert or indicate to the user and/or the third party when a cardiac episode is likely to happen.

In one embodiment, the wearable medical device can process or analyze, at the wearable medical device, medical measurement data from one or more sensors of the wearable medical device and/or medical measurement data from a separate device. In another embodiment, a separate computing device can receive measurement data from one or more sensors of the wearable medical device and/or medical measurement data from a separate device and process or analyze medical measurement data. The separate computing device can send the processed or analyzed medical measurement data to the wearable medical device or send a calibration value back to the wearable medical device to enable the wearable medical device to calibrate one or more sensors of the wearable medical device and/or measurement data of the wearable medical device.

Figure 18:
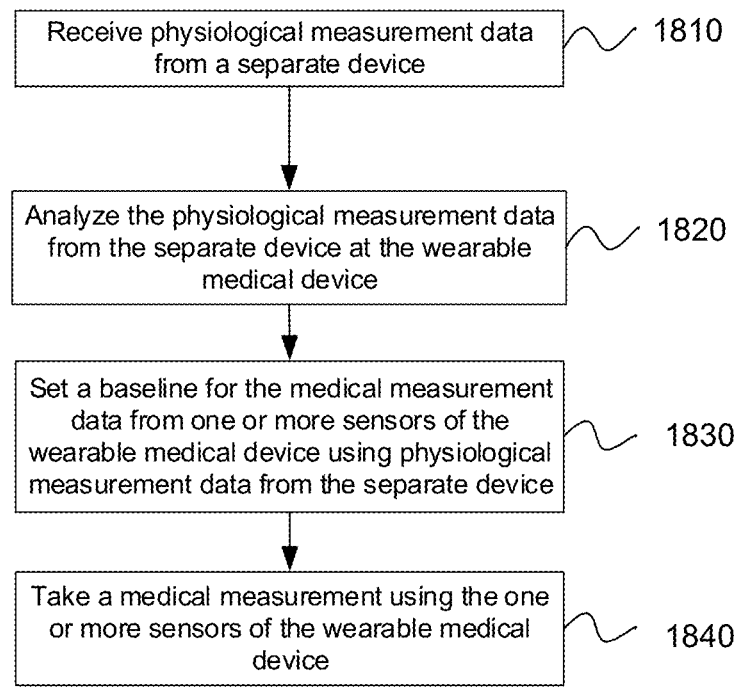
FIG. 18 depicts the functionality of the computer circuitry of a wearable medical device that is operable calibrate sensors of the wearable medical device or medical measurements of the wearable medical device in accordance with an example.

FIG. 18 provides a flow chart 1800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive physiological measurement data from a separate device, as in block 1810. The computer circuitry can be further configured to analyze the physiological measurement data from the separate device at the wearable medical device, as in block 1820. The computer circuitry can also be configured to set a baseline for the medical measurement data from one or more sensors of the wearable medical device using physiological measurement data from the separate device, as in block 1830. The computer circuitry can also be configured to take a medical measurement using the one or more sensors of the wearable medical device, as in block 1840.

Figure 19:
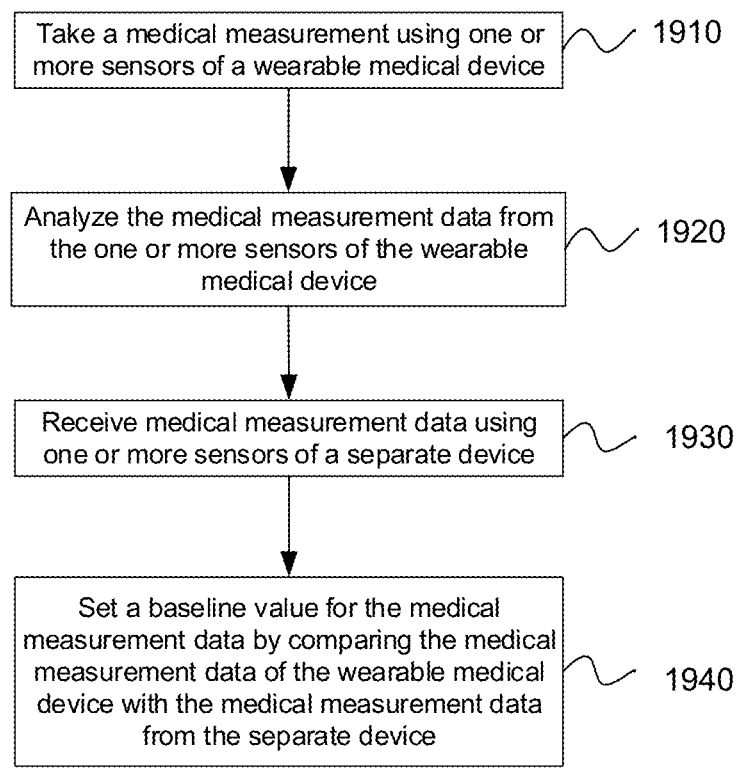
FIG. 19 depicts the functionality of another computer circuitry of a wearable medical device that is operable calibrate sensors of the wearable medical device or medical measurements of the wearable medical device in accordance with an example.

FIG. 19 provides a flow chart 1900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more sensors of a wearable medical device, as in block 1910. The computer circuitry can be further configured to analyze the medical measurement data from the one or more sensors of the wearable medical device, as in block 1920. The computer circuitry can also be configured to receive medical measurement data using one or more sensors of a separate device, as in block 1930. The computer circuitry can also be configured to set a baseline value for the medical measurement data by comparing the medical measurement data of the wearable medical device with the medical measurement data from the separate device, as in block 1940.

Figure 20:
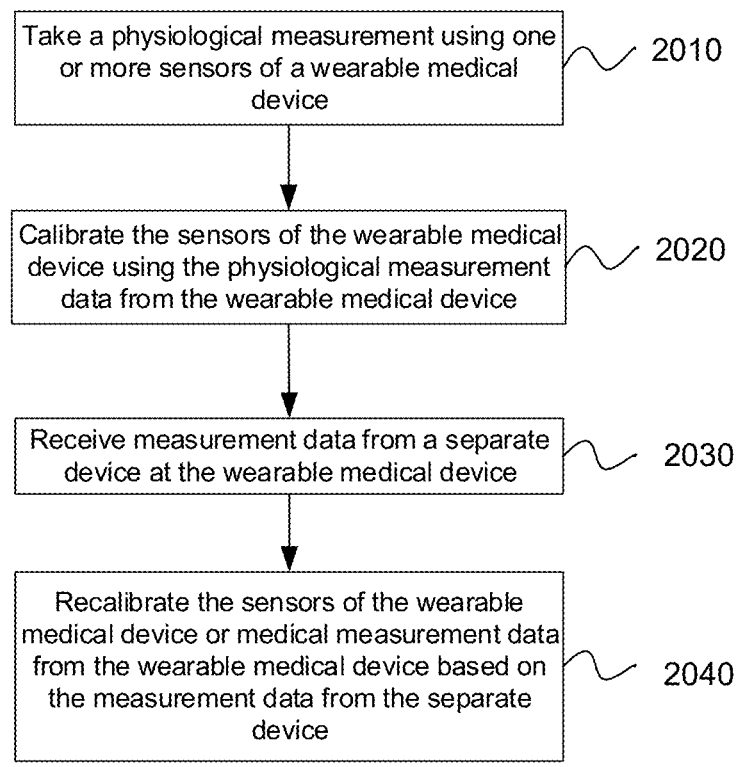
FIG. 20 depicts the functionality of another computer circuitry of a wearable medical device that is operable calibrate sensors of the wearable medical device or medical measurements of the wearable medical device in accordance with an example.

FIG. 20 provides a flow chart 2000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement using one or more sensors of a wearable medical device, as in block 2010. The computer circuitry can be further configured to calibrate the sensors of the wearable medical device using the physiological measurement data from the wearable medical device, as in block 2020. The computer circuitry can also be configured to receive measurement data from a separate device at the wearable medical device, as in block 2030. The computer circuitry can also be configured to recalibrate the sensors of the wearable medical device or medical measurement data from the wearable medical device based on the measurement data from the separate device, as in block 2040.

Figure 21:
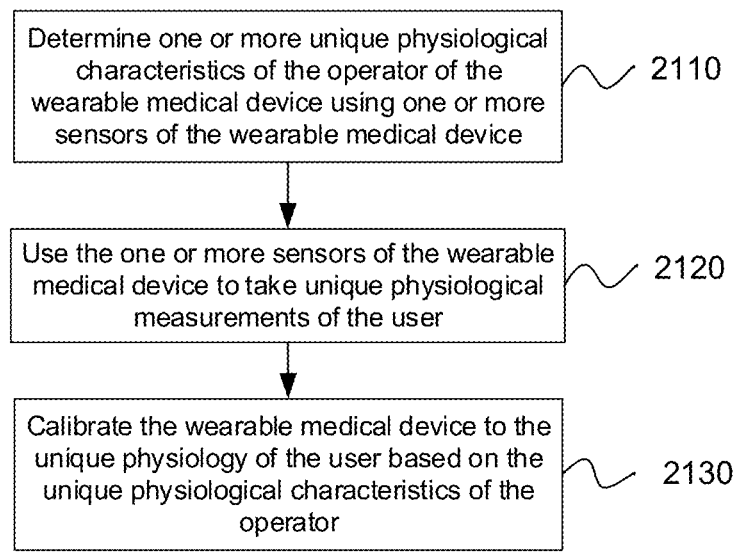
FIG. 21 depicts the functionality of another computer circuitry of a wearable medical device that is operable calibrate sensors of the wearable medical device or medical measurements of the wearable medical device in accordance with an example.

FIG. 21 provides a flow chart 2100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine one or more unique physiological characteristics of the operator of the wearable medical device using one or more sensors of the wearable medical device, as in block 2110. The computer circuitry can be further configured to use the one or more sensors of the wearable medical device to take unique physiological measurements of the user, as in block 2120. The computer circuitry can also be configured to calibrate the wearable medical device to the unique physiology of the user based on the unique physiological characteristics, as in block 2130.

Figure 22:
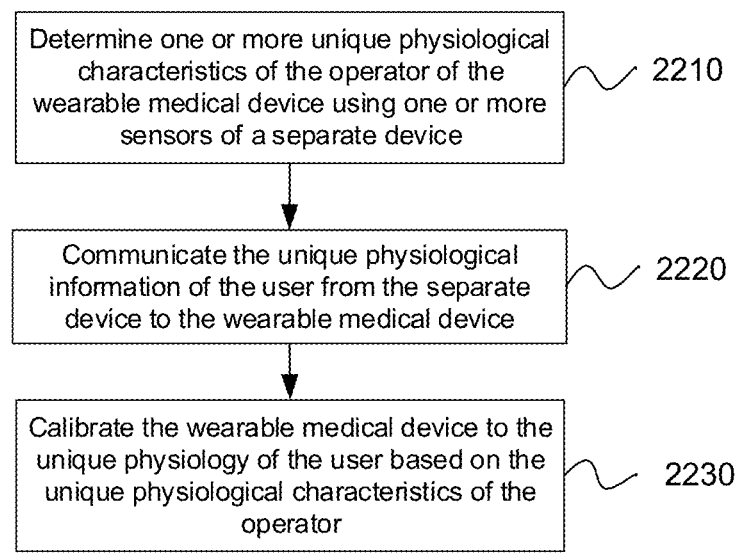
FIG. 22 depicts the functionality of another computer circuitry of a wearable medical device that is operable calibrate sensors of the wearable medical device or medical measurements of the wearable medical device in accordance with an example.

FIG. 22 provides a flow chart 2200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine one or more unique physiological characteristics of the operator of the wearable medical device using one or more sensors of a separate device, as in block 2210. The computer circuitry can be further configured to communicate the unique physiological information of the user from the separate device to the wearable medical device, as in block 2220. The computer circuitry can also be configured to calibrate the wearable medical device to the unique physiology of the user based on the unique physiological characteristics of the operator, as in block 2230.

Figure 23:
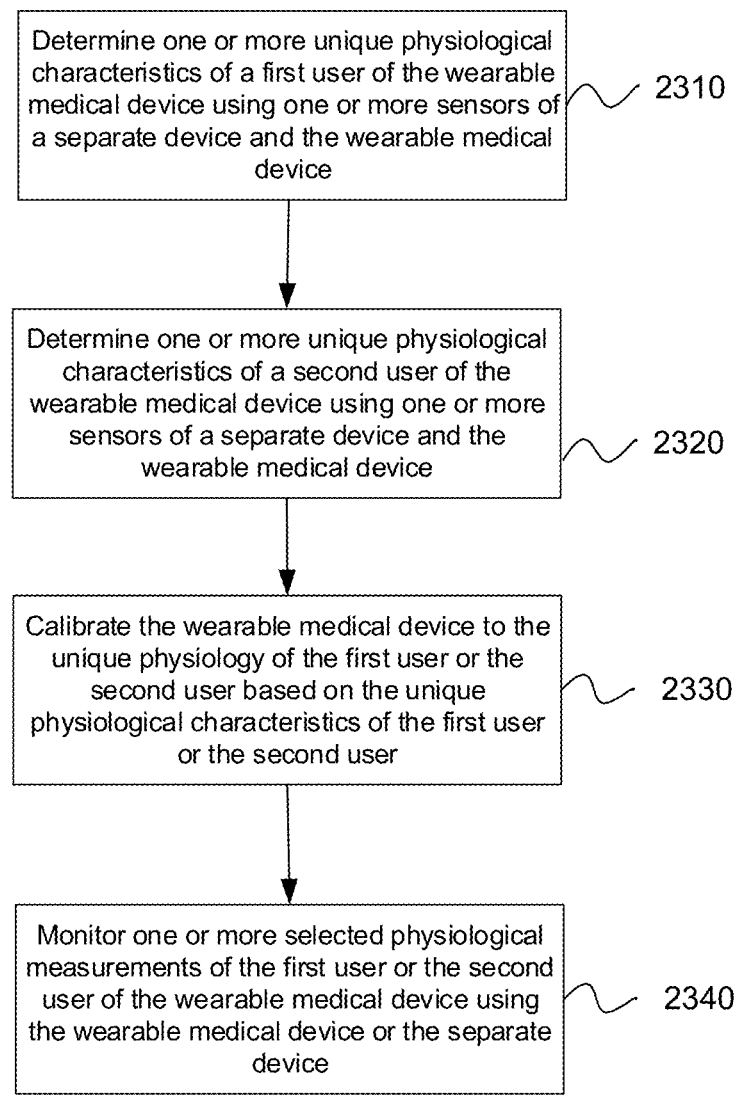
FIG. 23 depicts the functionality of another computer circuitry of a wearable medical device that is operable calibrate sensors of the wearable medical device or medical measurements of the wearable medical device in accordance with an example.

FIG. 23 provides a flow chart 2300 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine one or more unique physiological characteristics of a first user of the wearable medical device using one or more sensors of a separate device and the wearable medical device, as in block 2310. The computer circuitry can be further configured to determine one or more unique physiological characteristics of a second user of the wearable medical device using one or more sensors of a separate device and the wearable medical device, as in block 2320. The computer circuitry can also be configured to calibrate the wearable medical device to the unique physiology of the first user or the second user based on the unique physiological characteristics of the first user or the second user, as in block 2330. The computer circuitry can also be configured to monitor one or more selected physiological measurements of the first user or the second user of the wearable medical device using the wearable medical device or the separate device, as in block 2340.

Figure 24:
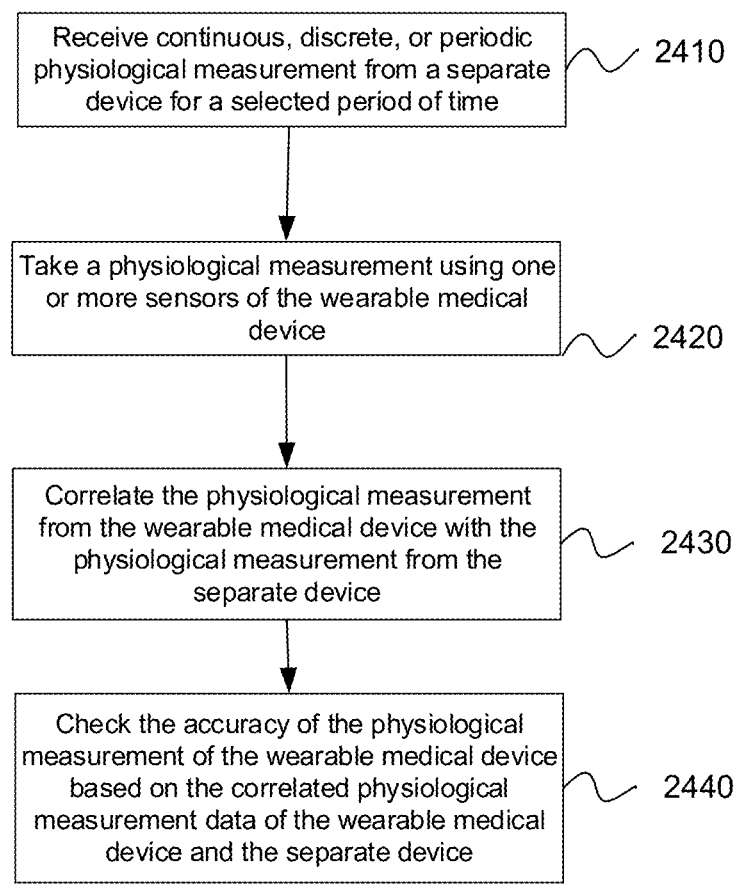
FIG. 24 depicts the functionality of another computer circuitry of a wearable medical device that is operable calibrate sensors of the wearable medical device or medical measurements of the wearable medical device in accordance with an example.

FIG. 24 provides a flow chart 2400 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive continuous, discrete, or periodic physiological measurement from a separate device for a selected period of time, as in block 2410. The computer circuitry can be further configured to take a physiological measurement using one or more sensors of the wearable medical device, as in block 2420. The computer circuitry can also be configured to correlate the physiological measurement from the wearable medical device with the physiological measurement from the separate device, as in block 2430. The computer circuitry can also be configured to check the accuracy of the physiological measurement of the wearable medical device based on the correlated physiological measurement data of the wearable medical device and the separate device, as in block 2440.

Figure 25:
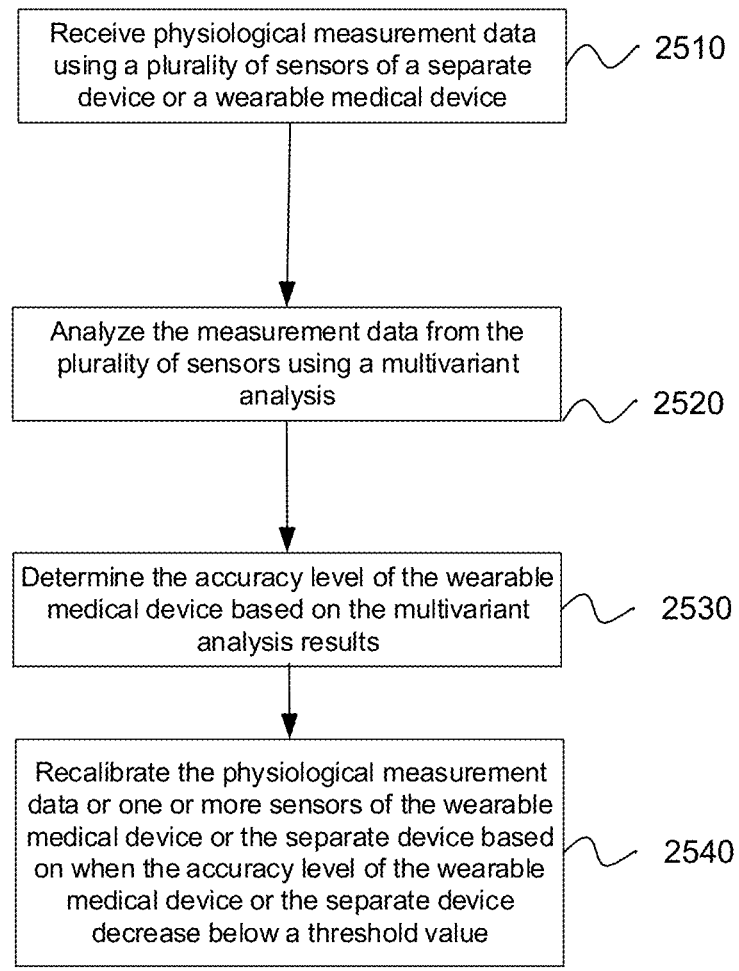
FIG. 25 depicts the functionality of another computer circuitry of a wearable medical device that is operable calibrate sensors of the wearable medical device or medical measurements of the wearable medical device in accordance with an example.

FIG. 25 provides a flow chart 2500 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive physiological measurement data using a plurality of sensors of a separate device or a wearable medical device, as in block 2510. The computer circuitry can be further configured to analyze the measurement data from the plurality of sensors using a multivariant analysis, as in block 2520. The computer circuitry can also be configured to determine the accuracy level of the wearable medical device based on the multivariant analysis results, as in block 2530. The computer circuitry can also be configured to recalibrate the physiological measurement data or one or more sensors of the wearable medical device or the separate device based on when the accuracy level of the wearable medical device or the separate device decrease below a threshold value, as in block 2540.

Figure 26:
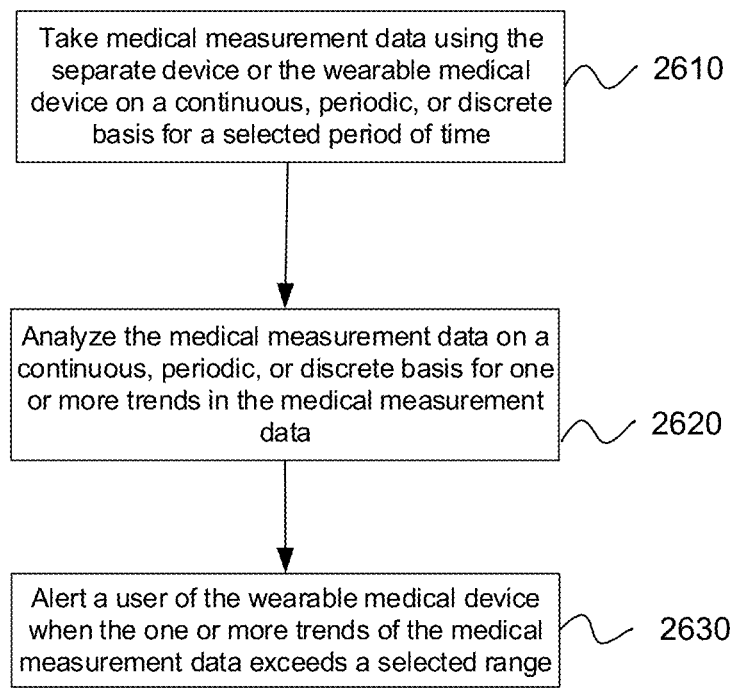
FIG. 26 depicts the functionality of another computer circuitry of a wearable medical device that is operable calibrate sensors of the wearable medical device or medical measurements of the wearable medical device in accordance with an example.

FIG. 26 provides a flow chart 2600 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take medical measurement data using the separate device or the wearable medical device on a continuous, periodic, or discrete basis for a selected period of time, as in block 2610. The computer circuitry can be further configured to analyze the medical measurement data on a continuous, periodic, or discrete basis for one or more trends in the medical measurement data, as in block 2620. The computer circuitry can also be configured to alert a user of the wearable medical device when the one or more trends of the medical measurement data exceeds a selected range, as in block 2630.

Figure 27:
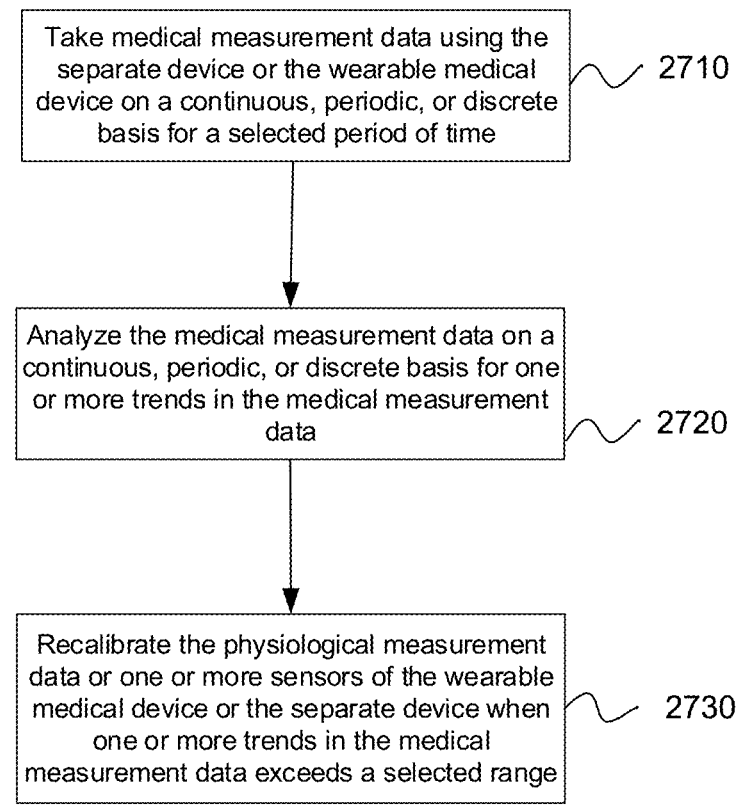
FIG. 27 depicts the functionality of another computer circuitry of a wearable medical device that is operable calibrate sensors of the wearable medical device or medical measurements of the wearable medical device in accordance with an example.

FIG. 27 provides a flow chart 2700 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take medical measurement data using the separate device or the wearable medical device on a continuous, periodic, or discrete basis for a selected period of time, as in block 2710. The computer circuitry can be further configured to analyze the medical measurement data on a continuous, periodic, or discrete basis for one or more trends in the medical measurement data, as in block 2720. The computer circuitry can also be configured to recalibrate the physiological measurement data or one or more sensors of the wearable medical device or the separate device when one or more trends in the medical measurement data exceeds a selected range, as in block 2730.

Figure 28:
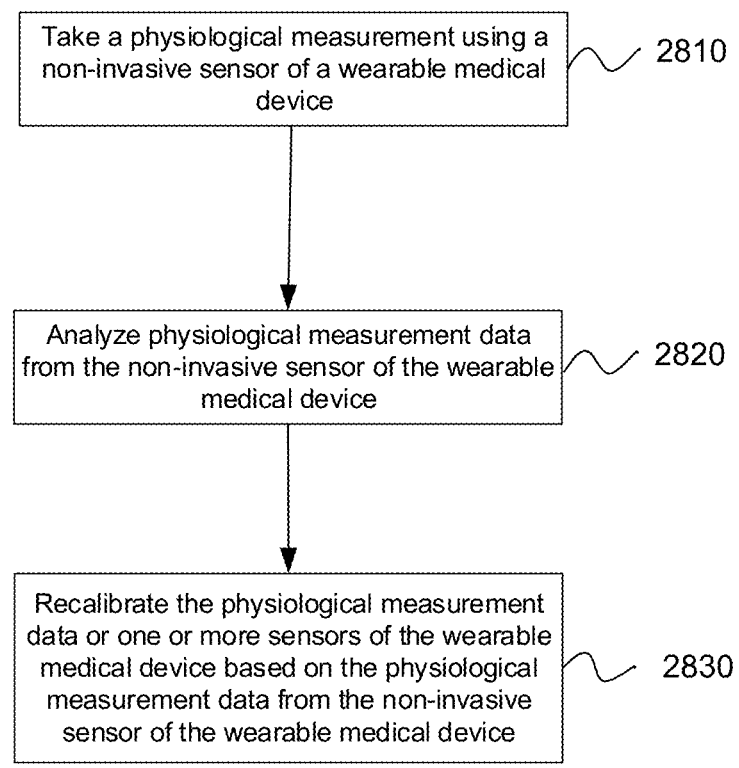
FIG. 28 depicts the functionality of another computer circuitry of a wearable medical device that is operable calibrate sensors of the wearable medical device or medical measurements of the wearable medical device in accordance with an example.

FIG. 28 provides a flow chart 2800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement using a non-invasive sensor of a wearable medical device, as in block 2810. The computer circuitry can be further configured to analyze physiological measurement data from the non-invasive sensor of the wearable medical device, as in block 2820. The computer circuitry can also be configured to recalibrate the physiological measurement data or one or more sensors of the wearable medical device based on the physiological measurement data from the non-invasive sensor of the wearable medical device, as in block 2830.

Figure 29:
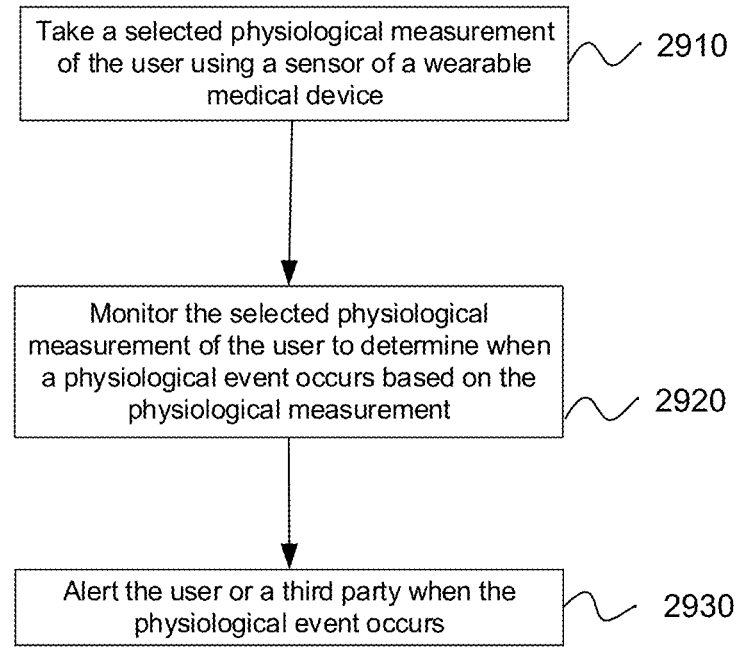
FIG. 29 depicts the functionality of another computer circuitry of a wearable medical device that is operable calibrate sensors of the wearable medical device or medical measurements of the wearable medical device in accordance with an example.

FIG. 29 provides a flow chart 2900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a selected physiological measurement of the user using a sensor of a wearable medical device, as in block 2910. The computer circuitry can be further configured to monitor the selected physiological measurement of the user to determine when a physiological event occurs based on the physiological measurement, as in block 2920. The computer circuitry can also be configured to alert the user or a third party when the physiological event occurs, as in block 2930.

Figure 30:
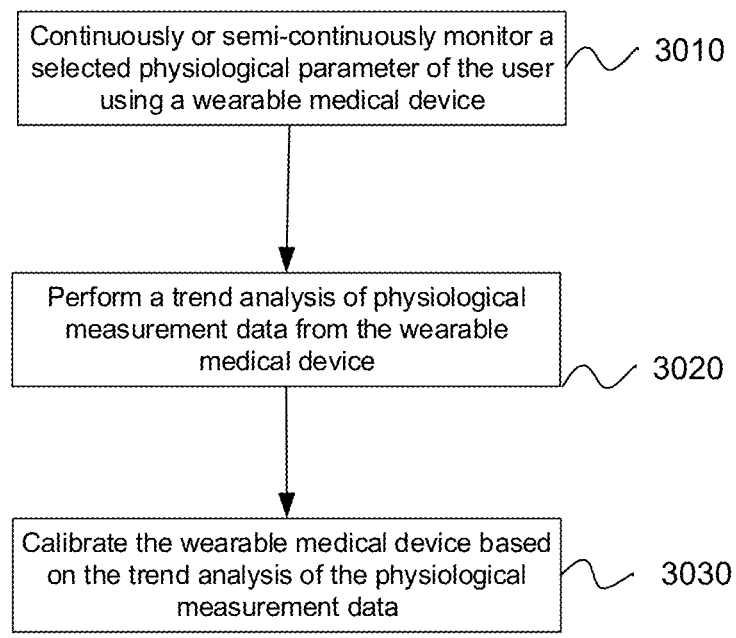
FIG. 30 depicts the functionality of another computer circuitry of a wearable medical device that is operable calibrate sensors of the wearable medical device or medical measurements of the wearable medical device in accordance with an example.

FIG. 30 provides a flow chart 3000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to continuously or semi-continuously monitor a selected physiological parameter of the user using a wearable medical device, as in block 3010. The computer circuitry can be further configured to perform a trend analysis of physiological measurement data from the wearable medical device, as in block 3020. The computer circuitry can also be configured to calibrate the wearable medical device based on the trend analysis of the physiological measurement data, as in block 3030.

Figure 31:
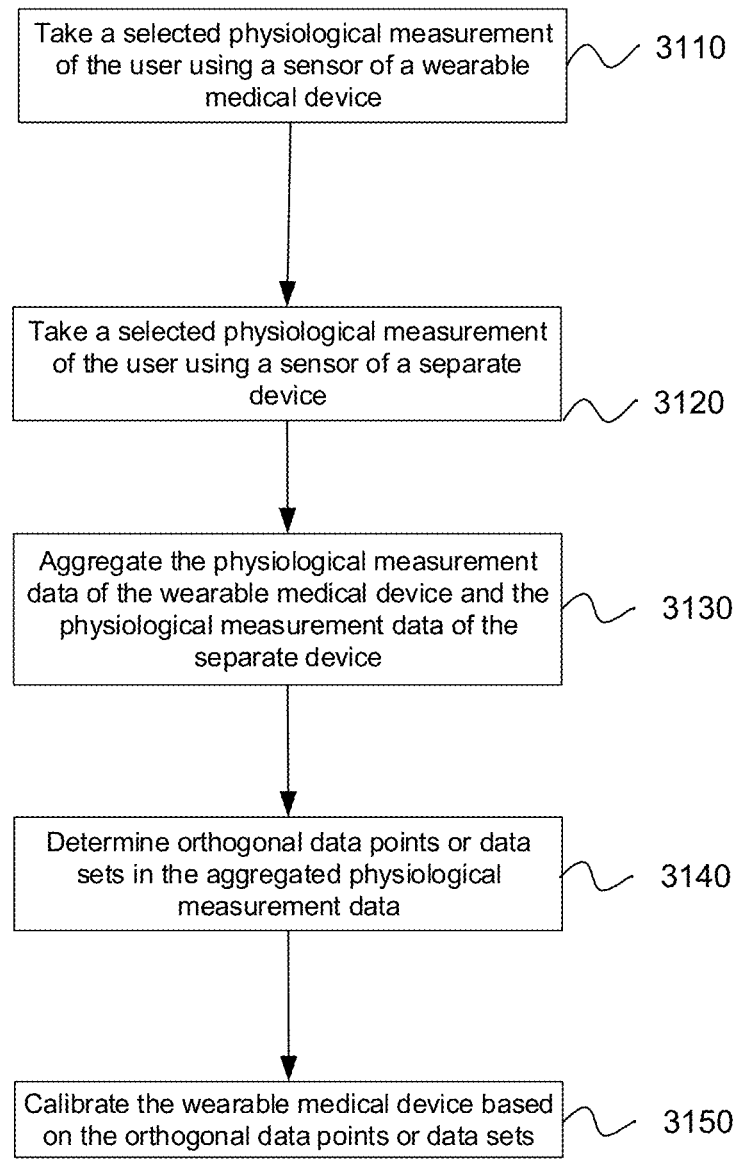
FIG. 31 depicts the functionality of another computer circuitry of a wearable medical device that is operable calibrate sensors of the wearable medical device or medical measurements of the wearable medical device in accordance with an example.

FIG. 31 provides a flow chart 3100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a selected physiological measurement of the user using a sensor of a wearable medical device, as in block 3110. The computer circuitry can be further configured to take a selected physiological measurement of the user using a sensor of a separate device, as in block 3120. The computer circuitry can also be configured to aggregate the physiological measurement data of the wearable medical device and the physiological measurement data of the separate device, as in block 3130. The computer circuitry can also be configured to determine orthogonal data points or data sets in the aggregated physiological measurement data, as in block 3140. The computer circuitry can also be configured to calibrate the wearable medical device based on the orthogonal data points or data sets, as in block 3150.

Figure 32:
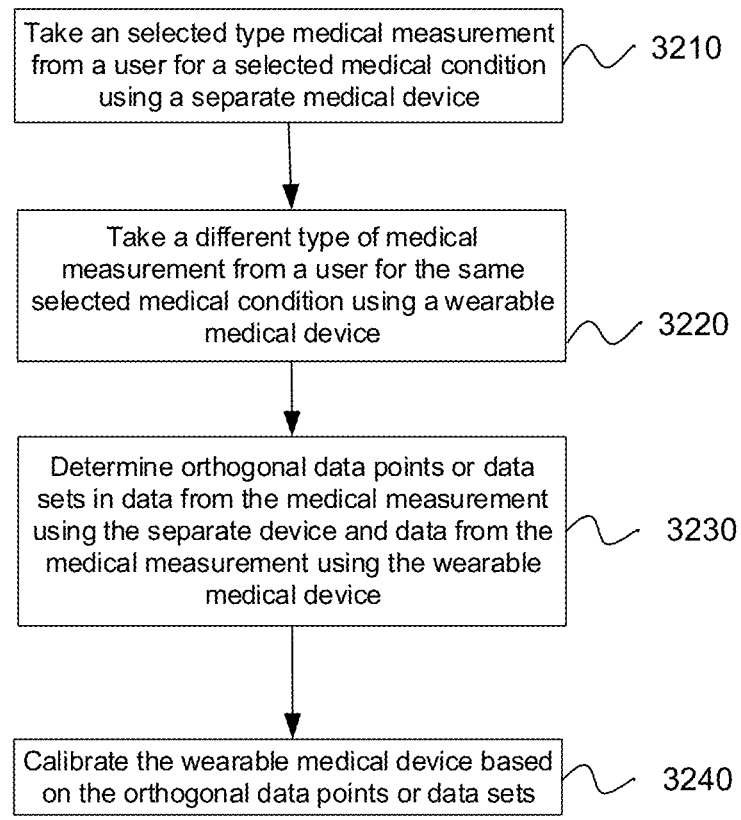
FIG. 32 depicts the functionality of another computer circuitry of a wearable medical device that is operable calibrate sensors of the wearable medical device or medical measurements of the wearable medical device in accordance with an example.

FIG. 32 provides a flow chart 3200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a selected type medical measurement from a user for a selected medical condition using a separate medical device, as in block 3210. The computer circuitry can be further configured to take a different type of medical measurement from a user for the same selected medical condition using a wearable medical device, as in block 3220. The computer circuitry can also be configured to determine orthogonal data points or data sets in data from the medical measurement using the separate device and data from the medical measurement using the wearable medical device, as in block 3230. The computer circuitry can also be configured to calibrate the wearable medical device based on the orthogonal data points or data sets, as in block 3240.

Figure 33:
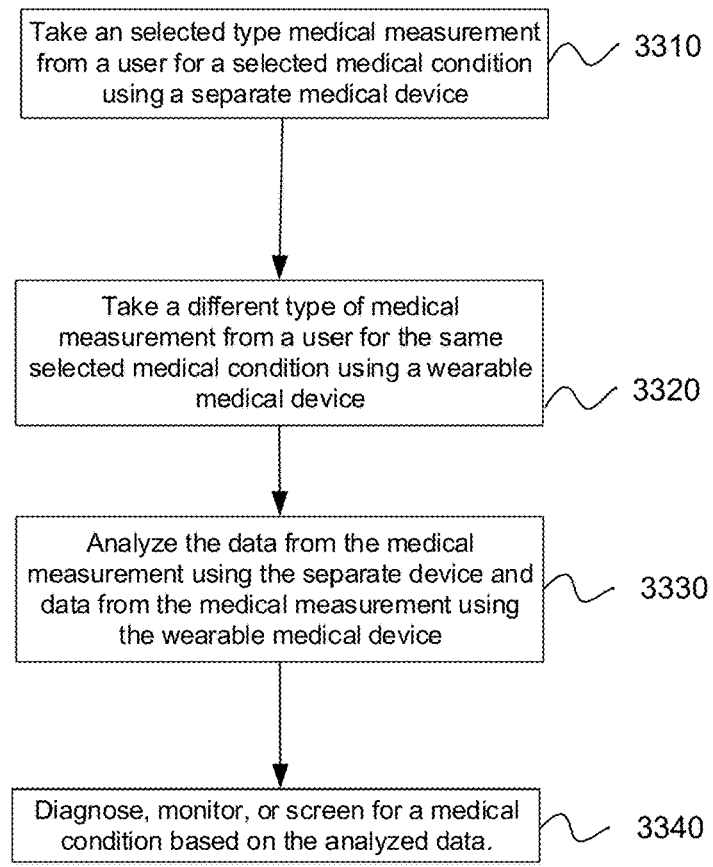
FIG. 33 depicts the functionality of another computer circuitry of a wearable medical device that is operable calibrate sensors of the wearable medical device or medical measurements of the wearable medical device in accordance with an example.

FIG. 33 provides a flow chart 3300 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a selected type medical measurement from a user for a selected medical condition using a separate medical device, as in block 3310. The computer circuitry can be further configured to take a different type of medical measurement from a user for the same selected medical condition using a wearable medical device, as in block 3320. The computer circuitry can also be configured to analyze the data from the medical measurement using the separate device and data from the medical measurement using the wearable medical device, as in block 3330. The computer circuitry can also be configured to diagnose, monitor, or screen for a medical condition based on the analyzed data, as in block 3340.

Figure 34:
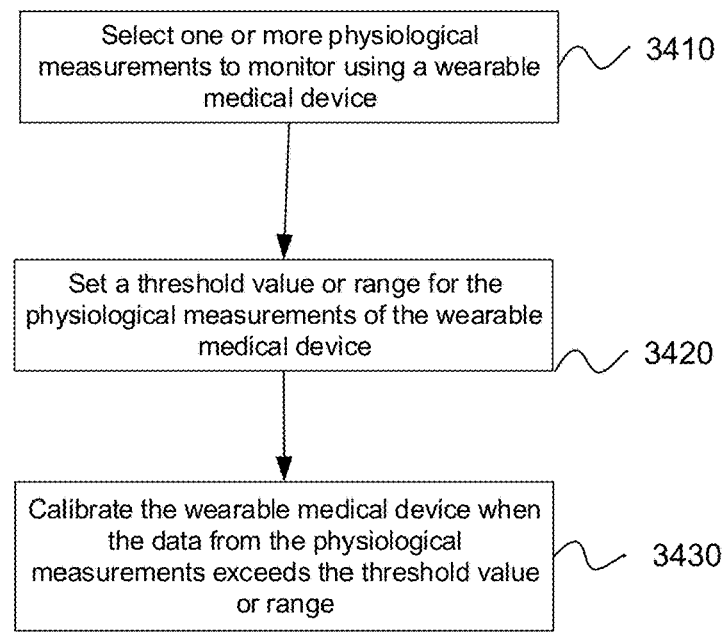
FIG. 34 depicts the functionality of another computer circuitry of a wearable medical device that is operable calibrate sensors of the wearable medical device or medical measurements of the wearable medical device in accordance with an example.

FIG. 34 provides a flow chart 3400 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to select one or more physiological measurements to monitor using a wearable medical device, as in block 3410. The computer circuitry can be further configured to set a threshold value or range for the physiological measurements of the wearable medical device, as in block 3420. The computer circuitry can also be configured to calibrate the wearable medical device when the data from the physiological measurements exceeds the threshold value or range, as in block 3430.

Figure 35:
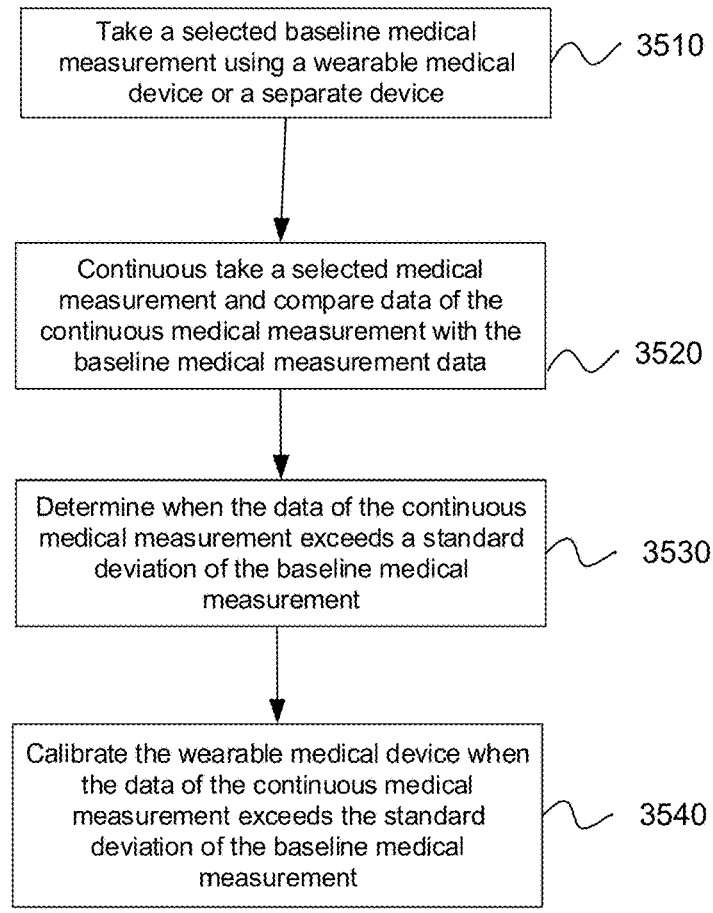
FIG. 35 depicts the functionality of another computer circuitry of a wearable medical device that is operable calibrate sensors of the wearable medical device or medical measurements of the wearable medical device in accordance with an example.

FIG. 35 provides a flow chart 3500 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a selected baseline medical measurement using a wearable medical device or a separate device, as in block 3510. The computer circuitry can be further configured to continuous take a selected medical measurement and compare data of the continuous medical measurement with the baseline medical measurement data, as in block 3520. The computer circuitry can also be configured to determine when the data of the continuous medical measurement exceeds a standard deviation of the baseline medical measurement, as in block 3530. The computer circuitry can also be configured to calibrate the wearable medical device when the data of the continuous medical measurement exceeds the standard deviation of the baseline medical measurement, as in block 3540.

Figure 36:
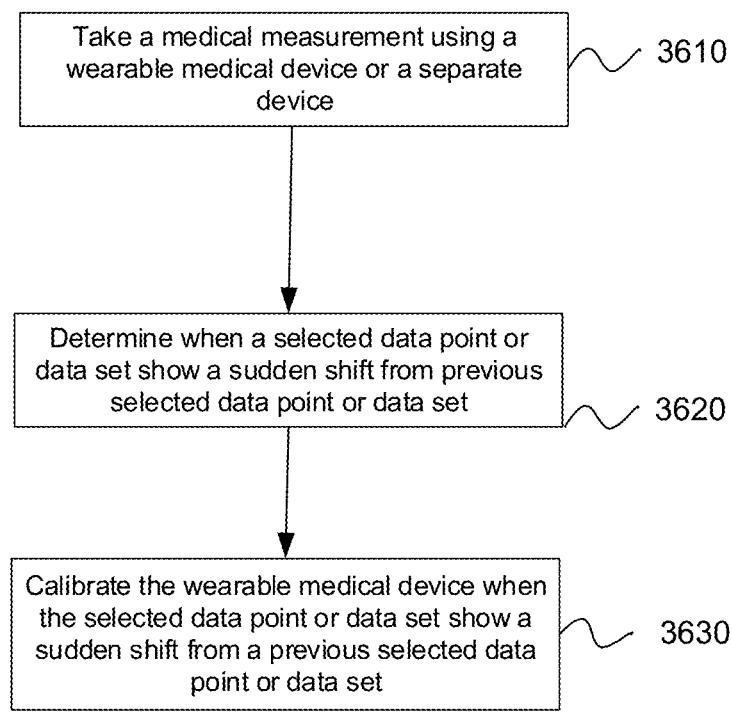
FIG. 36 depicts the functionality of another computer circuitry of a wearable medical device that is operable calibrate sensors of the wearable medical device or medical measurements of the wearable medical device in accordance with an example.

FIG. 36 provides a flow chart 3600 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using a wearable medical device or a separate device, as in block 3610. The computer circuitry can be further configured to determine when a selected data point or data set show a sudden shift from previous selected data point or data set, as in block 3620. The computer circuitry can also be configured to calibrate the wearable medical device when the selected data point or data set show a sudden shift from a previous selected data point or data set, as in block 3630.

Figure 37:
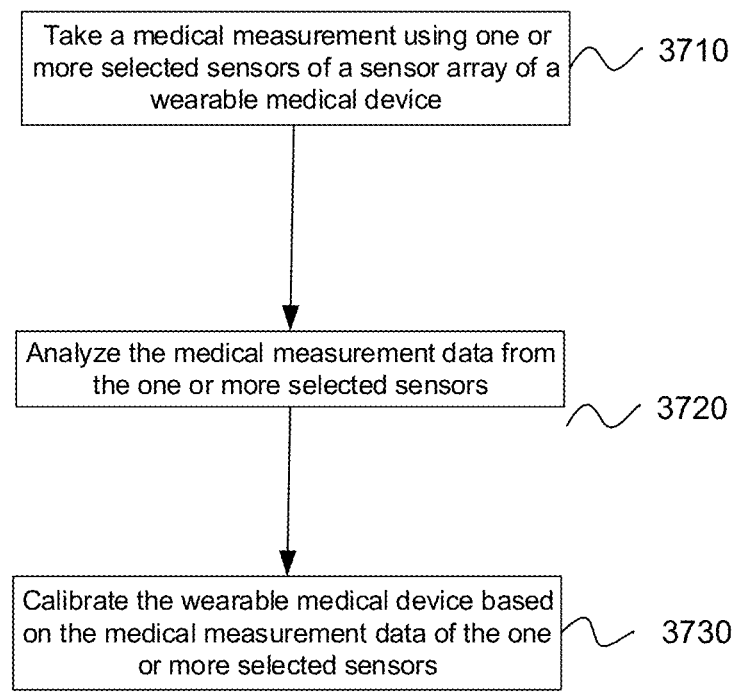
FIG. 37 depicts the functionality of another computer circuitry of a wearable medical device that is operable calibrate sensors of the wearable medical device or medical measurements of the wearable medical device in accordance with an example.

FIG. 37 provides a flow chart 3700 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more selected sensors of a sensor array of a wearable medical device, as in block 3710. The computer circuitry can be further configured to analyze the medical measurement data from the one or more selected sensors, as in block 3720. The computer circuitry can also be configured to calibrate the wearable medical device based on the medical measurement data of the one or more selected sensors, as in block 3730.

Figure 38:
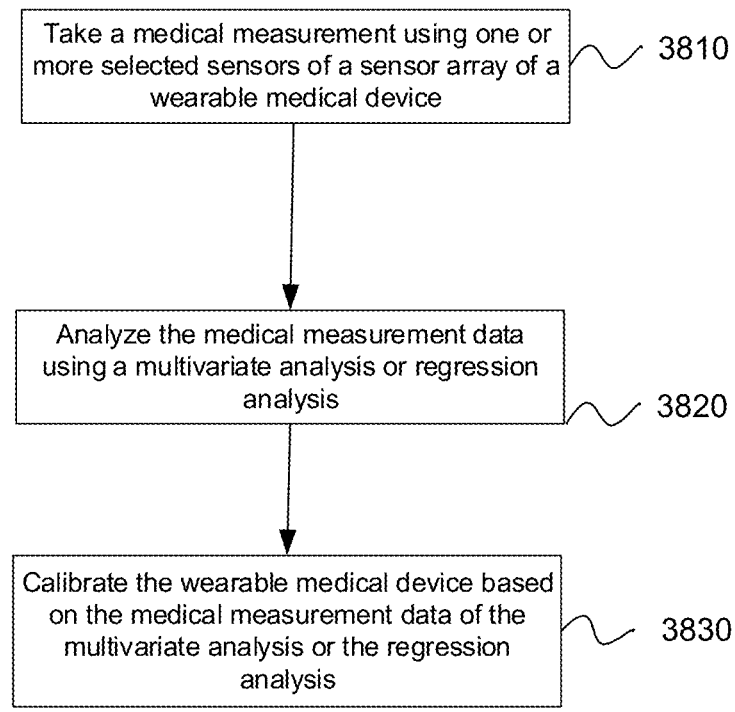
FIG. 38 depicts the functionality of another the computer circuitry of a wearable medical device that is operable calibrate sensors of the wearable medical device or medical measurements of the wearable medical device in accordance with an example.

FIG. 38 provides a flow chart 3800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more selected sensors of a sensor array of a wearable medical device, as in block 3810. The computer circuitry can be further configured to analyze the medical measurement data using a multivariate analysis or regression analysis, as in block 3820. The computer circuitry can also be configured to calibrate the wearable medical device based on the medical measurement data of the multivariate analysis or the regression analysis, as in block 3830.

Figure 39:
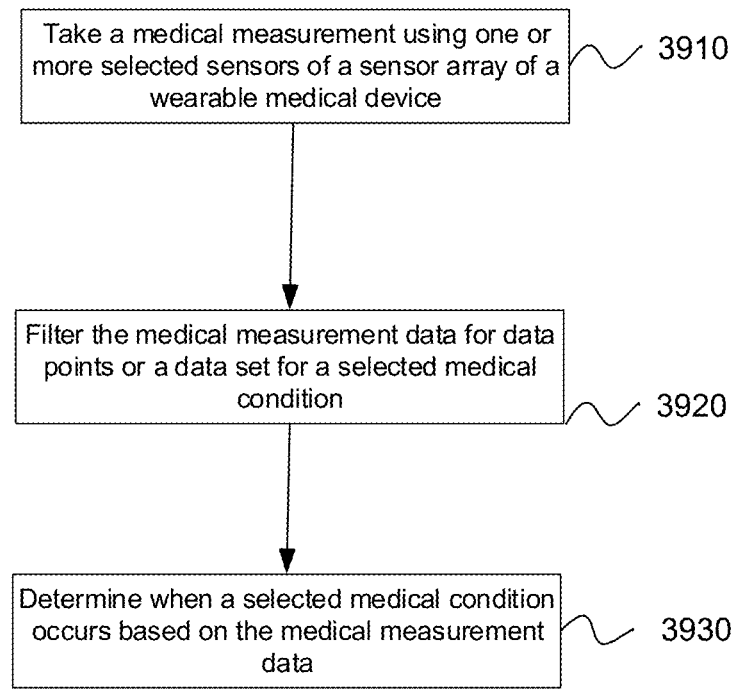
FIG. 39 depicts the functionality of another the computer circuitry of a wearable medical device that is operable calibrate sensors of the wearable medical device or medical measurements of the wearable medical device in accordance with an example.

FIG. 39 provides a flow chart 3900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more selected sensors of a sensor array of a wearable medical device, as in block 3910. The computer circuitry can be further configured to filter the medical measurement data for data points or a data set for a selected medical condition, as in block 3920. The computer circuitry can also be configured to determine when a selected medical condition occurs based on the medical measurement data, as in block 3930.

Figure 40:
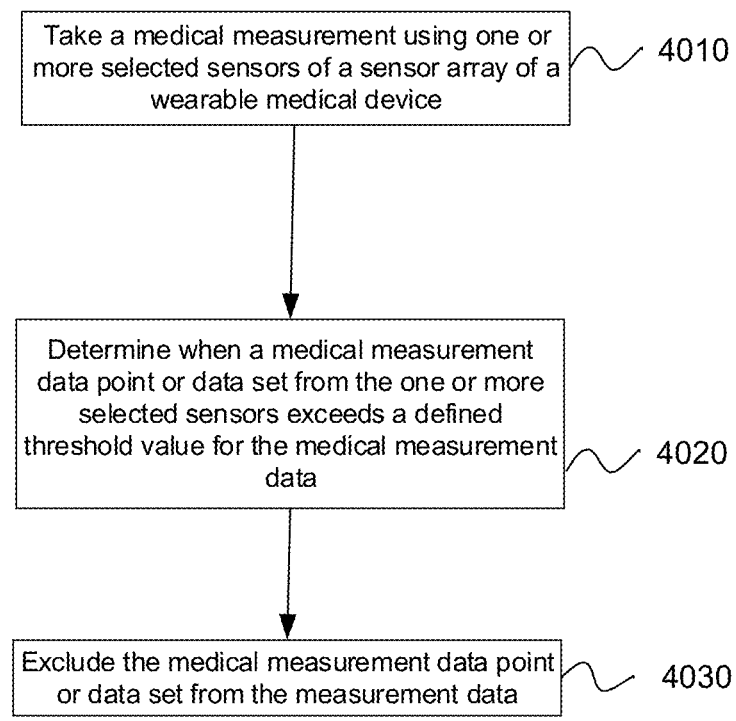
FIG. 40 depicts the functionality of another the computer circuitry of a wearable medical device that is operable calibrate sensors of the wearable medical device or medical measurements of the wearable medical device in accordance with an example.

FIG. 40 provides a flow chart 4000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more selected sensors of a sensor array of a wearable medical device, as in block 4010. The computer circuitry can be further configured to determine when a medical measurement data point or data set from the one or more selected sensors exceeds a defined threshold value for the medical measurement data, as in block 4020. The computer circuitry can also be configured to exclude the medical measurement data point or data set from the measurement data, as in block 4030.

Figure 41:
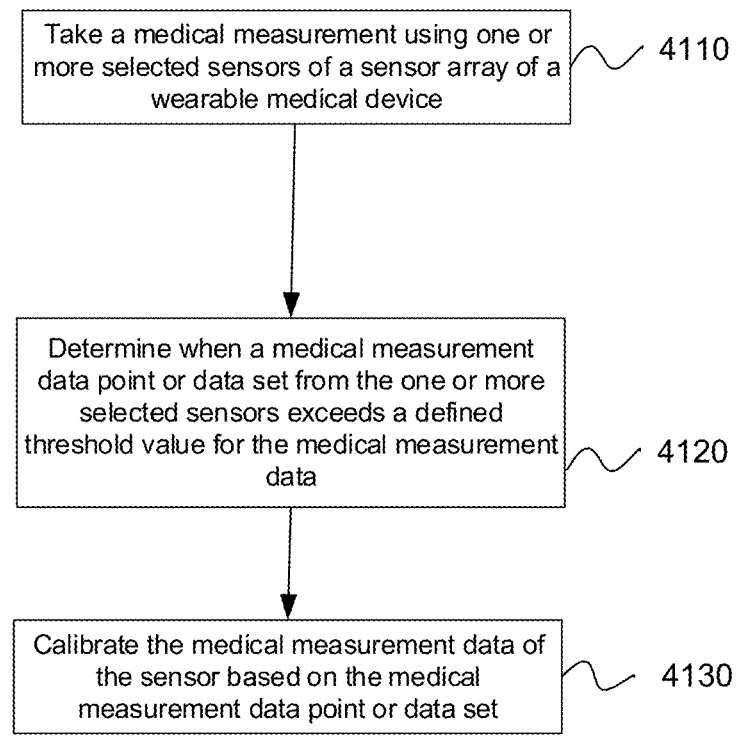
FIG. 41 depicts the functionality of another the computer circuitry of a wearable medical device that is operable calibrate sensors of the wearable medical device or medical measurements of the wearable medical device in accordance with an example.

FIG. 41 provides a flow chart 4100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more selected sensors of a sensor array of a wearable medical device, as in block 4110. The computer circuitry can be further configured to determine when a medical measurement data point or data set from the one or more selected sensors exceeds a defined threshold value for the medical measurement data, as in block 4120. The computer circuitry can also be configured to calibrate the medical measurement data of the sensor based on the medical measurement data point or data set, as in block 4130.

Figure 42:
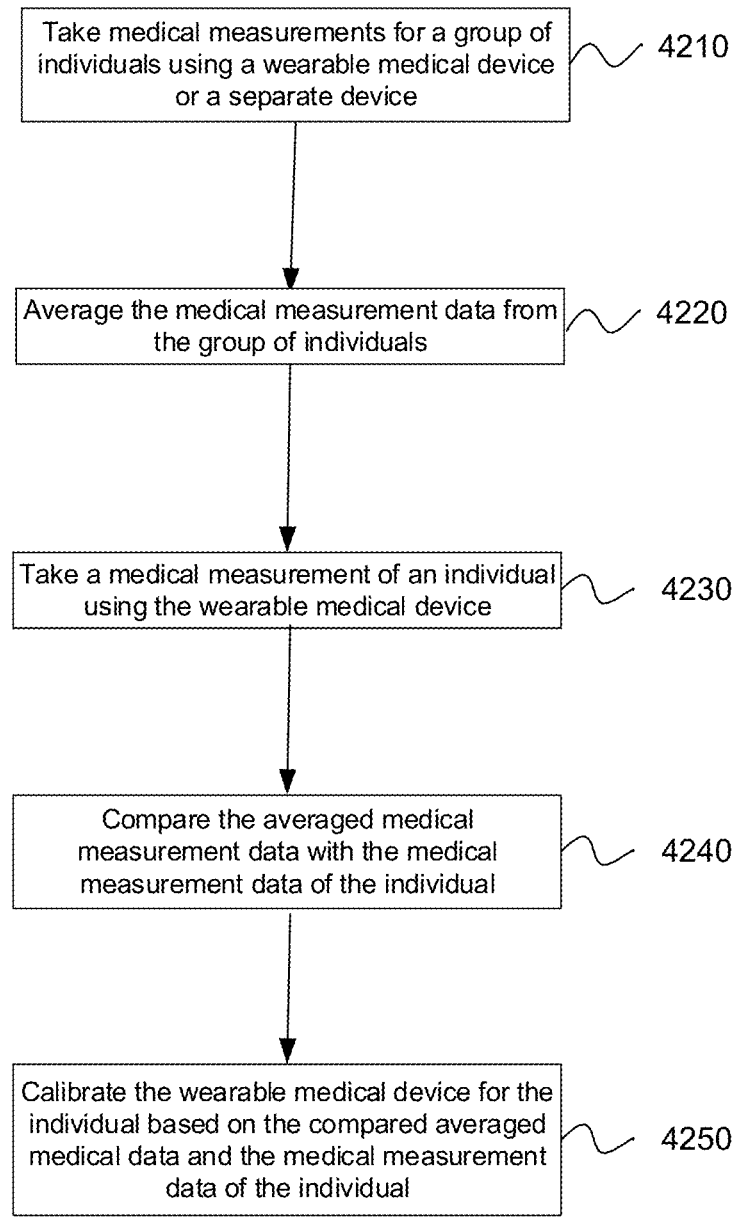
FIG. 42 depicts the functionality of another the computer circuitry of a wearable medical device that is operable calibrate sensors of the wearable medical device or medical measurements of the wearable medical device in accordance with an example.

FIG. 42 provides a flow chart 4200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take medical measurements for a group of individuals using a wearable medical device or a separate device, as in block 4210. The computer circuitry can be further configured to average the medical measurement data from the group of individuals, as in block 4220. The computer circuitry can also be configured to take a medical measurement of an individual using the wearable medical device, as in block 4230. The computer circuitry can also be configured to compare the averaged medical measurement data with the medical measurement data of the individual, as in block 4240. The computer circuitry can also be configured to calibrate the wearable medical device for the individual based on the compared averaged medical data and the medical measurement data of the individual, as in block 4250.

Figure 43:
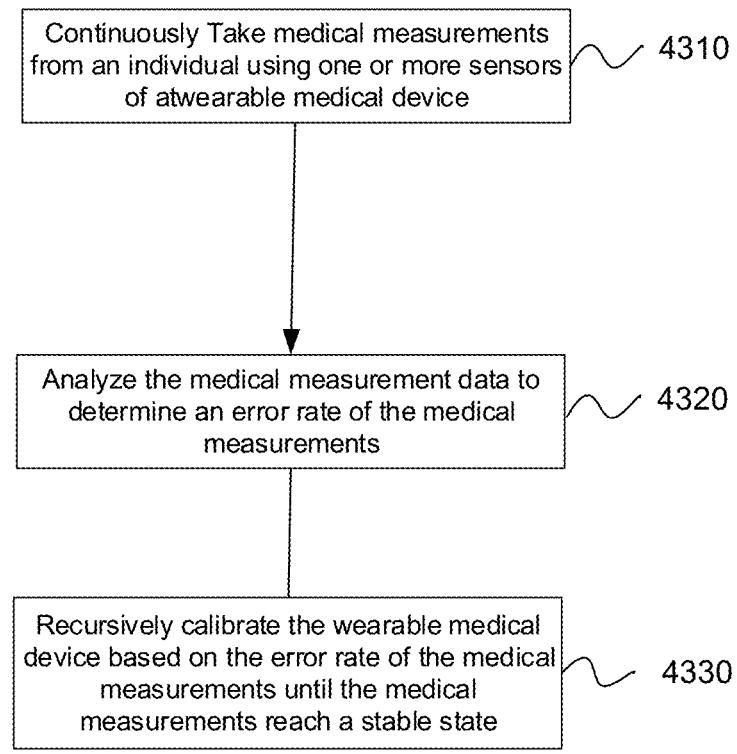
FIG. 43 depicts the functionality of another the computer circuitry of a wearable medical device that is operable calibrate sensors of the wearable medical device or medical measurements of the wearable medical device in accordance with an example.

FIG. 43 provides a flow chart 4300 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to continuously take medical measurements from an individual using one or more sensors of at wearable medical device, as in block 4310. The computer circuitry can be further configured to analyze the medical measurement data to determine an error rate of the medical measurements, as in block 4320. The computer circuitry can also be configured to recursively calibrate the wearable medical device based on the error rate of the medical measurements until the medical measurements reach a stable state, as in block 4330.

Figure 44:
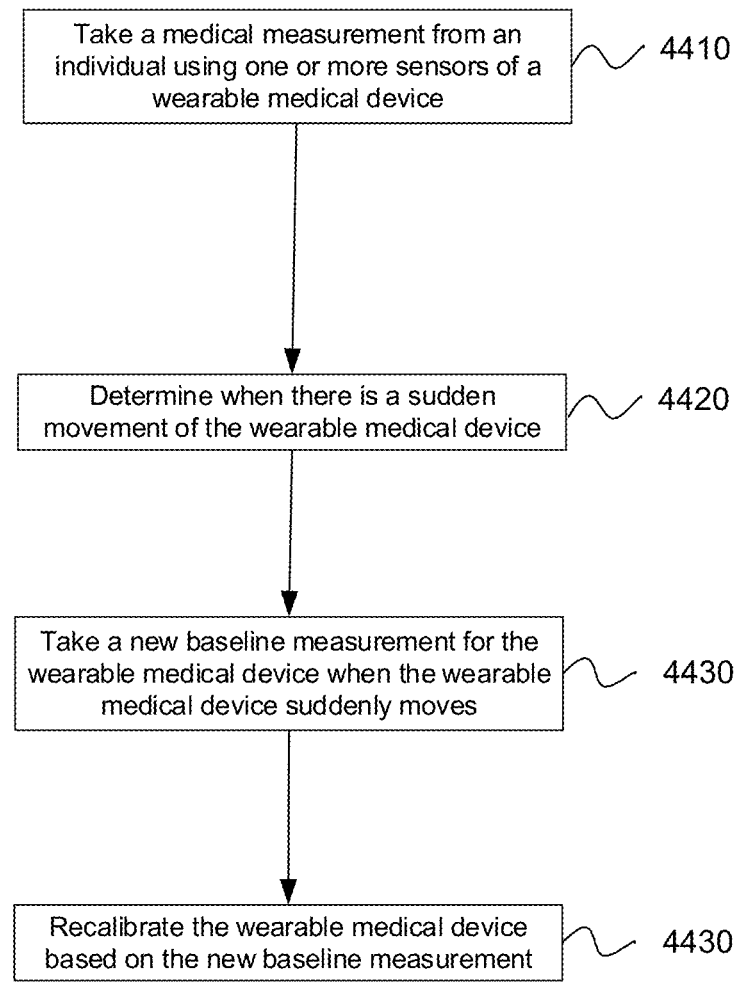
FIG. 44 depicts the functionality of another the computer circuitry of a wearable medical device that is operable calibrate sensors of the wearable medical device or medical measurements of the wearable medical device in accordance with an example.

FIG. 44 provides a flow chart 4400 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement from an individual using one or more sensors of a wearable medical device, as in block 4410. The computer circuitry can be further configured to determine when there is a sudden movement of the wearable medical device, as in block 4420. The computer circuitry can also be configured to take a new baseline measurement for the wearable medical device when the wearable medical device suddenly moves, as in block 4430. The computer circuitry can also be configured to recalibrate the wearable medical device based on the new baseline measurement, as in block 4440.

Figure 45:
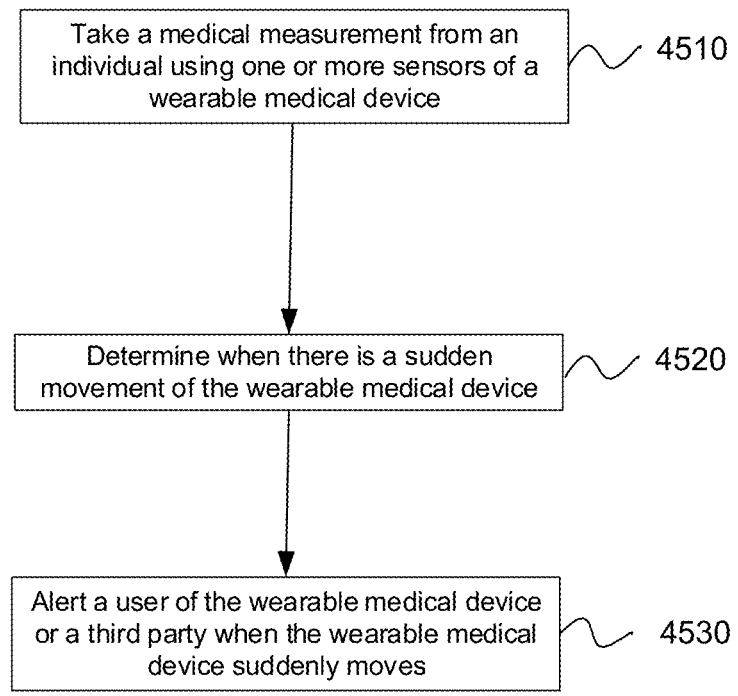
FIG. 45 depicts the functionality of another the computer circuitry of a wearable medical device that is operable calibrate sensors of the wearable medical device or medical measurements of the wearable medical device in accordance with an example.

FIG. 45 provides a flow chart 4500 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement from an individual using one or more sensors of a wearable medical device, as in block 4510. The computer circuitry can be further configured to determine when there is a sudden movement of the wearable medical device, as in block 4520. The computer circuitry can also be configured to alert a user of the wearable medical device or a third party when the wearable medical device suddenly moves, as in block 4530.

Figure 46:
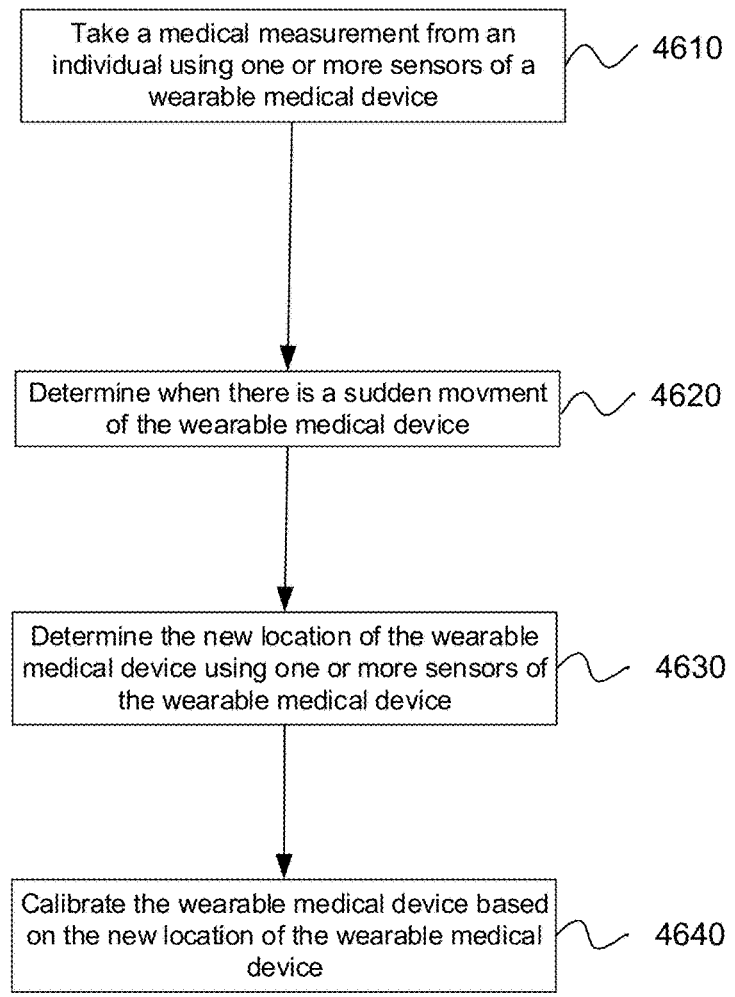
FIG. 46 depicts the functionality of another the computer circuitry of a wearable medical device that is operable calibrate sensors of the wearable medical device or medical measurements of the wearable medical device in accordance with an example.

FIG. 46 provides a flow chart 4600 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement from an individual using one or more sensors of a wearable medical device, as in block 4610. The computer circuitry can be further configured to determine when there is a sudden movement of the wearable medical device, as in block 4620. The computer circuitry can also be configured to determine the new location of the wearable medical device using one or more sensors of the wearable medical device, as in block 4630. The computer circuitry can also be configured to calibrate the wearable medical device based on the new location of the wearable medical device, as in block 4640.

Figure 47:
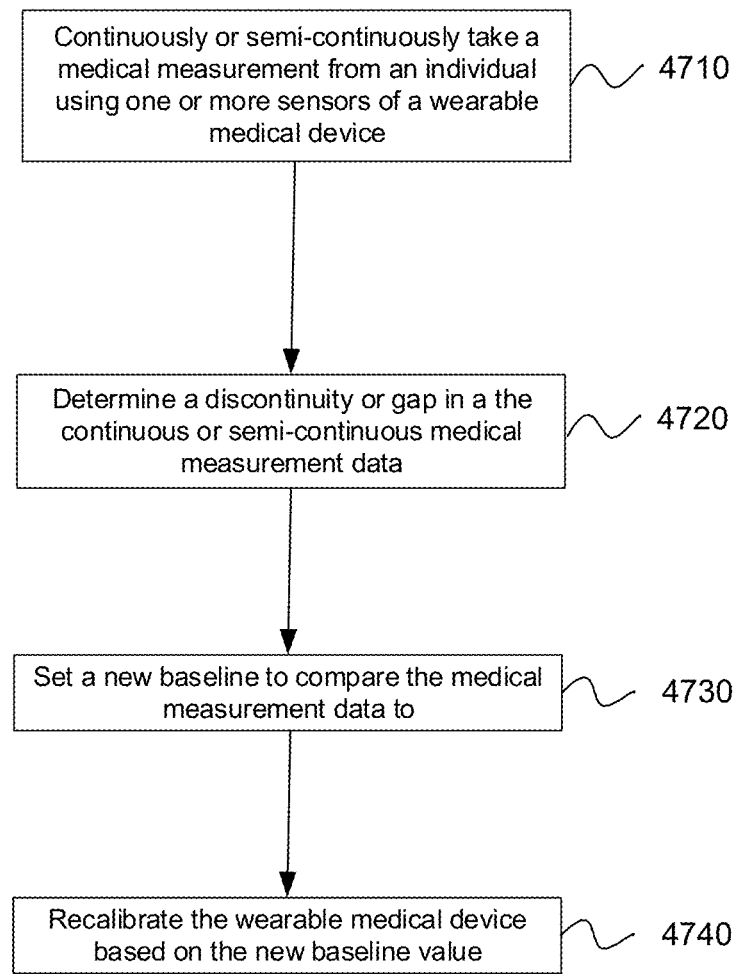
FIG. 47 depicts the functionality of another the computer circuitry of a wearable medical device that is operable calibrate sensors of the wearable medical device or medical measurements of the wearable medical device in accordance with an example.

FIG. 47 provides a flow chart 4700 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to continuously or semi-continuously take a medical measurement from an individual using one or more sensors of a wearable medical device, as in block 4710. The computer circuitry can be further configured to determine a discontinuity or gap in the continuous or semi-continuous medical measurement data, as in block 4720. The computer circuitry can also be configured to set a new baseline to compare the medical measurement data to, as in block 4730. The computer circuitry can also be configured to recalibrate the wearable medical device based on the new baseline value, as in block 4740.

Figure 48:
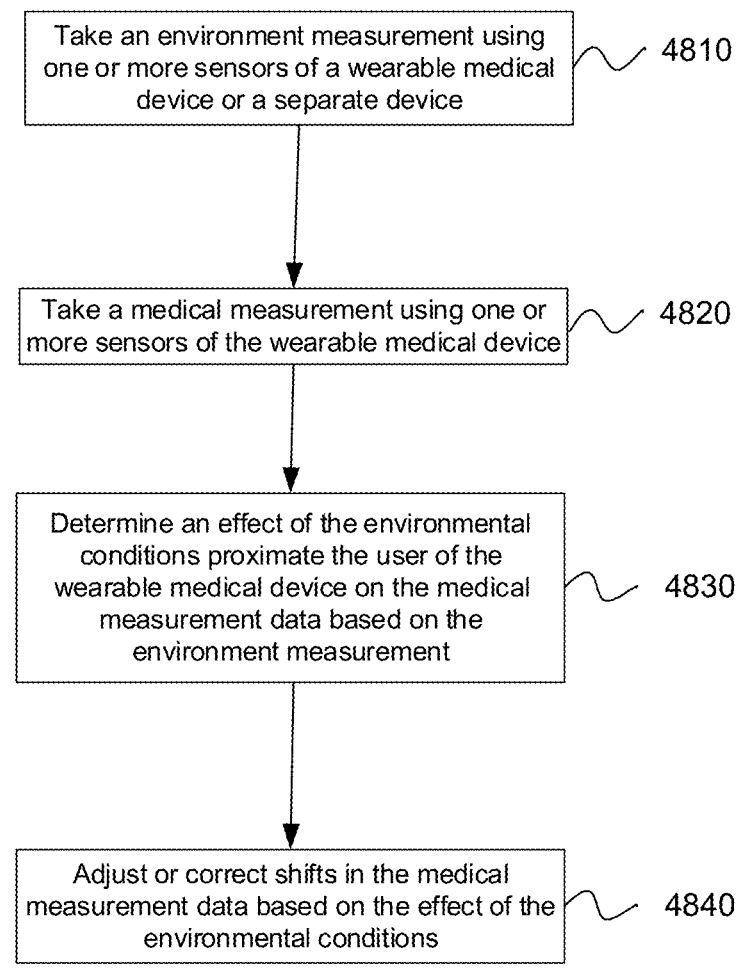
FIG. 48 depicts the functionality of another the computer circuitry of a wearable medical device that is operable calibrate sensors of the wearable medical device or medical measurements of the wearable medical device in accordance with an example.

FIG. 48 provides a flow chart 4800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take an environment measurement using one or more sensors of a wearable medical device or a separate device, as in block 4810. The computer circuitry can be further configured to take a medical measurement using one or more sensors of the wearable medical device, as in block 4820. The computer circuitry can also be configured to determine an effect of the environmental conditions proximate the user of the wearable medical device on the medical measurement data based on the environment measurement, as in block 4830. The computer circuitry can also be configured to adjust or correct shifts in the medical measurement data based on the effect of the environmental conditions, as in block 4840.

Figure 49:
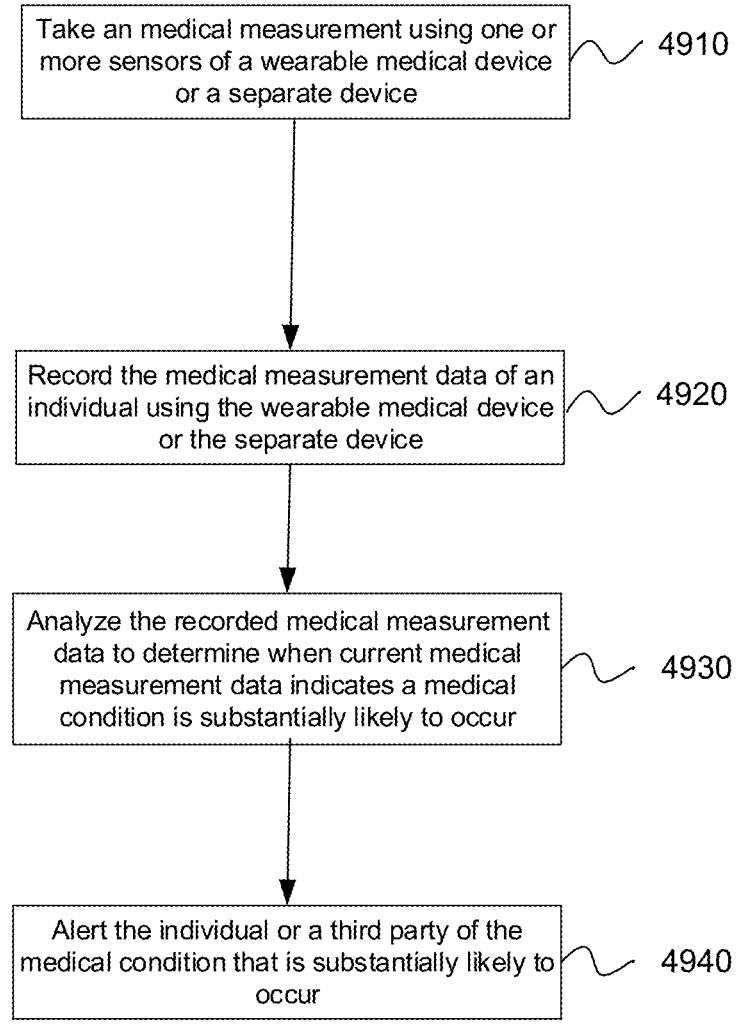
FIG. 49 depicts the functionality of another the computer circuitry of a wearable medical device that is operable calibrate sensors of the wearable medical device or medical measurements of the wearable medical device in accordance with an example.

FIG. 49 provides a flow chart 4900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement using one or more sensors of a wearable medical device or a separate device, as in block 4910. The computer circuitry can be further configured to record the medical measurement data of an individual using the wearable medical device or the separate device, as in block 4920. The computer circuitry can also be configured to analyze the recorded medical measurement data to determine when current medical measurement data indicates a medical condition is substantially likely to occur, as in block 4930. The computer circuitry can also be configured to alert the individual or a third party of the medical condition that is substantially likely to occur, as in block 4940.

Figure 50:
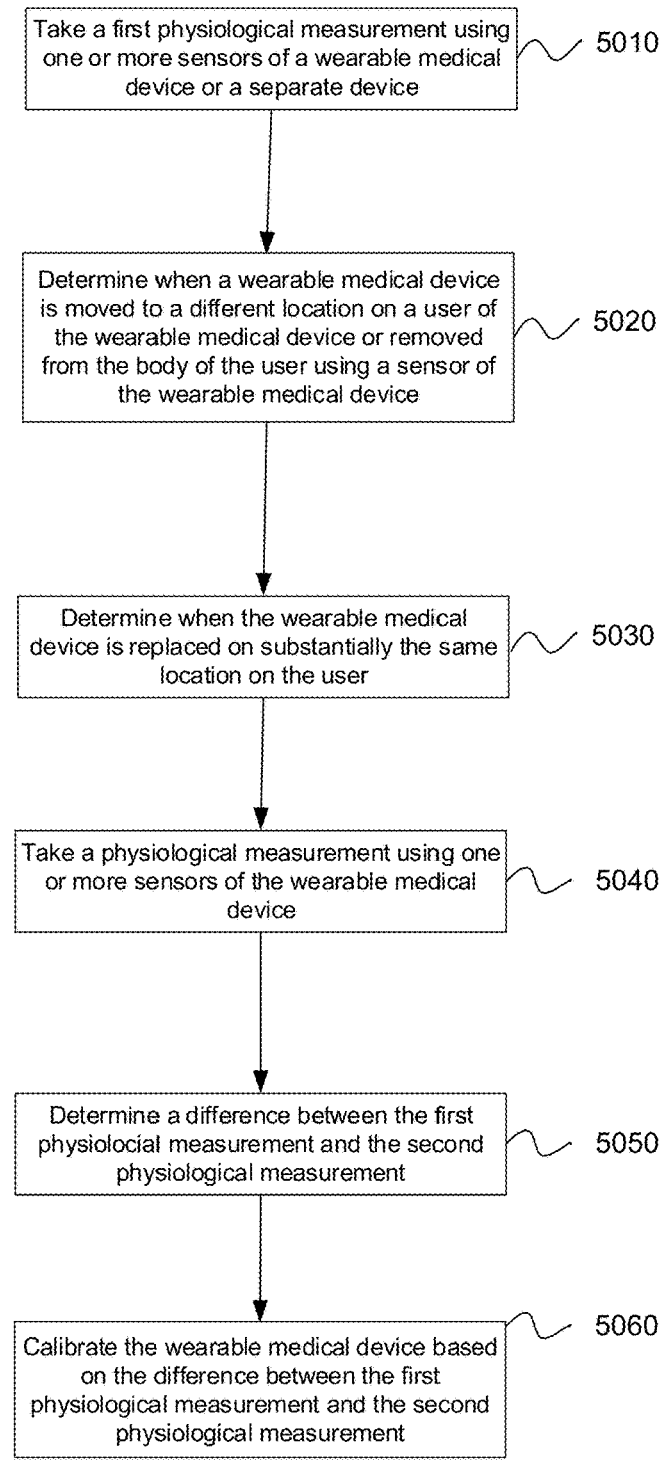
FIG. 50 depicts the functionality of another the computer circuitry of a wearable medical device that is operable calibrate sensors of the wearable medical device or medical measurements of the wearable medical device in accordance with an example.

FIG. 50 provides a flow chart 5000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a first physiological measurement using one or more sensors of a wearable medical device or a separate device, as in block 5010. The computer circuitry can be further configured to determine when a wearable medical device is moved to a different location on a user of the wearable medical device or removed from the body of the user using a sensor of the wearable medical device, as in block 5020. The computer circuitry can also be configured to determine when the wearable medical device is replaced on substantially the same location on the user, as in block 5030. The computer circuitry can also be configured to take a physiological measurement using one or more sensors of the wearable medical device, as in block 5040. The computer circuitry can also be configured to determine a difference between the first physiological measurement and the second physiological measurement, as in block 5050. The computer circuitry can also be configured to take a physiological measurement using one or more sensors of the wearable medical device, as in block 5060.

Figure 51:
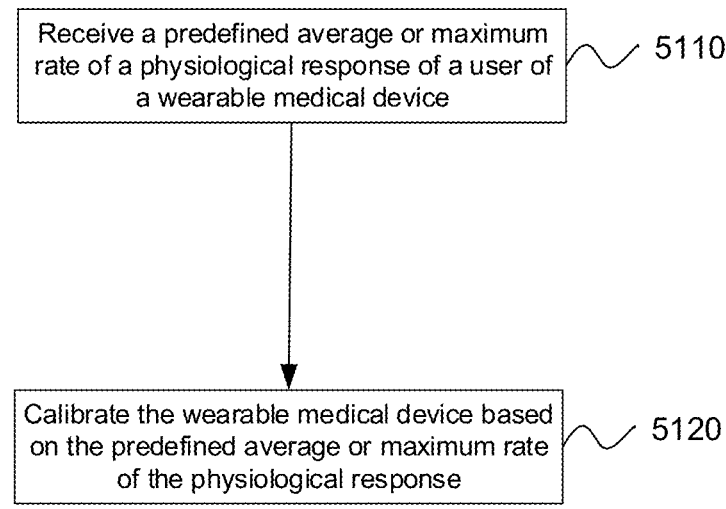
FIG. 51 depicts the functionality of another the computer circuitry of a wearable medical device that is operable calibrate sensors of the wearable medical device or medical measurements of the wearable medical device in accordance with an example.

FIG. 51 provides a flow chart 5100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive a predefined average or maximum rate of a physiological response of a user of a wearable medical device, as in block 5110. The computer circuitry can be further configured to calibrate the wearable medical device based on the predefined average or maximum rate of the physiological response, as in block 5120.

Figure 52:
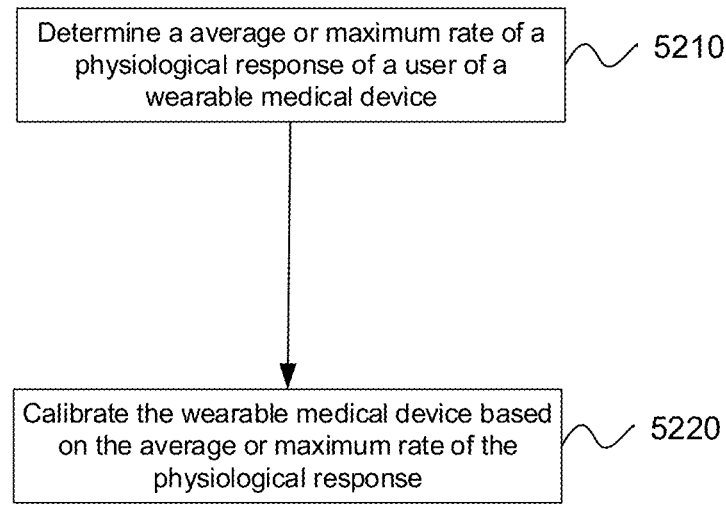
FIG. 52 depicts the functionality of another the computer circuitry of a wearable medical device that is operable calibrate sensors of the wearable medical device or medical measurements of the wearable medical device in accordance with an example.

FIG. 52 provides a flow chart 5200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine an average or maximum rate of a physiological response of a user of a wearable medical device, as in block 5210. The computer circuitry can be further configured to calibrate the wearable medical device based on the average or maximum rate of the physiological response, as in block 5220.

Figure 53:
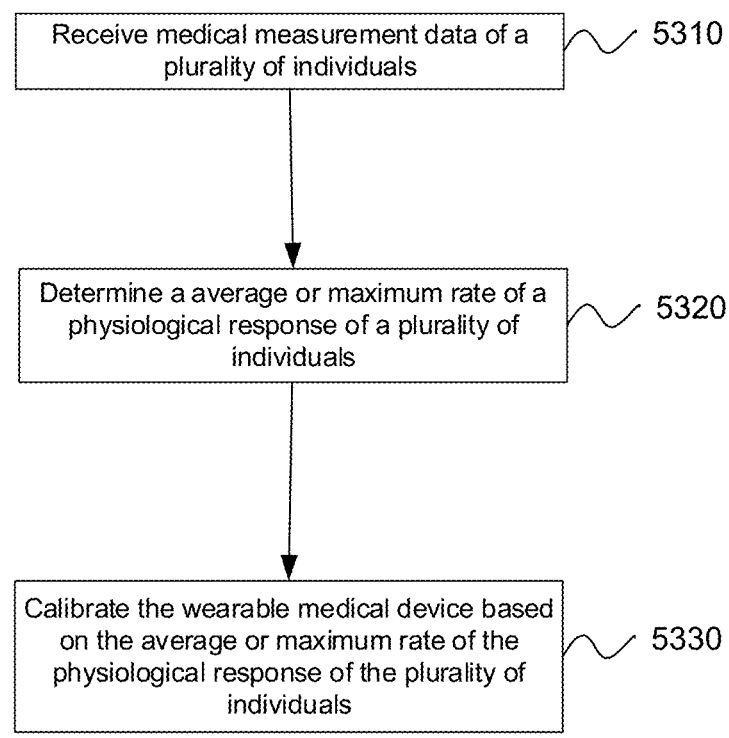
FIG. 53 depicts the functionality of another the computer circuitry of a wearable medical device that is operable calibrate sensors of the wearable medical device or medical measurements of the wearable medical device in accordance with an example.

FIG. 53 provides a flow chart 5300 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive medical measurement data of a plurality of individuals, as in block 5310. The computer circuitry can be further configured to determine an average or maximum rate of a physiological response of a plurality of individuals, as in block 5320. The computer circuitry can be further configured to calibrate the wearable medical device based on the average or maximum rate of the physiological response of the plurality of individuals, as in block 5330.

Figure 54:
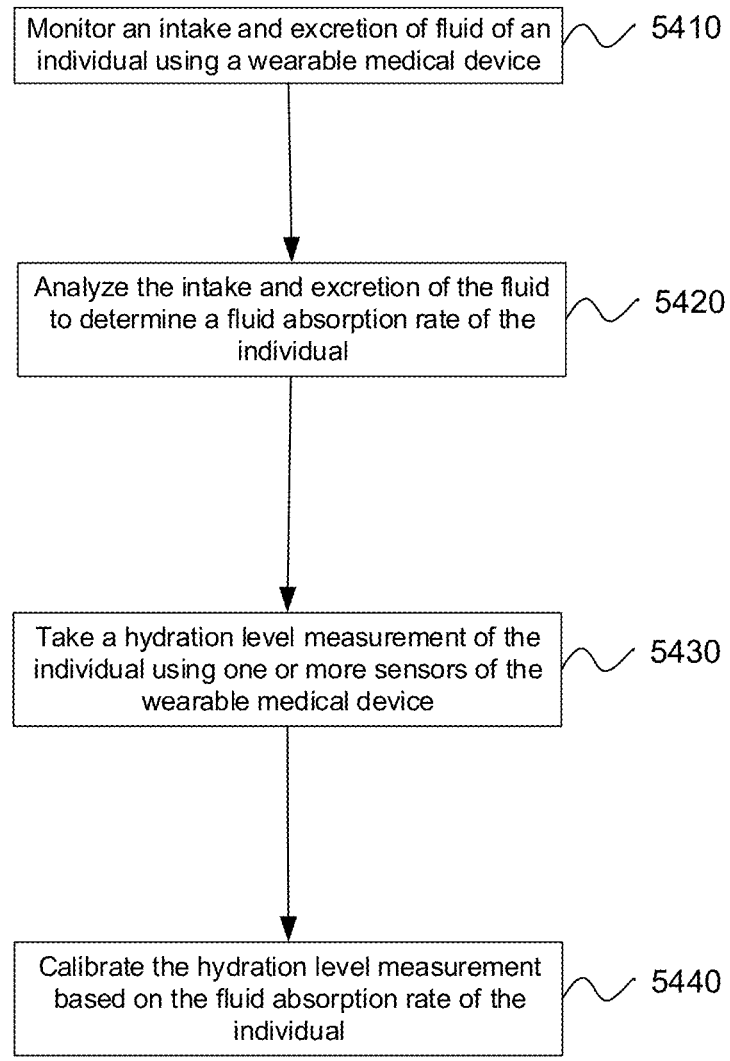
FIG. 54 depicts the functionality of another the computer circuitry of a wearable medical device that is operable calibrate sensors of the wearable medical device or medical measurements of the wearable medical device in accordance with an example.

FIG. 54 provides a flow chart 5400 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to monitor an intake and excretion of fluid of an individual using a wearable medical device, as in block 5410. The computer circuitry can be further configured to analyze the intake and excretion of the fluid to determine a fluid absorption rate of the individual, as in block 5420. The computer circuitry can be further configured to take a hydration level measurement of the individual using one or more sensors of the wearable medical device, as in block 5430. The computer circuitry can be further configured to calibrate the hydration level measurement based on the fluid absorption rate of the individual, as in block 5440.

Figure 55:
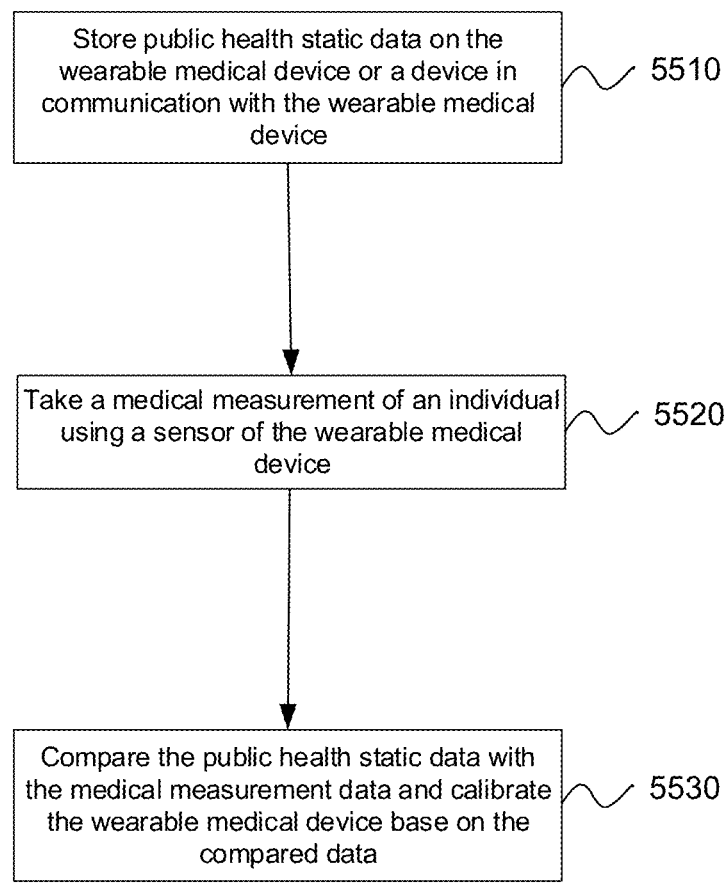
FIG. 55 depicts the functionality of another the computer circuitry of a wearable medical device that is operable calibrate sensors of the wearable medical device or medical measurements of the wearable medical device in accordance with an example.

FIG. 55 provides a flow chart 5500 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to store public health static data on the wearable medical device or a device in communication with the wearable medical device, as in block 5510. The computer circuitry can be further configured to take a medical measurement of an individual using a sensor of the wearable medical device, as in block 5520. The computer circuitry can be further configured to compare the public health static data with the medical measurement data and calibrate the wearable medical device base on the compared data, as in block 5530.

Figure 56:
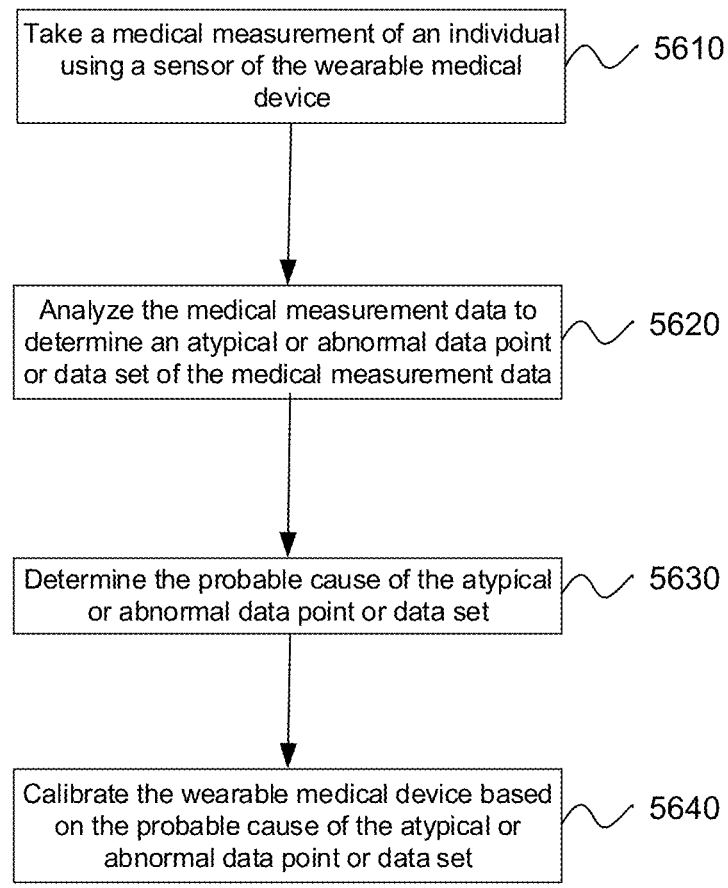
FIG. 56 depicts the functionality of another the computer circuitry of a wearable medical device that is operable calibrate sensors of the wearable medical device or medical measurements of the wearable medical device in accordance with an example.

FIG. 56 provides a flow chart 5600 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement of an individual using a sensor of the wearable medical device, as in block 5610. The computer circuitry can be further configured to analyze the medical measurement data to determine an atypical or abnormal data point or data set of the medical measurement data, as in block 5620. The computer circuitry can be further configured to determine the probable cause of the atypical or abnormal data point or data set, as in block 5630. The computer circuitry can be further configured to calibrate the wearable medical device based on the probable cause of the atypical or abnormal data point or data set, as in block 5640.

Figure 57:
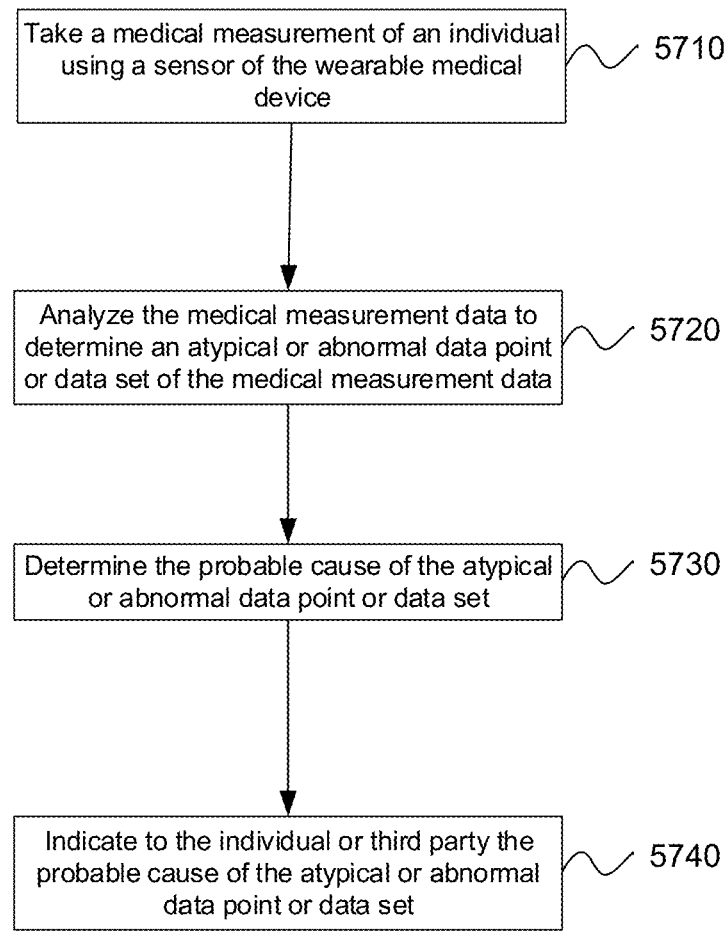
FIG. 57 depicts the functionality of another the computer circuitry of a wearable medical device that is operable calibrate sensors of the wearable medical device or medical measurements of the wearable medical device in accordance with an example.

FIG. 57 provides a flow chart 5700 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a medical measurement of an individual using a sensor of the wearable medical device, as in block 5710. The computer circuitry can be further configured to analyze the medical measurement data to determine an atypical or abnormal data point or data set of the medical measurement data, as in block 5720. The computer circuitry can be further configured to determine the probable cause of the atypical or abnormal data point or data set, as in block 5730. The computer circuitry can be further configured to indicate to the individual or third party the probable cause of the atypical or abnormal data point or data set, as in block 5740.

Figure 58:
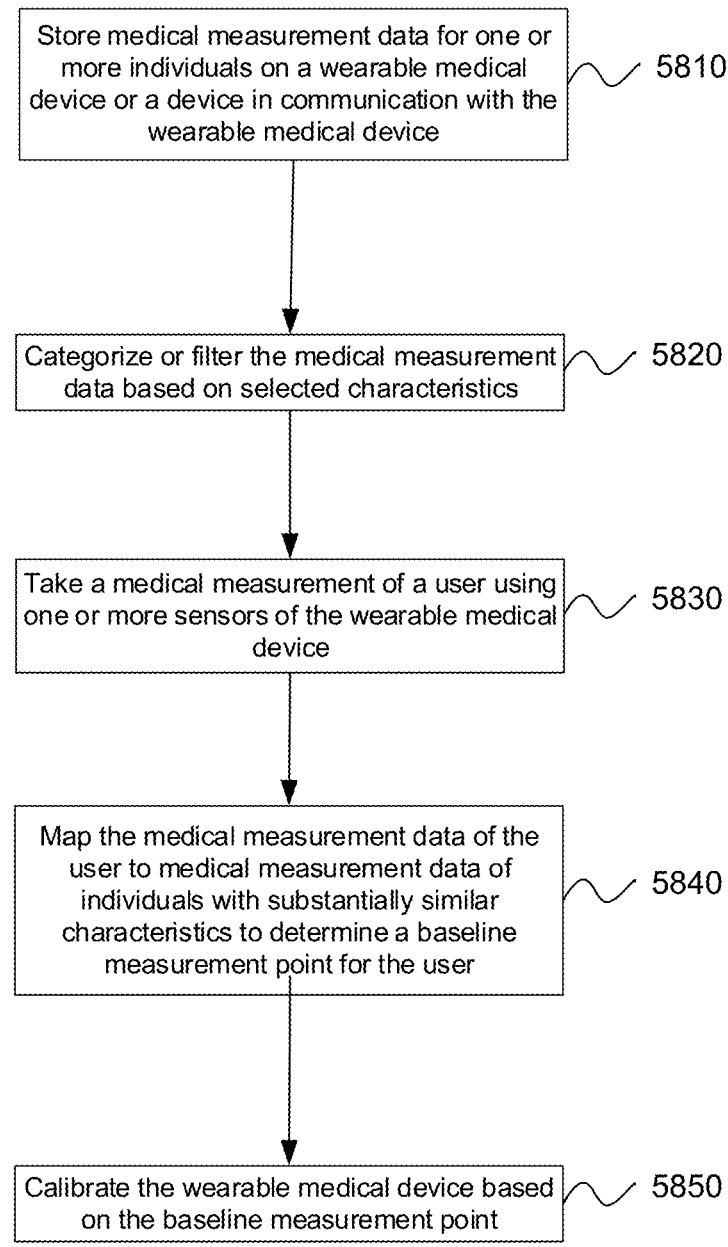
FIG. 58 depicts the functionality of another the computer circuitry of a wearable medical device that is operable calibrate sensors of the wearable medical device or medical measurements of the wearable medical device in accordance with an example.

FIG. 58 provides a flow chart 5800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to store medical measurement data for one or more individuals on a wearable medical device or a device in communication with the wearable medical device, as in block 5810. The computer circuitry can be further configured to categorize or filter the medical measurement data based on selected characteristics, as in block 5820. The computer circuitry can be further configured to take a medical measurement of a user using one or more sensors of the wearable medical device, as in block 5830. The computer circuitry can be further configured to map the medical measurement data of the user to medical measurement data of individuals with substantially similar characteristics to determine a baseline measurement point for the user, as in block 5840. The computer circuitry can be further configured to calibrate the wearable medical device based on the baseline measurement point, as in block 5850.

Figure 59:
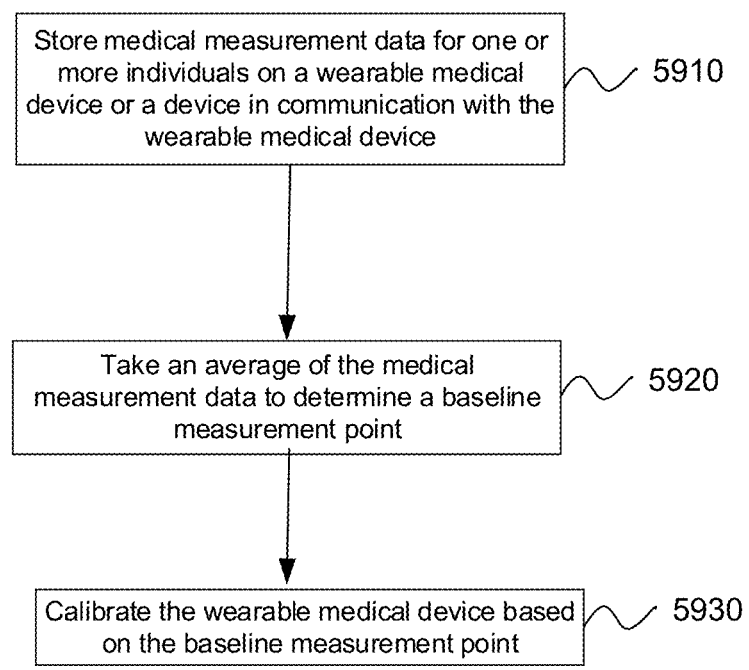
FIG. 59 depicts the functionality of another the computer circuitry of a wearable medical device that is operable calibrate sensors of the wearable medical device or medical measurements of the wearable medical device in accordance with an example.

FIG. 59 provides a flow chart 5900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to store medical measurement data for one or more individuals on a wearable medical device or a device in communication with the wearable medical device, as in block 5910. The computer circuitry can be further configured to take an average of the medical measurement data to determine a baseline measurement point, as in block 5920. The computer circuitry can be further configured to calibrate the wearable medical device based on the baseline measurement point, as in block 5930.

Figure 60:
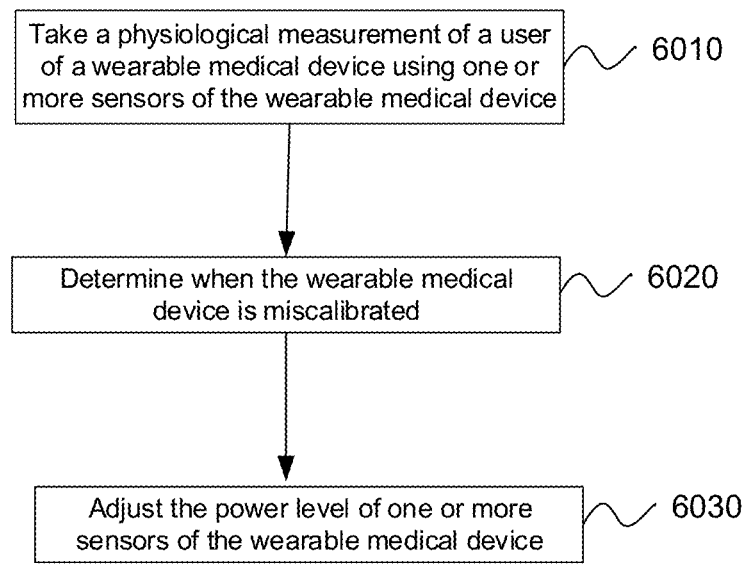
FIG. 60 depicts the functionality of another the computer circuitry of a wearable medical device that is operable calibrate sensors of the wearable medical device or medical measurements of the wearable medical device in accordance with an example.

FIG. 60 provides a flow chart 6000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of a user of a wearable medical device using one or more sensors of the wearable medical device, as in block 6010. The computer circuitry can be further configured to determine when the wearable medical device is miscalibrated, as in block 6020. The computer circuitry can be further configured to adjust the power level of one or more sensors of the wearable medical device, as in block 6030.

Figure 61:
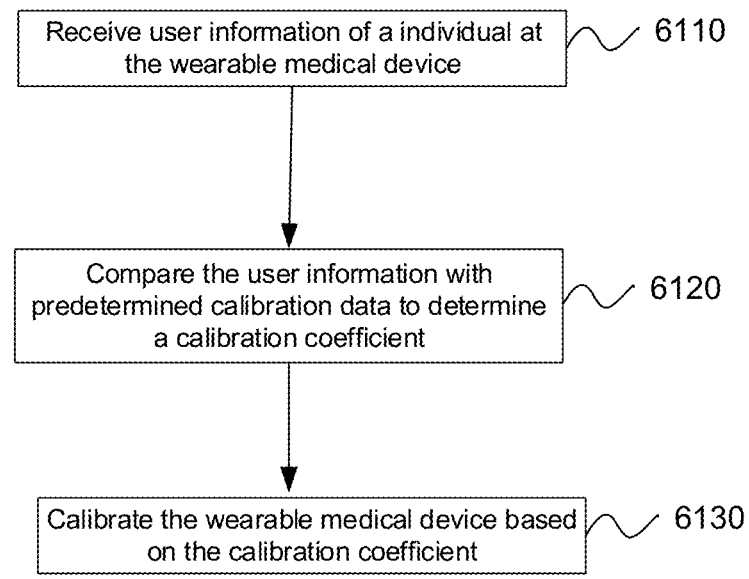
FIG. 61 depicts the functionality of another the computer circuitry of a wearable medical device that is operable calibrate sensors of the wearable medical device or medical measurements of the wearable medical device in accordance with an example.

FIG. 61 provides a flow chart 6100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive user information of an individual at the wearable medical device, as in block 6110. The computer circuitry can be further configured to compare the user information with predetermined calibration data to determine a calibration coefficient, as in block 6120. The computer circuitry can be further configured to calibrate the wearable medical device based on the calibration coefficient, as in block 6130.

Figure 62:
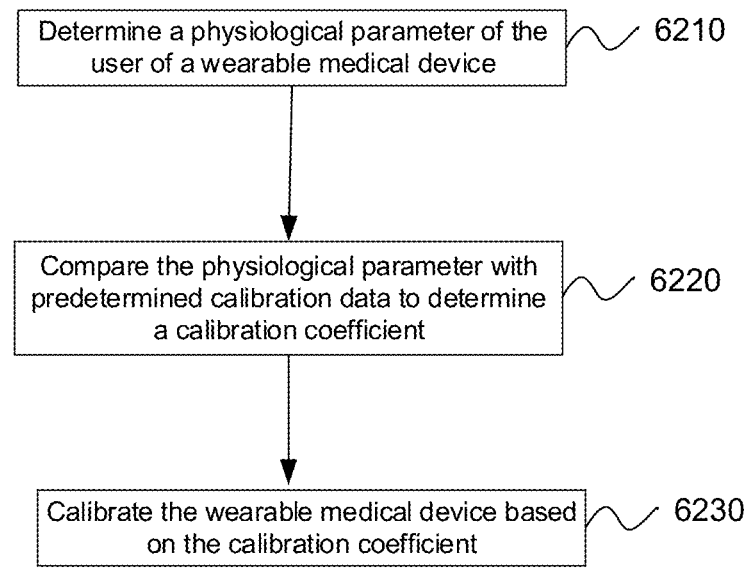
FIG. 62 depicts the functionality of another the computer circuitry of a wearable medical device that is operable calibrate sensors of the wearable medical device or medical measurements of the wearable medical device in accordance with an example.

FIG. 62 provides a flow chart 6200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine a physiological parameter of the user of a wearable medical device, as in block 6210. The computer circuitry can be further configured to compare the physiological parameter with predetermined calibration data to determine a calibration coefficient, as in block 6220. The computer circuitry can be further configured to calibrate the wearable medical device based on the calibration coefficient, as in block 6230.

Figure 63:
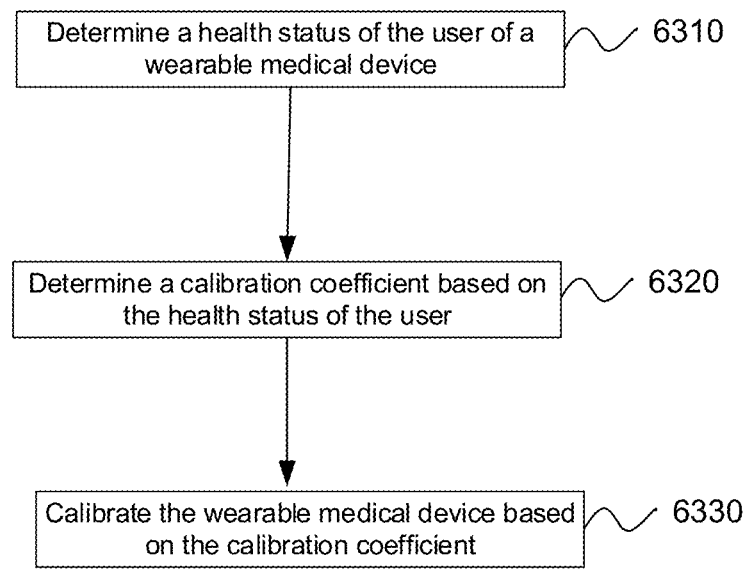
FIG. 63 depicts the functionality of another the computer circuitry of a wearable medical device that is operable calibrate sensors of the wearable medical device or medical measurements of the wearable medical device in accordance with an example.

FIG. 63 provides a flow chart 6300 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine a health status of the user of a wearable medical device, as in block 6310. The computer circuitry can be further configured to determine a calibration coefficient based on the health status of the user, as in block 6320. The computer circuitry can be further configured to calibrate the wearable medical device based on the calibration coefficient, as in block 6330.

Figure 64:
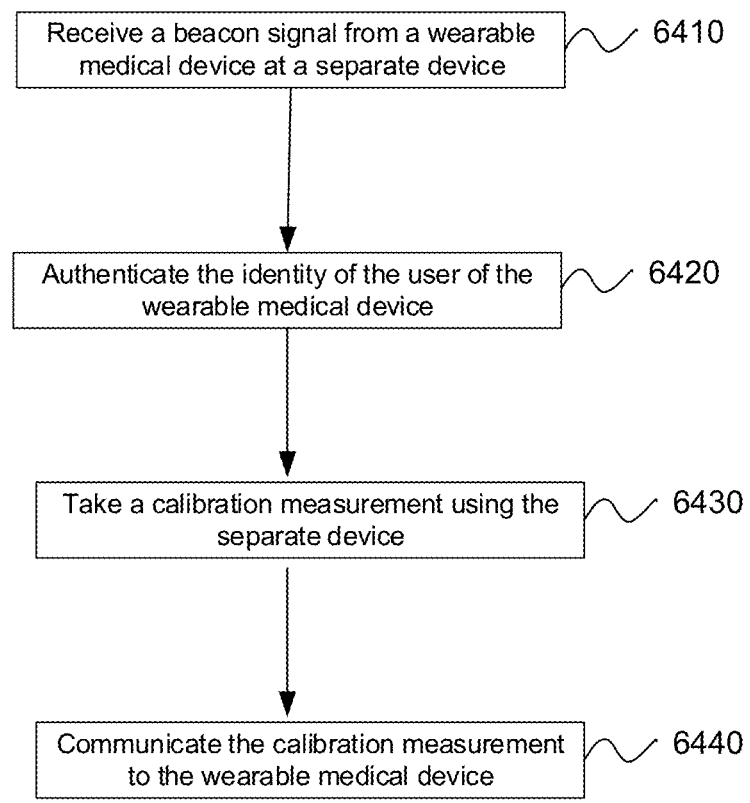
FIG. 64 depicts the functionality of another the computer circuitry of a wearable medical device that is operable calibrate sensors of the wearable medical device or medical measurements of the wearable medical device in accordance with an example.

FIG. 64 provides a flow chart 6400 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive a beacon signal from a wearable medical device at a separate device, as in block 6410. The computer circuitry can be further configured to authenticate the identity of the user of the wearable medical device, as in block 6420. The computer circuitry can be further configured to take a calibration measurement using the separate device, as in block 6430. The computer circuitry can be further configured to communicate the calibration measurement to the wearable medical device, as in block 6440.

Figure 65:
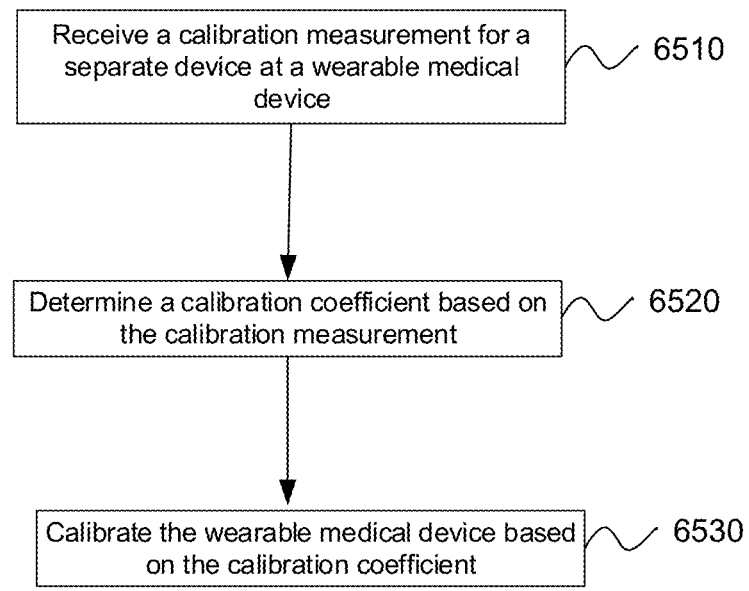
FIG. 65 depicts the functionality of another the computer circuitry of a wearable medical device that is operable calibrate sensors of the wearable medical device or medical measurements of the wearable medical device in accordance with an example.

FIG. 65 provides a flow chart 6500 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to receive a calibration measurement for a separate device at a wearable medical device, as in block 6510. The computer circuitry can be further configured to determine a calibration coefficient based on the calibration measurement, as in block 6520. The computer circuitry can be further configured to calibrate the wearable medical device based on the calibration coefficient, as in block 6530.

Figure 66:
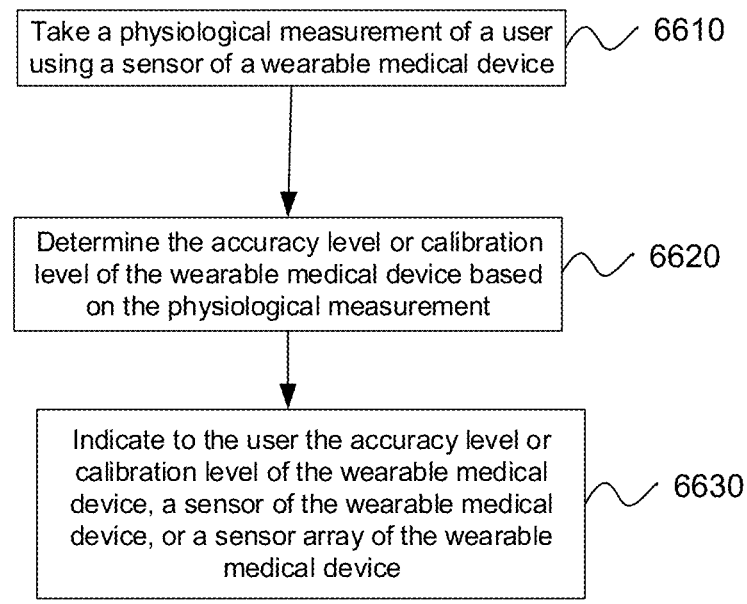
FIG. 66 depicts the functionality of another the computer circuitry of a wearable medical device that is operable calibrate sensors of the wearable medical device or medical measurements of the wearable medical device in accordance with an example.

FIG. 66 provides a flow chart 6600 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of a user using a sensor of a wearable medical device, as in block 6610. The computer circuitry can be further configured to determine the accuracy level or calibration level of the wearable medical device based on the physiological measurement, as in block 6620. The computer circuitry can be further configured to indicate to the user the accuracy level or calibration level of the wearable medical device, a sensor of the wearable medical device, or a sensor array of the wearable medical device, as in block 6630.

Figure 67:
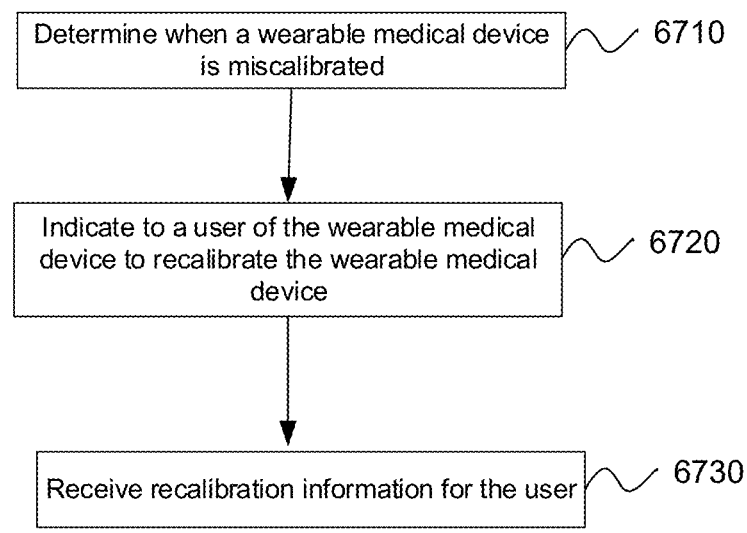
FIG. 67 depicts the functionality of another the computer circuitry of a wearable medical device that is operable calibrate sensors of the wearable medical device or medical measurements of the wearable medical device in accordance with an example.

FIG. 67 provides a flow chart 6700 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to determine when a wearable medical device is miscalibrated, as in block 6710. The computer circuitry can be further configured to indicate to a user of the wearable medical device to recalibrate the wearable medical device, as in block 6720. The computer circuitry can be further configured to receive recalibration information for the user, as in block 6730.

Figure 68:
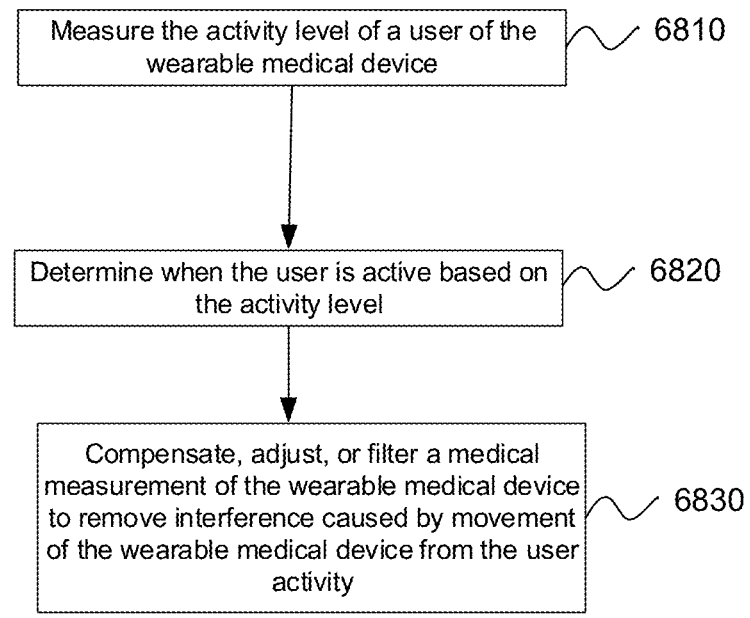
FIG. 68 depicts the functionality of another the computer circuitry of a wearable medical device that is operable calibrate sensors of the wearable medical device or medical measurements of the wearable medical device in accordance with an example.

FIG. 68 provides a flow chart 6800 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to measure the activity level of a user of the wearable medical device, as in block 6810. The computer circuitry can be further configured to determine when the user is active based on the activity level, as in block 6820. The computer circuitry can be further configured to compensate, adjust, or filter a medical measurement of the wearable medical device to remove interference caused by movement of the wearable medical device from the user activity, as in block 6830.

Figure 69:
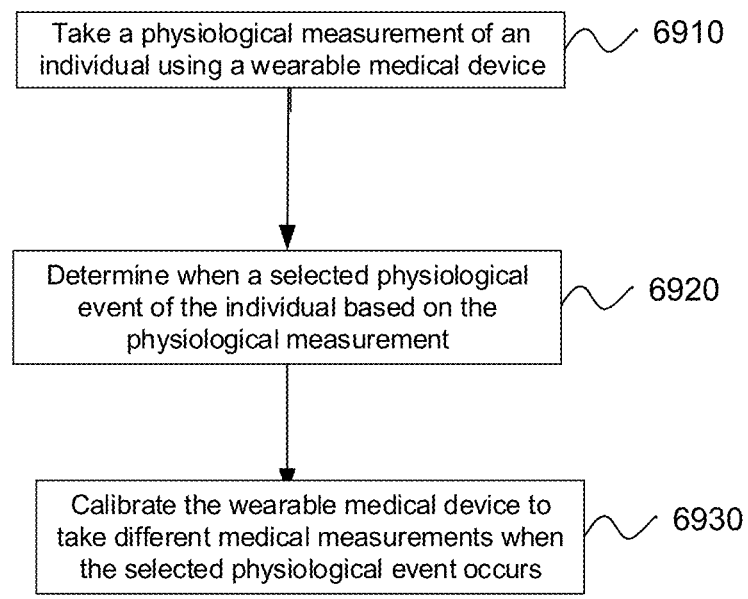
FIG. 69 depicts the functionality of another the computer circuitry of a wearable medical device that is operable calibrate sensors of the wearable medical device or medical measurements of the wearable medical device in accordance with an example.

FIG. 69 provides a flow chart 6900 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of an individual using a wearable medical device, as in block 6910. The computer circuitry can be further configured to determine when a selected physiological event of the individual based on the physiological measurement, as in block 6920. The computer circuitry can be further configured to calibrate the wearable medical device to take different medical measurements when the selected physiological event occurs, as in block 6930.

Figure 70:
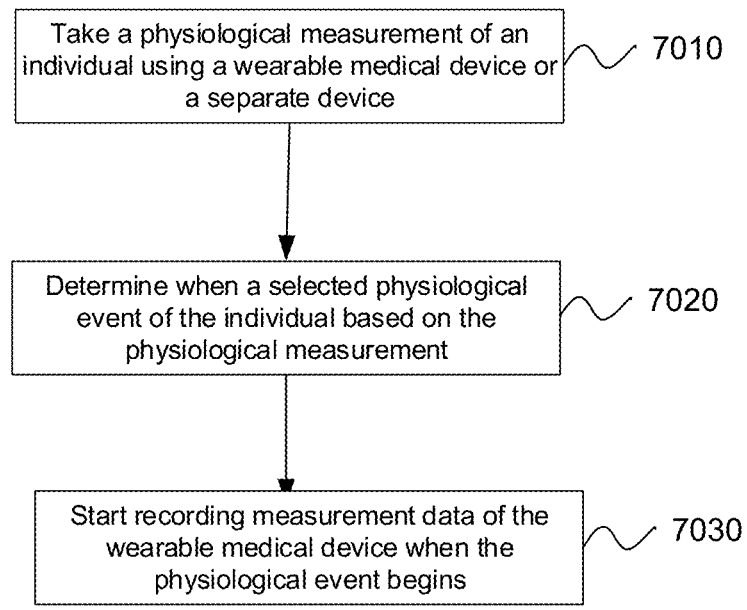
FIG. 70 depicts the functionality of another the computer circuitry of a wearable medical device that is operable calibrate sensors of the wearable medical device or medical measurements of the wearable medical device in accordance with an example.

FIG. 70 provides a flow chart 7000 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of an individual using a wearable medical device or a separate device, as in block 7010. The computer circuitry can be further configured to determine when a selected physiological event of the individual based on the physiological measurement, as in block 7020. The computer circuitry can be further configured to start recording measurement data of the wearable medical device when the physiological event begins, as in block 7030.

Figure 71:
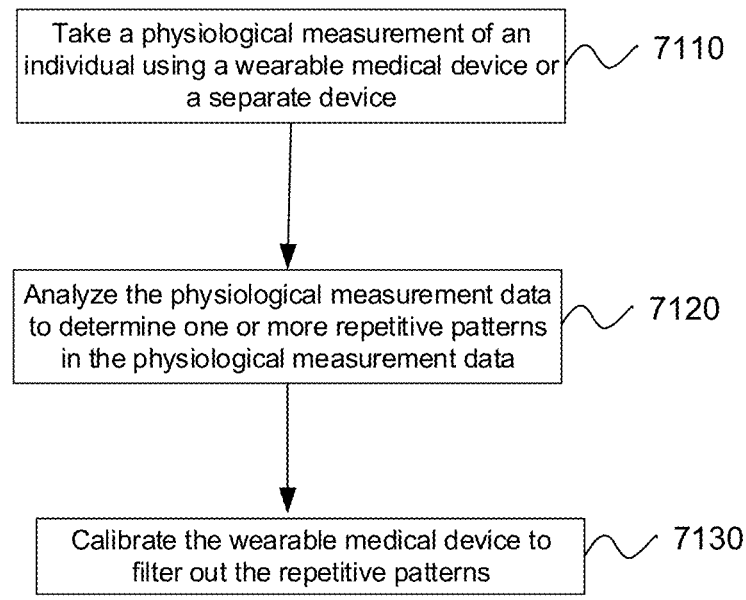
FIG. 71 depicts the functionality of another the computer circuitry of a wearable medical device that is operable calibrate sensors of the wearable medical device or medical measurements of the wearable medical device in accordance with an example.

FIG. 71 provides a flow chart 7100 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of an individual using a wearable medical device or a separate device, as in block 7110. The computer circuitry can be further configured to analyze the physiological measurement data to determine one or more repetitive patterns in the physiological measurement data, as in block 7120. The computer circuitry can be further configured to calibrate the wearable medical device to filter out the repetitive patterns, as in block 7130.

Figure 72:
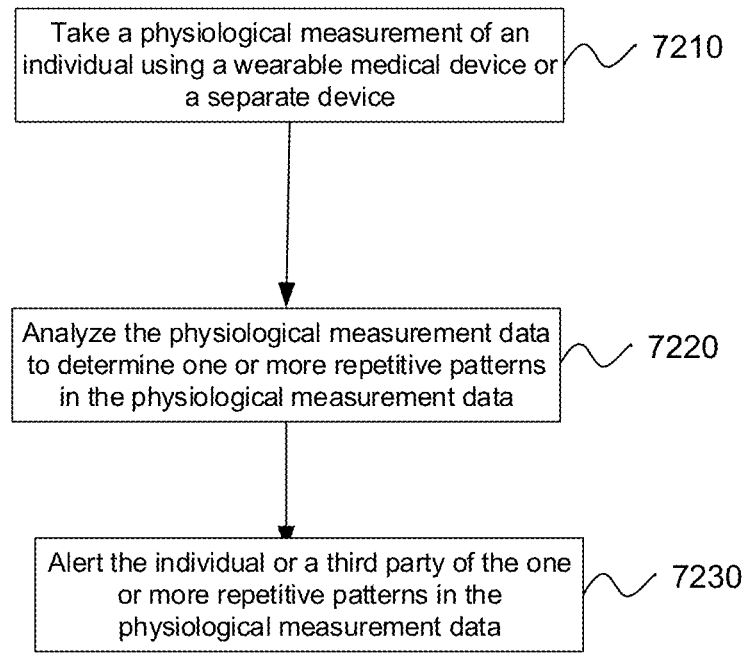
FIG. 72 depicts the functionality of another the computer circuitry of a wearable medical device that is operable calibrate sensors of the wearable medical device or medical measurements of the wearable medical device in accordance with an example.

FIG. 72 provides a flow chart 7200 to illustrate the functionality of one embodiment of the computer circuitry with a wearable medical device operable calibrate sensors of the wearable medical device or medical measurements of the wearable medical device. The functionality may be implemented as a method or the functionality may be executed as instructions on a machine, where the instructions are included on at least one computer readable medium or one non-transitory machine readable storage medium. The computer circuitry can be configured to take a physiological measurement of an individual using a wearable medical device or a separate device, as in block 7210. The computer circuitry can be further configured to analyze the physiological measurement data to determine one or more repetitive patterns in the physiological measurement data, as in block 7220. The computer circuitry can be further configured to alert the individual or a third party of the one or more repetitive patterns in the physiological measurement data, as in block 7230.

Figure 73:
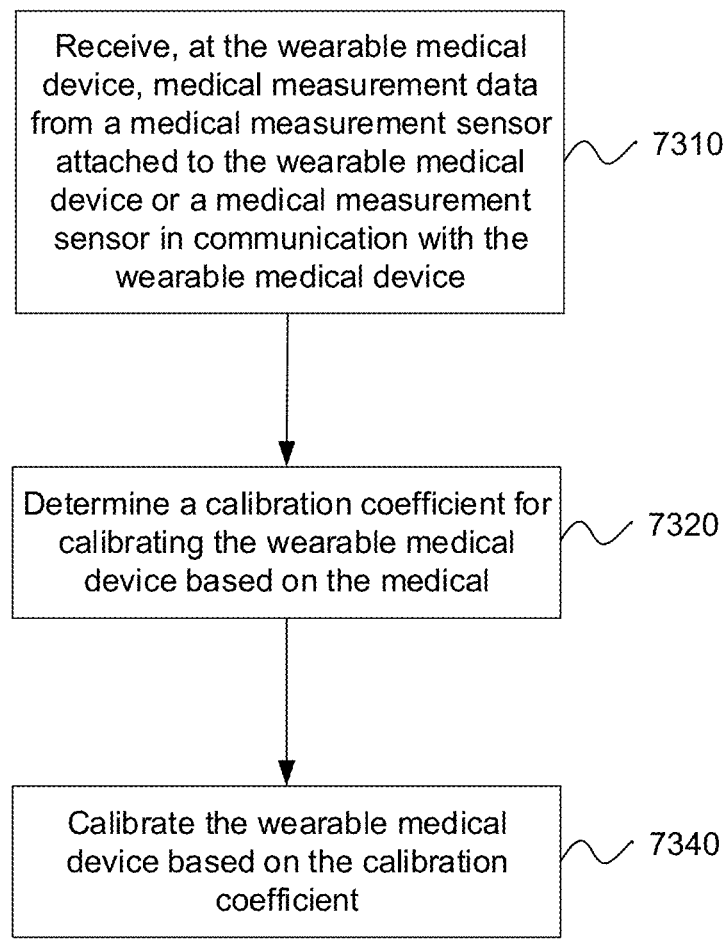
FIG. 73 depicts the functionality of another the computer circuitry of a wearable medical device that is operable calibrate sensors of the wearable medical device or medical measurements of the wearable medical device in accordance with an example.

FIG. 73 provides a flow chart 7300 to illustrate the functionality of one embodiment of the computer circuitry with a wearable medical device for monitoring medical parameters of a user. The functionality may be implemented as a method or the functionality may be executed as instructions on a machine, where the instructions are included on at least one computer readable medium or one non-transitory machine readable storage medium. The computer circuitry can be configured to receive, at the wearable medical device, medical measurement data from a medical measurement sensor attached to the wearable medical device or a medical measurement sensor in communication with the wearable medical device, as in block 7310. The computer circuitry can be further configured to determine a calibration coefficient for calibrating the wearable medical device based on the medical, as in block 7320. The computer circuitry can be further configured to calibrate the wearable medical device based on the calibration coefficient, as in block 7330.

In one embodiment, the computer circuitry can be further configured to determine a movement of the wearable medical device and filter out interference or noise in the medical measurement data caused by the movement of the wearable device. In another embodiment, the computer circuitry can be further configured to receive a baseline value to use as an initially reference point for the medical measurement data from the medical measurement sensor, reset the baseline value based on the calibration coefficient, and compare the medical measurement data to the reset baseline value to determine a medical condition of an individual using the wearable medical device. In another embodiment, the computer circuitry can be further configured to filter the medical measurement data from the medical measurement sensor or smooth the medical measurement data from the medical measurement sensor.

In another embodiment, the computer circuitry can be further configured to determine the calibration coefficient using a multivariate analysis or a regression analysis. In another embodiment, the computer circuitry can be further configured to receive environmental measurement data from an environmental measurement sensor attached to the wearable medical device or an environmental measurement sensor in communication with the wearable medical device and determine a calibration coefficient for calibrating the wearable medical device based on the environmental measurement data. In another embodiment, the calibration coefficient is based on: demographic information of the user; recursive data points in the medical measurement data; data collected from a plurality of individuals; a sudden shift in the medical measurement data; or previous medical measurement data of the user.

In another embodiment, the computer circuitry can be further configured to receive medical measurement data from an other medical measurement sensor, wherein the medical measurement sensor and the other medical measurement sensor provide orthogonal medical measurement data to the wearable medical device. In another embodiment, the computer circuitry can be further configured to aggregate medical measurement data from the medical measurement sensor and the other medical measurement sensor, wherein the medical measurement sensor and the other medical measurement sensor provide orthogonal medical measurement data.

In another embodiment, the computer circuitry can be further configured to receive measurement data from an other device and determine a calibration coefficient based on the measurement data from the other device. In another embodiment, the computer circuitry can be further configured to receive measurement data from another device and determine a calibration coefficient based on a correlation between measurement data from other device and the medical measurement data from the medical measurement sensor of the wearable medical device.

Figure 74:
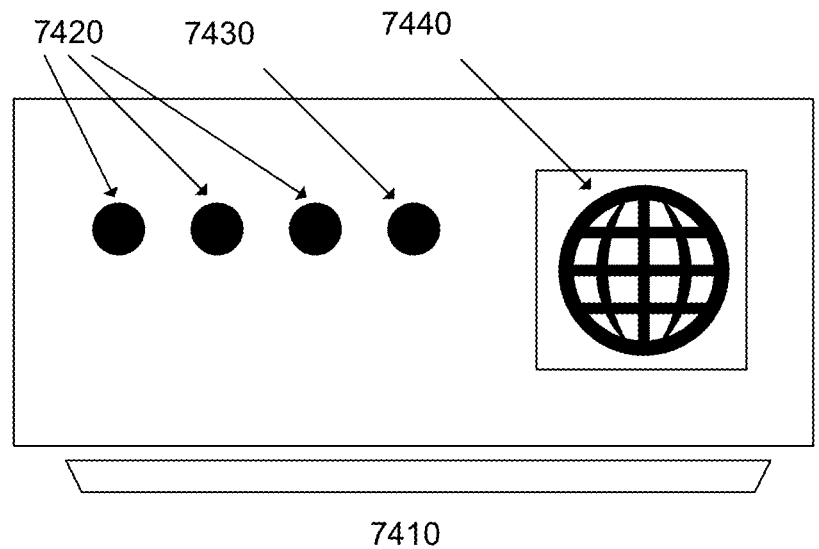
FIG. 74 illustrates a physiological measurement device 7410 for taking a physiological measurement of a user in accordance with an example.

FIG. 74 illustrates a physiological measurement device 7410 for taking a physiological measurement of a user. The physiological measurement device 7410 can include an authentication module 7420 to authenticate when a selected user is using the physiological measurement device. The physiological measurement device 7410 can also include a physiological sensor 7430 for taking a physiological measurement of the selected user at a time approximate to when the selected user is authenticated. The physiological measurement device 7410 can also include a communicate module 7440 to communicate physiological measurement information from the physiological measurement device to a selected wearable device.

In one embodiment, the authentication module 7420 further comprises a proximity sensor to determine when the selected user is within a threshold distance of the physiological measurement device. In another embodiment, the authentication module 7420 can include a proximity sensor that communicates a beacon signal to the selected wearable medical device and a receiver that receives a beacon signal from the wearable medical device when the wearable medical device is within a threshold distance of the physiological measurement device.

Figure 75:
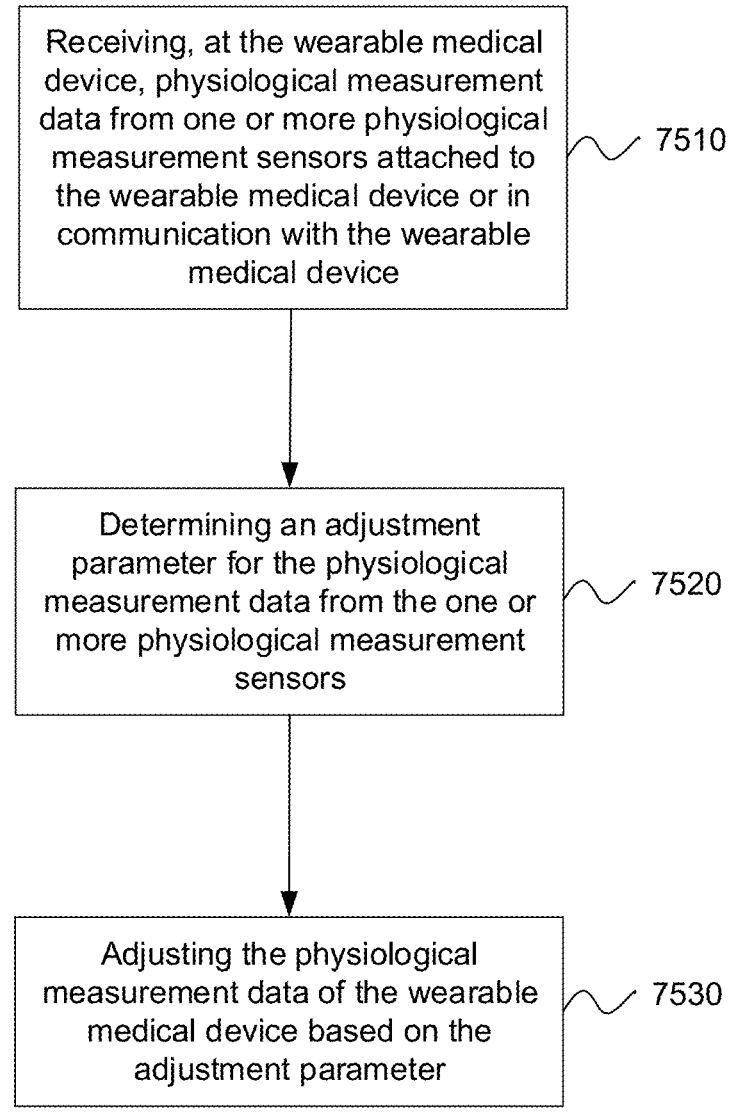
FIG. 75 illustrates a method for method for calibrating a wearable medical device. in accordance with an example.

FIG. 75 provides a flow chart 7500 for method for calibrating a wearable medical device. The method can comprise receiving, at the wearable medical device, physiological measurement data from one or more physiological measurement sensors attached to the wearable medical device or in communication with the wearable medical device, as in block 7510. The method can further comprise determining an adjustment parameter for the physiological measurement data from the one or more physiological measurement sensors, as in block 7520. The method can also comprise adjusting the physiological measurement data of the wearable medical device based on the adjustment parameter, as in block 7530.

In one embodiment, the method can further comprise determining an identity of the user of the wearable medical device and calibrating the wearable medical device based on the identity of the user. In another embodiment, the method can further comprise determining a location of the wearable medical device or one or more of the physiological measurement sensors on the body of a user of the wearable medical device, determining when the wearable medical device or one or more of the physiological measurement sensors is relocated to an other location on the body of a user of the wearable medical device, and calibrating the wearable medical device or one or more of the physiological measurement sensors based the other location of the wearable medical device or one or more of the physiological measurement sensors on the body of a user of the wearable medical device.

In another embodiment, the method can further comprise analyzing the physiological measurement data for recursive data points in a physiological measurement data set, and calibrating the wearable medical device or one or more of the physiological measurement sensors based the recursive data points in a physiological measurement data set. In another embodiment, the method can further comprise receiving, at the wearable medical device, health information of a user of the wearable medical device, and calibrating the wearable medical device or one or more of the physiological measurement sensors based on the health information of the user. In another embodiment, the method can further comprise determining one or more repetitive data points or repetitive data sets of the physiological measurement data and calibrating the physiological measurement data based on the repetitive data points or repetitive data sets of the physiological measurement data.

In another embodiment, the method can further comprise determining an error rate of the physiological measurement data and adjusting the wearable medical device or one or more of the physiological measurement sensors when the error rate of the physiological measurement data exceeds a selected error rate threshold. In another embodiment, the method can further comprise determining a standard deviation of the received physiological measurement data and adjusting the wearable medical device or one or more of the physiological measurement sensors when the standard deviation of the physiological measurement data exceeds a selected standard deviation threshold. In another embodiment, the method can further comprise determining an accuracy rate of the physiological measurement data, and adjusting the wearable medical device or one or more of the physiological measurement sensors when the accuracy rate of the physiological measurement data decreases below selected accuracy rate threshold.

What is claimed:

1. A wearable device, comprising:
   a first sensor to measure a first physiological characteristic of a user to obtain a first set of physiological data;
   a second sensor to measure a second physiological characteristic of the user to obtain a second set of physiological data, wherein the second sensor is different than the first sensor; and
   a processing device to:
   identify a first data point in the first set of physiological data that is orthogonal to a second data point in the second set of physiological data; and
   determine a calibration coefficient for calibrating the first sensor or a measurement from the first sensor based on the first data point and the second data point;
   determine an accuracy level of the first set of physiological data; and
   in response to the accuracy level of the first set of physiological data being below a threshold level, calibrate the first sensor or the measurement from the first sensor based on the calibration coefficient.

2. The wearable device of claim 1, wherein to determine the calibration coefficient and calibrate the first sensor or the measurement from the first sensor, the processing device is further to:
   identify a trend of a physiological characteristic of the user;
   determining the calibration coefficient based on the trend; and
   calibrating the first sensor or the measurement from the first sensor based on the calibration coefficient.

3. The wearable device of claim 2, whether in the trend is indicative of a threshold weight gain by the user or a threshold weight loss by the user.

4. The wearable device of claim 3, wherein the processing device is to:
   receive weight data of the user from another device;
   determine a first weight of the user at a first point in time;
   determine a second weight of the user at a second point in time;
   determine a third weight of the user at a third point in time; and
   determine the trend based on the first weight of the user, the second weight of the user, and the third weight of the user.

5. The wearable device of claim 2, wherein the trend is a trend in the first set of physiological data.

6. The wearable device of claim 1,
   wherein the processing device is to perform multivariate analysis on the first set of physiological data and the second set of physiological data to determine the calibration coefficient, wherein:
   the multivariate analysis is an analysis of more than one variable of the first set of the physiological data and the second set of physiological data; and the multivariate analysis is an analysis of the more than one variable of the first set of the physiological data and the second set of physiological data across multiple dimensions to account the more than one variable.

7. The wearable device of claim 1, further comprising a third sensor to measure an environmental characteristic of an area approximate to the user to obtain a first set of environmental data, wherein the processing device is to:
   determine an environmental interference on the first set of physiological data based on the first set of environmental data;
   determine the calibration coefficient indicating a change is an accuracy of the first set of physiological data in view of the environmental interference; and
   calibrate the first sensor or the measurement from the first sensor based on the calibration coefficient.

8. The wearable device of claim 1, further comprising a communication device configured to receive medical data from an external device, wherein the processing device is to:
   determine a medical condition of the user indicated in the medical data; and
   calibrate the first sensor or the measurement from the first sensor in view of the medical condition of the user.

9. The wearable device of claim 1, wherein to determine the calibration coefficient, the processing device is further to:
   determine a health status of the user; and
   determine the calibration coefficient based on the health status of the user.

10. The wearable device of claim 1, wherein to determine the calibration coefficient, the processing device is further to:
    receive, from another device, a second set of physiological data for a group of individuals;
    generate a histogram based on the second set of physiological data; and
    determine the calibration coefficient based on the histogram and the first set of physiological data.

11. The wearable device of claim 1, wherein to determine the calibration coefficient, the processing device is further to:
    receive, from another device, medical data indicating a medical condition of the user; and
    determine the calibration coefficient based on the first set of physiological data and the medical condition of the user.

12. The wearable device of claim 1, wherein to determine the calibration coefficient and calibrate the first sensor or the measurement from the first sensor, the processing device is further to:
    receive, from another device, medical data indicating a medical condition of the user; and
    identify the calibration coefficient for another user with the same medical condition; and
    calibrating the first sensor or a measurement from the first sensor using the calibration coefficient for the other user.

13. The wearable device of claim 1, wherein to determine the calibration coefficient and, the processing device is further to:
    determine whether the first set of physiological data is at least a standard deviation of from a second set of physiological data;
    determine the calibration coefficient to decrease a difference between the first set of physiological data and the second set of physiological data to be less than the standard deviation; and
    calibrating the first sensor or the measurement from the first sensor based on the calibration coefficient.

14. The wearable device of claim 1, wherein to determine the calibration coefficient and calibrate the first sensor or the measurement from the first sensor, the processing device is further to:
    identify a pattern of a physiological characteristic of the user in the first set of physiological data;
    determining the calibration coefficient based on the pattern; and
    calibrating the first sensor or the measurement from the first sensor based on the calibration coefficient.

15. A non-transitory computer-readable storage medium comprising instructions configured to cause a computing device to perform operations, the operations comprising:
    receiving, from a first sensor, a first physiological characteristic of a user to obtain a first set of physiological data, the first sensor being physically coupled to a wearable device;
    receiving, from a second sensor, a second physiological characteristic of the user to obtain a second set of physiological data, the second sensor being physically coupled to the wearable device;
    identifying a first data point in the first set of physiological data that is orthogonal to a second data point in the second set of physiological data;
    determining a unique physiological characteristic of the user based on the first set of physiological data;
    determining a calibration coefficient the sensor or measurements from the sensor for the unique physiological characteristic in view of the first data point and the second data point; and
    calibrating the sensor or the measurement from the sensor based on the calibration coefficient.

16. The computer-readable storage medium of claim 15, wherein the unique physiological characteristic of the user is a physiological characteristic that is different than a physiological characteristic of another user of the wearable device.

17. The computer-readable storage medium of claim 15, wherein the unique physiological characteristic of the user is a physiological characteristic common to a defined group of individuals.

18. A method, comprising:
    measuring, by a first sensor, a first physiological characteristic of a user to obtain a first set of physiological data;
    measuring, by a second sensor, a second physiological characteristic of the user to obtain a second set of physiological data;
    identifying, by a processor, a first data point in first set of physiological data that is orthogonal to a second data point in the second set of physiological data;
    determining, by the processor, a first calibration coefficient for calibrating the first sensor or the measurement from the first sensor based on the first data point and the second data point; and
    calibrating, by the processor, the first sensor or the measurement from the first sensor based on the determined first calibration coefficient.

19. The method of claim 18, wherein calibrating the first sensor or the measurement from the first sensor further comprises:

determining, by the processor, a first error rate of the first set of physiological data;
calibrating, by the processor, a wearable device based on the first calibration coefficient to reduce the first error rate;
measuring, by the first sensor, the first physiological characteristic of the user to obtain a second set of physiological data;
determining, by the processor, a second error rate of the second set of physiological data;
determining, by the processor, whether the second set of physiological data is in a stable state;
when the second set of physiological data is in the stable state where the second error rate is below a threshold error rate level, calibrating, by the processor, the wearable device based on the first calibration coefficient; and
when the second set of physiological data is not in the stable state where the second error rate exceeds the threshold error rate level:
　　determining a second calibration coefficient to reduce the second error rate below the threshold error rate level; and
　　calibrating, by the processor, the wearable device based on the second calibration coefficient.

* * * * *